US011078266B2

(12) United States Patent
Mack et al.

(10) Patent No.: US 11,078,266 B2
(45) Date of Patent: Aug. 3, 2021

(54) ANTI-HUMAN IL-3 ANTIBODIES, THEIR USE IN TREATMENT OF A DISEASE OR MALFUNCTION ASSOCIATED WITH ELEVATED EXPRESSION OR LEVELS OF IL-3, AND THEIR USE IN A METHOD TO DETECT HUMAN IL-3

(71) Applicant: UNIVERSITÄTSKLINIKUM REGENSBURG, Regensburg (DE)

(72) Inventors: Matthias Mack, Regensburg (DE); Hilke Bruhl, Regensburg (DE); Kerstin Renner, Kofering (DE)

(73) Assignee: Universitätsklinikum Regensburg, Regensburg (DE)

( * ) Notice: Subject to any disclaimer, the term of this patent is extended or adjusted under 35 U.S.C. 154(b) by 428 days.

(21) Appl. No.: 15/775,283

(22) PCT Filed: Nov. 10, 2016

(86) PCT No.: PCT/EP2016/077371
§ 371 (c)(1),
(2) Date: May 10, 2018

(87) PCT Pub. No.: WO2017/081218
PCT Pub. Date: May 18, 2017

(65) Prior Publication Data
US 2018/0371075 A1    Dec. 27, 2018

(30) Foreign Application Priority Data

Nov. 11, 2015 (EP) ................................ 15194062
Jun. 1, 2016 (EP) ................................ 16172551

(51) Int. Cl.
*C07K 16/24* (2006.01)
*G01N 33/68* (2006.01)

(52) U.S. Cl.
CPC ....... *C07K 16/244* (2013.01); *G01N 33/6869* (2013.01); *C07K 2317/14* (2013.01); *C07K 2317/21* (2013.01); *C07K 2317/24* (2013.01); *C07K 2317/33* (2013.01); *C07K 2317/34* (2013.01); *C07K 2317/52* (2013.01); *C07K 2317/76* (2013.01); *C07K 2317/92* (2013.01); *G01N 2333/5403* (2013.01)

(58) Field of Classification Search
None
See application file for complete search history.

(56) References Cited

FOREIGN PATENT DOCUMENTS

| WO | 2005051999 | 6/2005 |
|---|---|---|
| WO | 2010063488 | 6/2010 |
| WO | 2013178706 | 12/2013 |
| WO | 2013178707 | 12/2013 |
| WO | 2015063228 | 5/2015 |

OTHER PUBLICATIONS

Vajdos et al. (J Mol Biol. Jul. 5, 2002;320(2):415-28 at 416) (Year: 2002).*
Brown et al. (J Immunol. May 1996; 156(9):3285-91 (Year: 1996).*
Abrams et al., "Development of Rat Anti-Mouse Interleukin 3 Monoclonal Antibodies Which Neutralize Bioactivity in Vitro", The Journal of Immunology, vol. 140, No. 1, Jan. 1, 1988, pp. 131-137.
Bradbury et al., "Reproducibility: Standardize antibodies used in research", Nature, vol. 518, No. 7537, Feb. 2015, pp. 27-29.
Chen et al., "A New Isoform of Interleukin-3 Receptor a with Novel Differentiation Activity and High Affinity Binding Mode", J. Biol. Chem., vol. 284, No. 9, pp. 5763-5773, Feb. 27, 2009.
Ding et al., "Molecular closing, expression, purification, and characterization of soluble full-length, human interleukin-3 with a baculovirus-insect cell expression system", Protein Expression and Purification, vol. 31, 2003, pp. 34-41.
Dorssers et al., Receptor and Antibody Interactions of Human Interleukin-3 Characterized by Mutational Analysis, J. Biol. Chem., vol. 266, No. 31, pp. 21310-21317, 1991.
Emanuel et al., "Specific inhibition of interleukin 3 bioactivity by a monoclonal antibody reactive with hematopoietic progenitor cells", Proceedings National Academy of Sciences PNAS, vol. 87, No. 12, Jun. 1, 1990, pp. 4449-4452.
Hauswirth et al., "Interleukin-3 Promotes the Expression of E-NPP3/CD203C on Human Blood Basophils in Healthy Subjects and in Patients with Birch Pollen Allergy", International Journal of Immunopathology and Pharmacology, vol. 20, No. 2, Apr. 1, 2007, pp. 267-278.
Hemminki et al., "Familial Associations of Rheumatoid Arthritis With Autoimmune Diseases and Related Conditions", Arthritis & Rheumatism, vol. 60, No. 3, Mar. 2009, pp. 661-668.
Jones et al., "Enhancement of the Biologic Effects of Interleukin-3 In Vivo by Anti-Interleukin-3 Antibodies", Blood, vol. 82, No. 4, Aug. 15, 1993, pp. 1133-1141.
Kaushansky et al., "Structure-Function Relationships of Interleukin-3 An Analysis Based on the Function and Binding Characteristics of a Series of Interspecies Chimera of Gibbon and Murine Interleukin-3", J. Clin, Invest., vol. 90, Nov. 1992, pp. 1879-1888.
Lokker et al., "Mapping the Epitopes of Neutralizing Anti-Human IL-3 Monoclonal Antibodies", The Journal of Immunology, vol. 146, No. 3, pp. 893-898, Feb. 1, 1991.
Lokker et al., "Structure-Activity Relationship Study of Human Interleukin-3 Identification of Residues Required for Biological Activity by Site-Directed Mutagenesis", J. Biol. Chem., vol. 266, No. 16, Jun. 5, 1991, pp. 10624-10631.

(Continued)

*Primary Examiner* — Gary B Nickol
*Assistant Examiner* — Jegatheesan Seharaseyon
(74) *Attorney, Agent, or Firm* — Kilpatrick Townsend & Stockton LLP

(57) ABSTRACT

Anti-human interleukin 3 (IL-3) antibodies or fragments thereof according to the present invention are useful as therapeutic agents. The antibodies can be used in pharmaceutical compositions for the treatment or prevention of diseases which are associated with elevated expression or levels of human IL-3 in a patient, especially inflammatory or autoimmune diseases, such as rheumatoid arthritis. The antibodies can also be used to detect human IL-3 expressed by human cells.

8 Claims, 52 Drawing Sheets

Specification includes a Sequence Listing.

(56) References Cited

OTHER PUBLICATIONS

Padyukov et al., "A Gene-Environment Interaction Between Smoking and Shared Epitope Genes in HLA-DR Provides a High Risk of Seropositive Rheumatoid Arthritis", Arthritis & Rheumatism, vol. 50, No. 10, Oct. 2004, pp. 3085-3092.
PCT/EP2016/077371, "International Preliminary Report on Patentability", dated May 15, 2018.
PCT/EP2016/077371, "International Search Report and Written Opinion", dated May 22, 2017.
R&D Systems, "Human IL-3 Antibody Antigen Affinity-Purified Polyclonal Goat IgG, Catalog Number: AF-203-NA", http://www.mdsystems.cornipfdiaf203na.pdf, 2011, 1 page.
R&D Systems, "Human IL-3 Antibody Monoclonal Mouse IgG1 Clone #4815, Catalog Number: MAB603", http://www.rndsystems.com/pdf/mab603.pdf, 2011, 2 pages.
Sturm et al., "CD203c-Based Basophil Activation Test in Allergy Diagnosis: Characteristics and Differences to CD63 Upregulation", Cytometry Part B: Clinical Cytometry, vol. 78B, No. 5, Sep. 1, 2010, pp. 308-318.
Sugayama, Morikawa, Matsuura, Tkachenko, Morita, Komatsu, Akao and Kitamura, Four Serotypes of Haemorrhagic Fever with Renal Syndrome Viruses Identified by Polyclonal and Monoclonal Antibodies, J. Gen. Virol. vol. 68, 1987, pp. 979-987.
Ziltener, "Glycosylation Does Not Affect In-Vitro Biological Activity of Interleukin-3", Cytokine, vol. 5, No. 4, pp. 291-297, Jul. 1993.
Ziltener et al., "Multiple Glycosylated Forms of T Cell-derived Interleukin 3 (Il-3); Heterogeneity of IL-3 from Physiological and Nonphysiological Sources", Journal of Biological Chemistry, vol. 263, No. 28, Oct. 5, 1988, pp. 14511-14517.

\* cited by examiner

Aminoacid identity of IL-3 between various species

- Human – Mouse: 29%
- Human – Rat: 30%
- Mouse – Rat: 60%
- Human – Marmoset: 72%
- Human – Rhesus: 84%
- Human – Chimpanzee: 99%

Human IL-3 is partially active in Rhesus but not in Marmoset
Rhesus IL-3 is active in humans

Fig. 1

ANTI-HUMAN IL-3 ANTIBODIES, THEIR USE IN TREATMENT OF A DISEASE OR MALFUNCTION ASSOCIATED WITH ELEVATED EXPRESSION OR LEVELS OF IL-3, AND THEIR USE IN A METHOD TO DETECT HUMAN IL-3

FIELD OF THE INVENTION

The present invention relates to anti-human interleukin 3 (IL-3) antibodies, nucleic acid sequences encoding such antibodies and hybridoma cell lines producing the antibodies according to the present invention. The invention further relates to pharmaceutical compositions containing anti-human IL-3 antibodies, which are useful for the prevention or treatment of diseases or malfunctions which are associated with elevated levels of IL-3 in a human patient, and to methods of determining the capability of anti-human IL-3 antibodies to block the activity of IL-3 in humans. Moreover, the present invention relates to the use of such antibodies in a method to detect human IL-3.

BACKGROUND

Interleukins belong to the large family of proteins called cytokines. Cytokines are polypeptides that influence the function of certain cells upon binding to specific cellular receptors and are divided in subclasses, i.e., interleukins, interferons, colony-stimulating factors (CSFs), lymphokines, growth factors and monokines. It is well known that cytokines play a major role in cell proliferation and, e.g., also inflammatory diseases.

Cell proliferation is a complex process wherein growth factors bind to specific receptors on the cell surface, whereupon endocytosis occurs and the complexes of cytokine and receptor are internalized causing a cellular response. Such cellular responses include specific gene transcription activities as DNA synthesis and cell replication. When tested in relatively high concentrations, most of the cytokines have several differing biological effects. Because of these effects of cytokines, there is a high interest in investigations for possible therapeutic uses of these proteins.

Interleukins are mediators of the immune system which are produced in low concentration mostly in leukocytes. They influence growth, differentiation and activity of cells of the immune system and thus belong to the immune modulators. They also take effect by binding to receptors on the surface of target cells and thus change the transcription rate of certain genes. They play an important role in the triggering of a multiplicity of cellular responses.

Interleukins are, e.g., involved in the immunological cell activation cascade and subsequent inflammatory changes. Irregular and/or abnormal inflammation is a major component and factor of a wide range of human diseases, one of which is the immunological disorder rheumatoid arthritis (RA). But also other immunological diseases are influenced by interleukins.

IL-3, also designated as Multi-CSF, is a well-known member of the interleukin family. It has a growth stimulating and differentiating effect on various hematopoietic precursor cells and acts as a growth factor for mast cells. Together with IL-5 and GM-CSF, IL-3 belongs to the family of hematopoietic cytokines with four short alpha-helical bundles. GM-CSF and IL-3 stimulate the formation of neutrophilic and eosinophilic granulocyte colonies as well as macrophages. It further stimulates the formation of mast, megakaryocyte and pure and mixed erythroid colonies (D. Metcalf, "The hematopoietic colony-stimulating factors", 1984, Elsevier, Amsterdam).

IL-3 consists of 133 amino acids and is known for its stimulation of colony formation by human hematopoietic progenitor cells and the stimulation of DNA synthesis by human acute myelogenous leukemia (AML) blasts. IL-3 binds to a unique receptor also known as CD123 antigen. The receptor belongs to the type I cytokine receptor family and is a heterodimer with a unique α-chain paired with a common β-subunit (βC or CDW 131). IL-3 binds to the unique α-receptor subunit. Signal transduction is mediated, however, by the common β-receptor subunit (βC) by the JAK2-STAT5 pathway.

Human IL-3 has two potential N-glycosylation sites—aa N15 and aa N70 of the amino acid sequence of human IL-3 as defined in SEQ ID: 10:

```
APMTQTTSLK TSWVNCSNMI DEIITHLKQP PLPLLDFNNL

NGEDQDILME NNLRRPNLEA FNRAVKSLQN ASAIESILKN

LLPCLPLATA APTRHPIHIK DGDWNEFRRK LTFYLKTLEN

AQAQQTTLSL AIF.
```
(glycosylation sites are bolded)

It is well established that IL-3 expressed by eukaryotic cells is N-glycosylated (see data sheets from Biolegend and Biomol and Protein Expr Purif. 2003 September; 31(1):34-41). The glycosylated and non-glycosylated versions of IL-3 have similar bioactivity as measured by IL-3 induced proliferation of tumor cells (data sheets from Peprotech, Biolegend, Biomol and Protein Expr Purif. 2003 September; 31(1):34-41, as well as shown below). For murine IL-3 it was also shown that glycosylation does not affect bioactivity of IL-3 (Cytokin 1993; 5:291-297, J. Biol. Chem. 1988, 263:14511-17).

So far there have been no hints in the literature that glycosylation affects the ability of monoclonal antibodies to block IL-3 bioactivity. The inhibitory activity of monoclonal antibodies was characterized with either *E. coli* derived IL-3 (J Biol. Chem 1991; 266:10624-31, J. Immunol. 1991; 146:893-8) or aglycosylated IL-3 (J Biol Chem 1991; 266:21310-17). The binding of antibodies to IL-3 was tested with glycosylated and non-glycosylated IL-3 and was found to be independent on the glycosylation. IL-3 is mainly produced by activated CD4+ T-cells and contributes especially to growth, differentiation and survival of CD34+ hematopoietic progenitor cells. In vitro, IL-3 has been observed to promote the differentiation of basophils and mast cells from bone marrow cells. It has further been observed to induce IL-6 release by murine basophils and to up-regulate MHC-II expression and IL-1 secretion in monocyte/macrophages. Further, IL-3 supports the differentiation of monocytes into dendritic cells and osteoclasts.

Since the first detection of IL-3 in a human genomic library, it has been a focus of investigations to determine its role in healthy humans as well as its possible role in the occurrence of diseases. The ability of cytokines to initiate or regulate hematopoiesis is of interest, especially as far as malfunctions or diseases of the immune system are concerned. Such disorders seem to be connected to disturbances of the hematopoietic system and it was assumed that such diseases could be treated by providing viable progenitor cells to the hematopoietic system. Triggering such progenitor cells to differentiate was considered as a means to treat the respective diseases.

Until several years ago, little was known about the role of IL-3 in autoimmune diseases and especially rheumatoid arthritis (RA). RA is the most prevalent inflammatory disease of the joints. The initial disease stages often develop gradually but can also manifest themselves with an instantaneous outburst. While pain occurs predominantly in joints of the fingers or toes, also other joints can be affected. The affected joints show swelling and usually are hyperthermic. Mostly, the disease proceeds in episodes, an episode usually lasting between several weeks to months. In between episodes, generally, there is an improvement of symptoms.

The etiology of RA is not yet known. An autoimmune cause is strongly suspected with viral and bacterial causes being also discussed. A genetic influence has been reported by several authors (Hemminki K. et al., Arthritis Rheum. 2009; 60(3): 661-8, Padyukov L. et al., Arthritis Rheum. 2004; 50(10) 3085-92). It is assumed that misdirected immune cells invade the affected joints and cause the production of pro-inflammatory cytokines. According to one theory, the balance between cytokines is disturbed in RA. It has been reported that IL-1, IL-6 and TNFα are present in excess in RA and are assumed to be responsible for the deleterious inflammatory processes in cartilage tissue and for the activation of osteoclasts.

The treatment of rheumatoid arthritis is still considered difficult and burdensome to the patients since medications with a high risk of adverse side effects have to be used. One way of treating the disease is to perform a symptomatic treatment, mostly using non-steroidal anti-inflammatory drugs (NSAIDs). These drugs act as anti-inflammatory and analgetic agents and often only achieve an alleviation of pain. The drugs further interfere with a certain step in the inflammatory cascade, where prostaglandine is generated by cyclooxygenases. NSAIDs, however, do not influence the underlying inflammatory process and are thus not able to retard the joint destruction, which is the most deleterious effect of RA.

To prevent joint destruction and disease activity, a further current approach for treating RA is the use of disease-modifying anti-rheumatic drugs (DMARDs). These pharmaceuticals actually modify the disease process. Examples of DMARDs are methotrexate, the most commonly used anti-rheumatic, the effect of which is based on a reversible inhibition of the enzyme dihydrofolate reductase. Another commonly used substance for treating RA is leflunomide, which provides an effect by intervening with the pyrimidine metabolism. Both pharmaceuticals are long-acting and thus have to be administered over a longer period of time (usually 12-16 weeks) to show the desired effects. To bridge the time until DMARDs improve the disease, most patients are administered steroids.

A further approach for treating RA are "biologicals" that block cytokines like TNF, IL-6, IL-1 or costimulatory molecules like B7 or that deplete leukocyte subsets (e.g. B cells). Biologicals (e.g. the TNF antibody Infliximab) are mostly used for severe disease processes and after DMARDs have failed to sufficiently control disease activity. Biologicals influence a plurality of signal systems in the immune system and have a variety of serious side effects including bacterial and viral infections and a higher risk for development of neoplasia.

All known treatments have severe disadvantages and side effects and, therefore, it was an object to develop new drugs for the treatment of RA which are effective, are more selectively expressed than other cytokines in patients with autoimmune disease, especially RA, and have less side effects than the currently used treatment regimes.

More recently, an involvement of IL-3 in autoimmune diseases and especially in RA has been described. WO 2010/063488 describes that IL-3 inhibitors can be used in treatment of early stages of rheumatoid arthritis. Although the above cited patent application mentions that no IL-3 mRNA was detected in the synovium of patients with RA and no effect of IL-3 was observed on cultured fibroblasts, a genetic analysis found an association between a single nucleotide polymorphism in the IL-3 promoter gene and RA. Based on this finding and also further studies which show the presence of considerably elevated levels of IL-3 in RA patients, WO 2010/063488 proposes such use of inhibitors, mainly antibodies or antibody fragments, antibody variants or antibody multimers in prophylactic RA treatment, therapeutic treatment in early stages of the disease or in maintenance treatment.

However, there is still a need for effective antibodies with high specificity towards IL-3 which also show a high affinity and avidity. As the in vivo efficacy of an antibody to be used in the treatment of a disease or malfunction in a patient's body is essential, there is also an urgent need for antibodies, which are efficacious in the in vivo context. Such anti-IL-3 antibodies preferably should also exhibit none or very low cross reactivity with IL-3 from other species. Within this object of the present invention, it is desirable to provide antibodies which are able to inhibit the activity of IL-3 efficiently and specifically in vivo, thus making them useful agents for treating the disease in patients having been diagnosed for elevated levels of IL-3.

These objects of the present invention are solved by the anti-IL-3 antibodies or fragments, constructs, variants, or conjugates, thereof according to the present invention as specified in the appended claims and the following description.

It was a further object of the present invention to provide a method for efficiently obtaining anti-human IL-3 antibodies. It was a further object of the present invention to provide methods and tests to identify anti-human IL-3 antibodies, which are capable of blocking IL-3 activity in humans. A further object of the present invention was to provide antibodies, which can be used efficiently in a method for detection of human IL-3 expressed by human cells.

DESCRIPTION OF DRAWINGS

The invention is also explained with reference to the following figures.

The following figures further illustrate and describe the present invention but are not intended to limit the scope thereof.

FIG. 1 shows the amino acid sequence homology of IL-3 of various species.

FIG. 8 shows that clone P8C11C8-6 does not exhibit cross-reactivity with mouse or rat IL-3. ELISA wells were coated overnight with PBS, mouse IL-3, rat IL-3 or human IL-3 (1 µg/ml) in PBS. After washing and blocking with PBS/1% BSA (bovine serum albumin) clone P8C11C8-6 (40 µg/ml) or medium was applied for 1 h at room temperature. After washing a secondary HRP-labelled rabbit anti-mouse polyclonal antibody (P260, DakoCytomation) was applied. After washing a color substrate reaction was performed with ABTS and optical density was measured. The results shown in FIG. 8 were obtained by using human IL-3 expressed by insect cells (Recombinant Human IL-3 (carrier-free) Cat. #578002 from Biolegend). Therefore the human IL-3 peptide was glycosylated. In the test depicted in FIG. 9, also a commercially available anti-IL-3 antibody was included.

IL-3 (0.1 ng/ml) was preincubated with antibodies (10 µg/ml) for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 22:
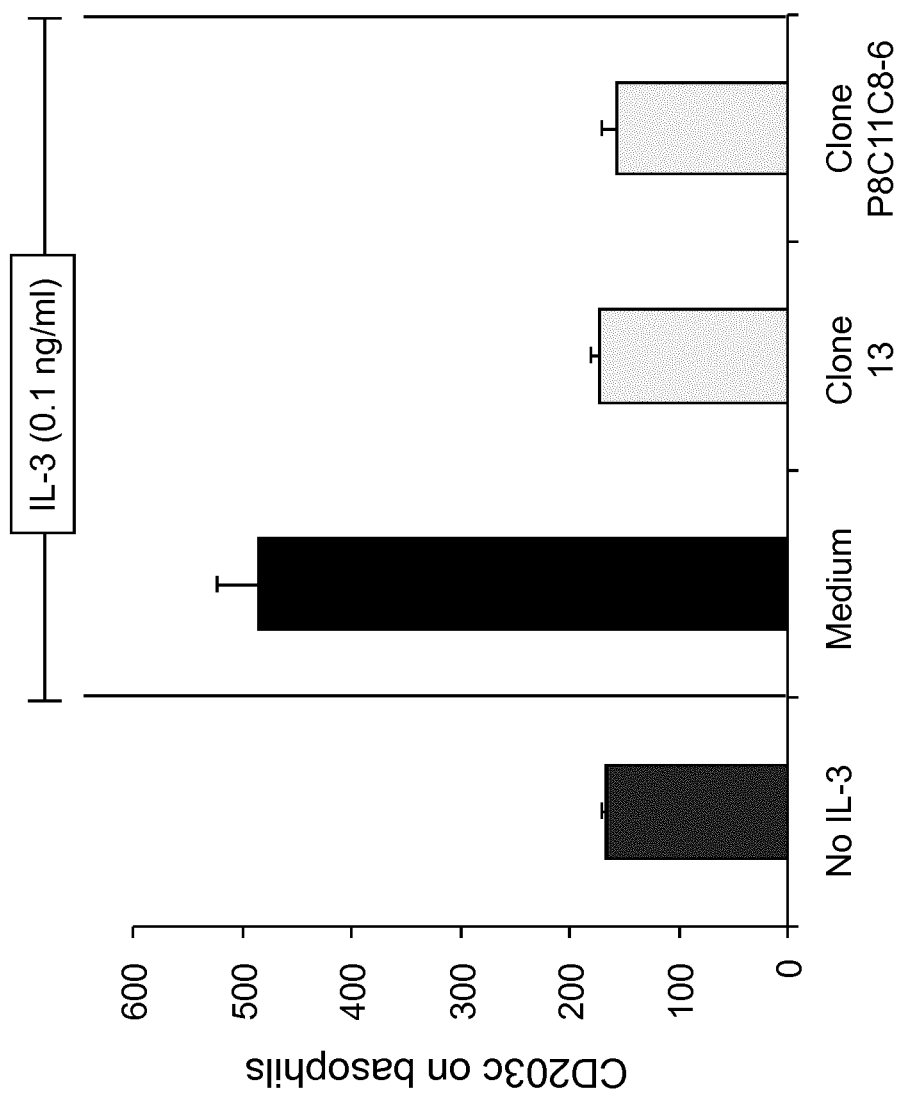

MOPC-21=mouse IgG1 kappa isotype control antibody. Clone 11, 13, 36, 44, 47, R&D 203 4806=anti-human IL-3 antibodies FIG. 22 shows IL-3 blockage in primary human blood cell derived from a blood sample obtained from a RA patient.

IL-3 (0.1 ng/ml) was preincubated with antibodies (10 µg/ml Clone 13 or 10 mg/ml P8C11C8-6) for 20 min at room temperature and added to fresh human EDTA blood from a patient with rheumatoid arthritis (RA). After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 23:
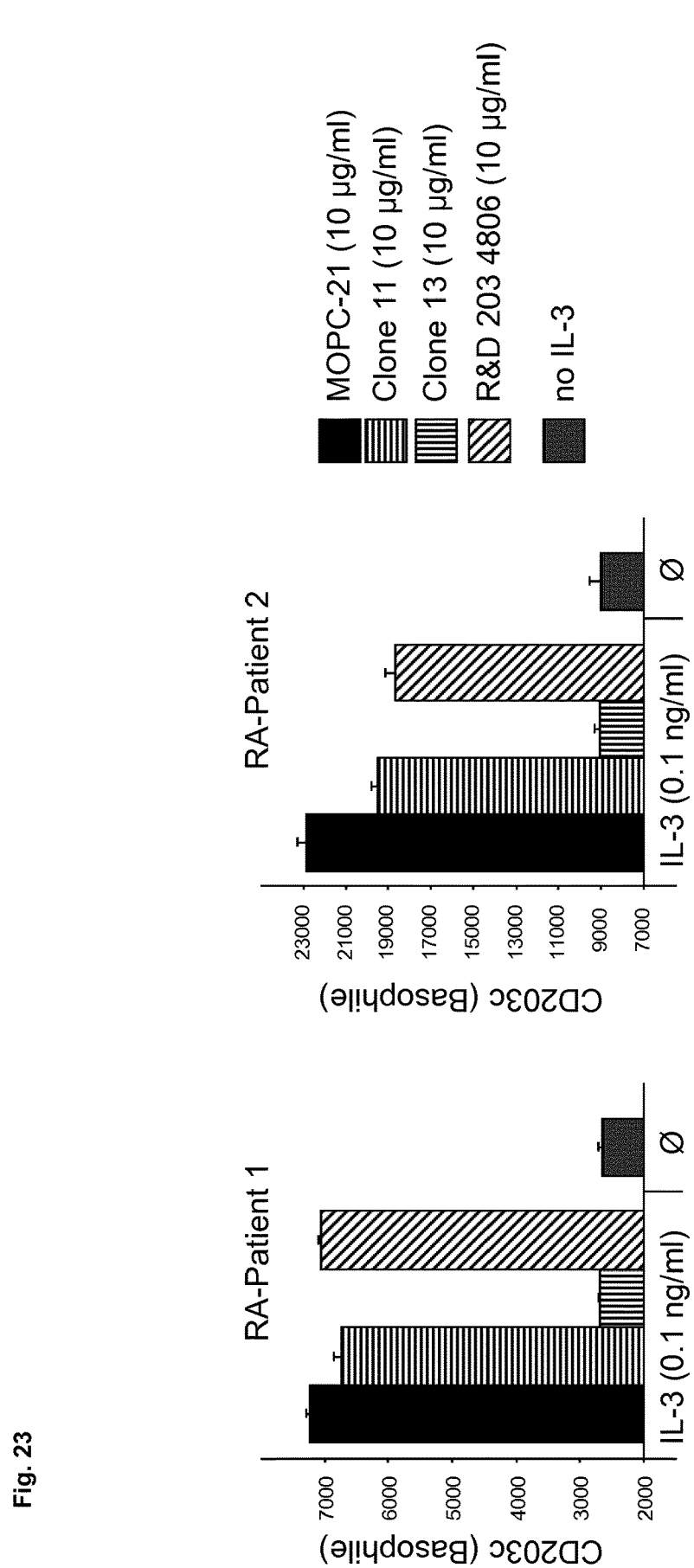

FIG. 23 shows the effects of antibodies on IL-3 induced upregulation of CD203c on basophils in samples obtained from 2 RA patients.

IL-3 (0.1 ng/ml) was preincubated with antibodies (10 µg/ml) for 20 min at room temperature and added to fresh EDTA blood from patients with RA. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 24:
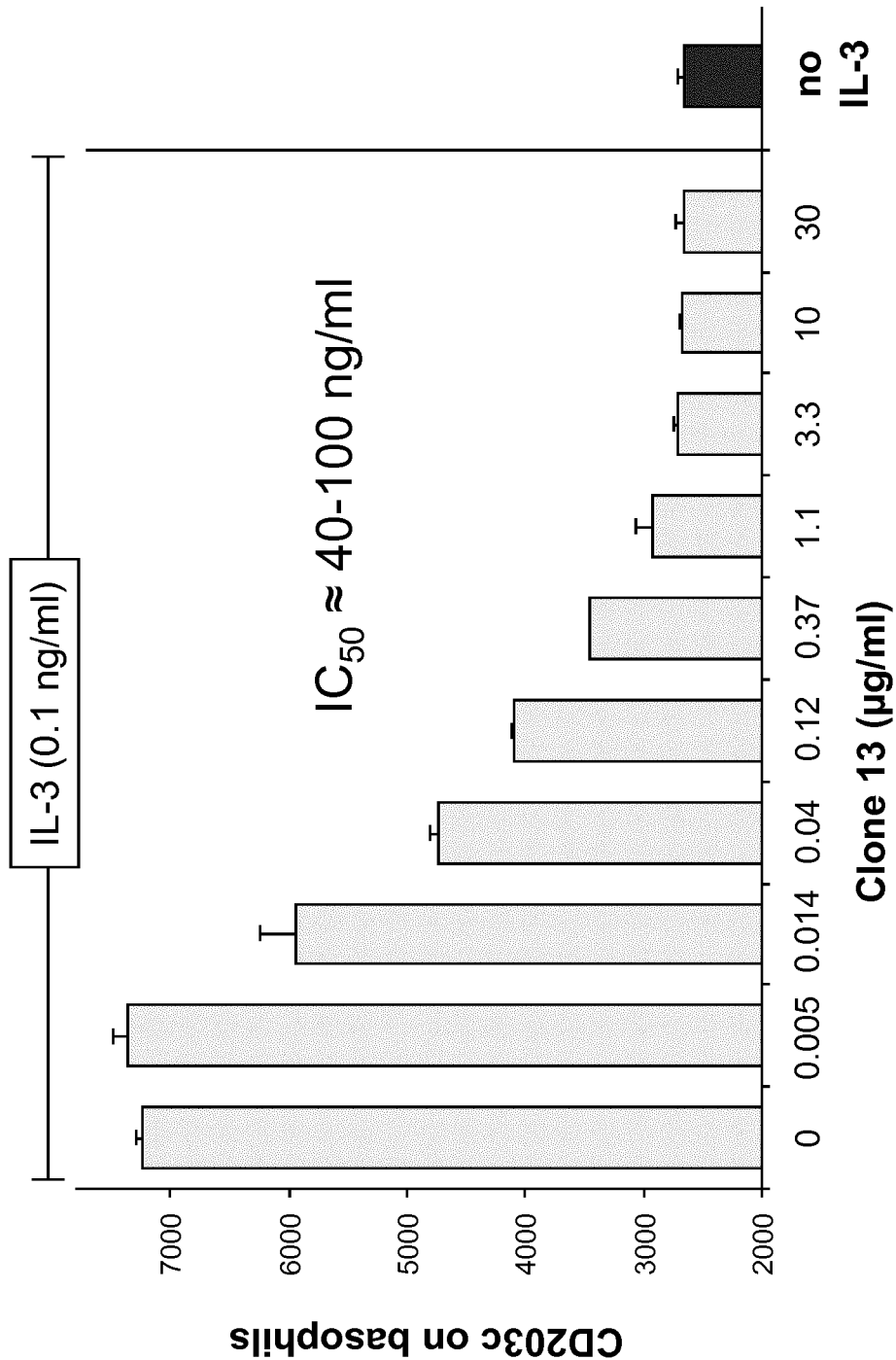

MOPC-21=mouse IgG1 kappa isotype control antibody. Clone 11, 13, 4806=anti-human IL-3 antibodies FIG. 24 shows blockage of IL-3 induced upregulation of CD203c on basophils by clone 13.

IL-3 (0.1 ng/ml) was preincubated with various concentrations of the IL-3 antibody clone 13 for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 25:
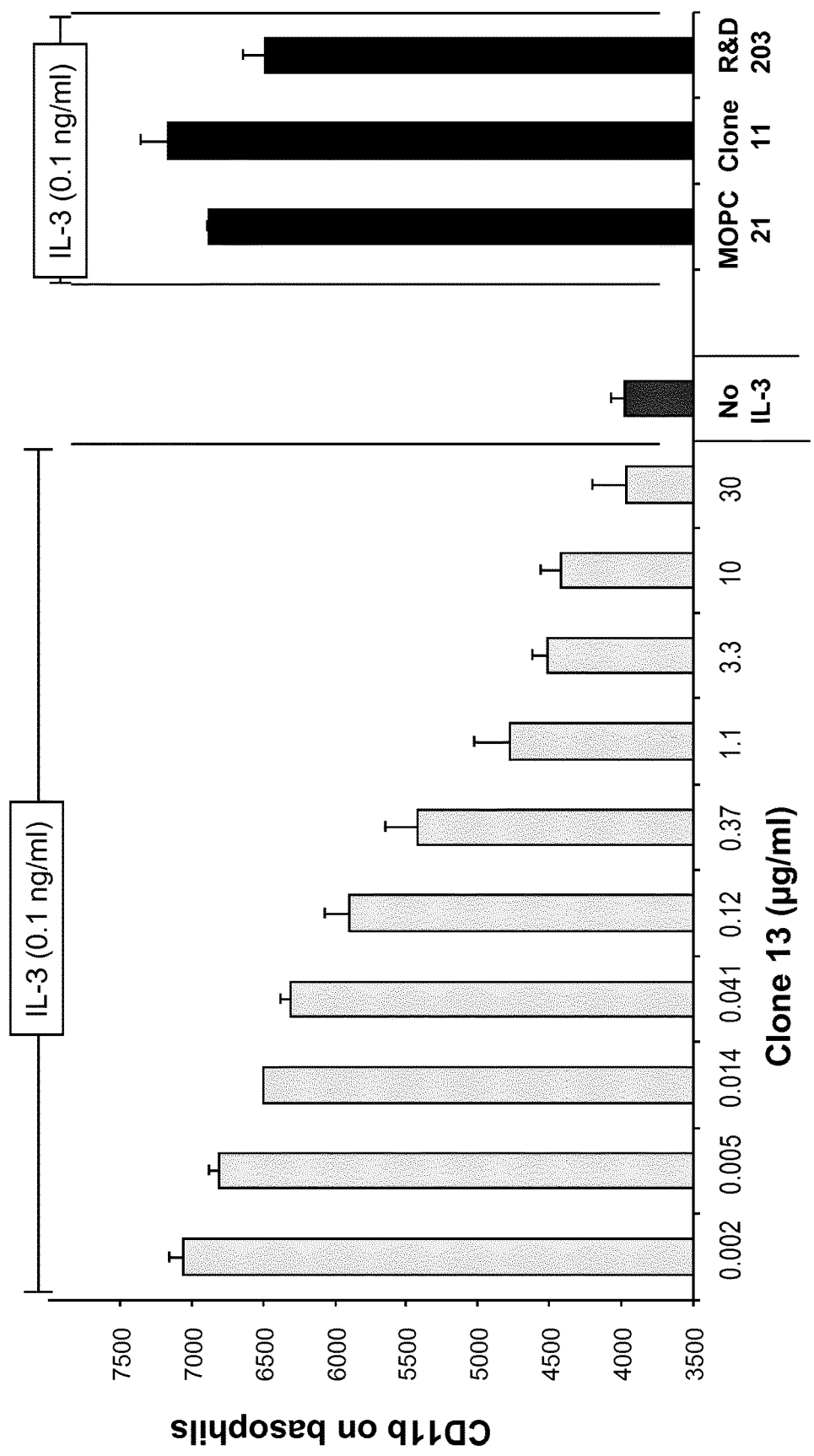

FIG. 25 shows blockage of IL-3 induced upregulation of CD11b on basophils by clone 13.

IL-3 (0.1 ng/ml) was preincubated with various concentrations of the IL-3 antibody clone 13 or with 10 µg/ml of MOPC-21 (mouse IgG1 isotype control antibody), clone 11 or R&D mab 203 (clone 4806) for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD11b on basophils.

Figure 26:
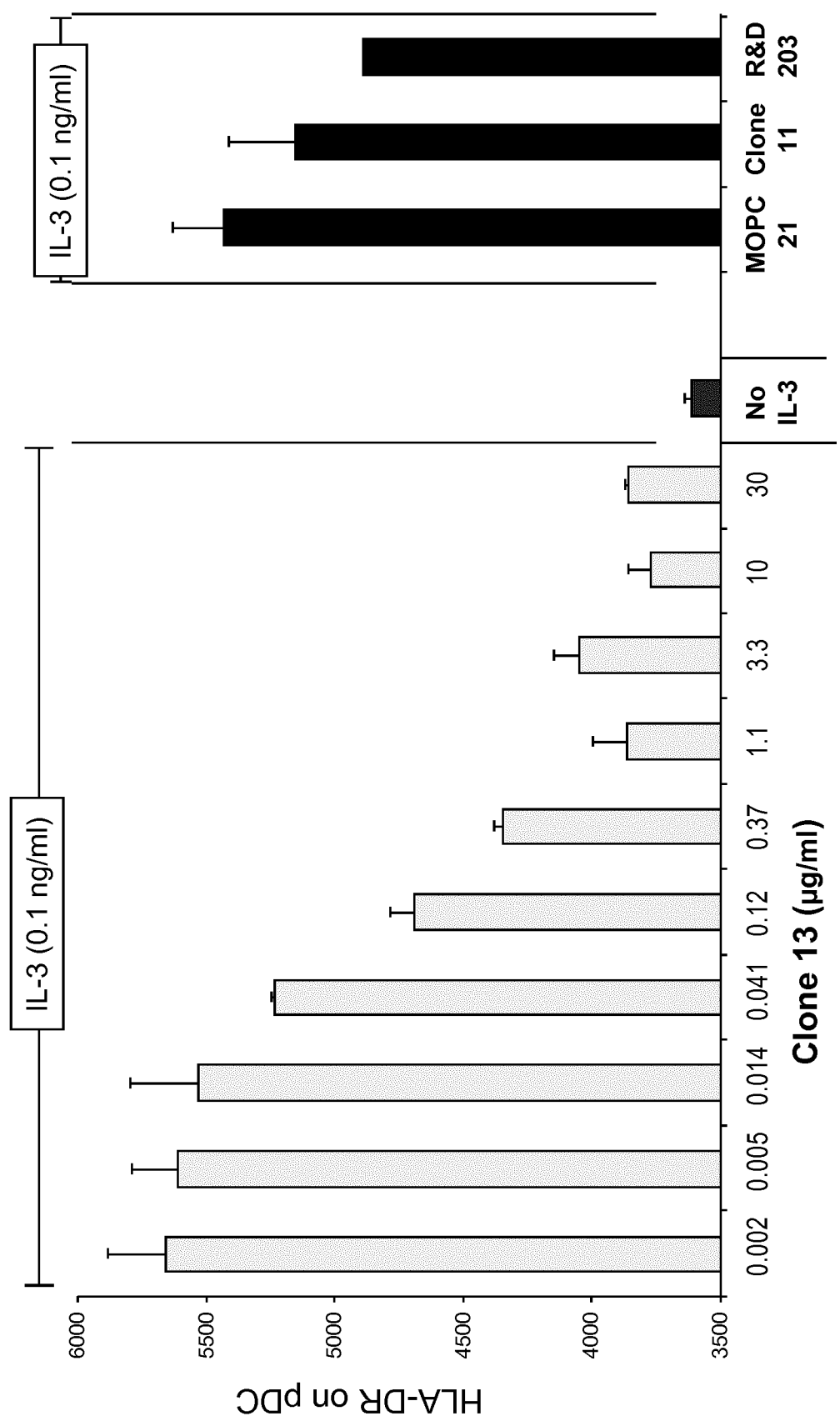

FIG. 26 shows blockage of IL-3 induced upregulation of HLA-DR on pDCs by clone 13.

IL-3 (0.1 ng/ml) was preincubated with various concentrations of the IL-3 antibody clone 13 or with 10 µg/ml of MOPC-21 (mouse IgG1 isotype control antibody), clone 11 or R&D mab 203 (clone 4806) for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of HLA-DR on plasmacytoid dendritic cells (pDC).

Figure 27:
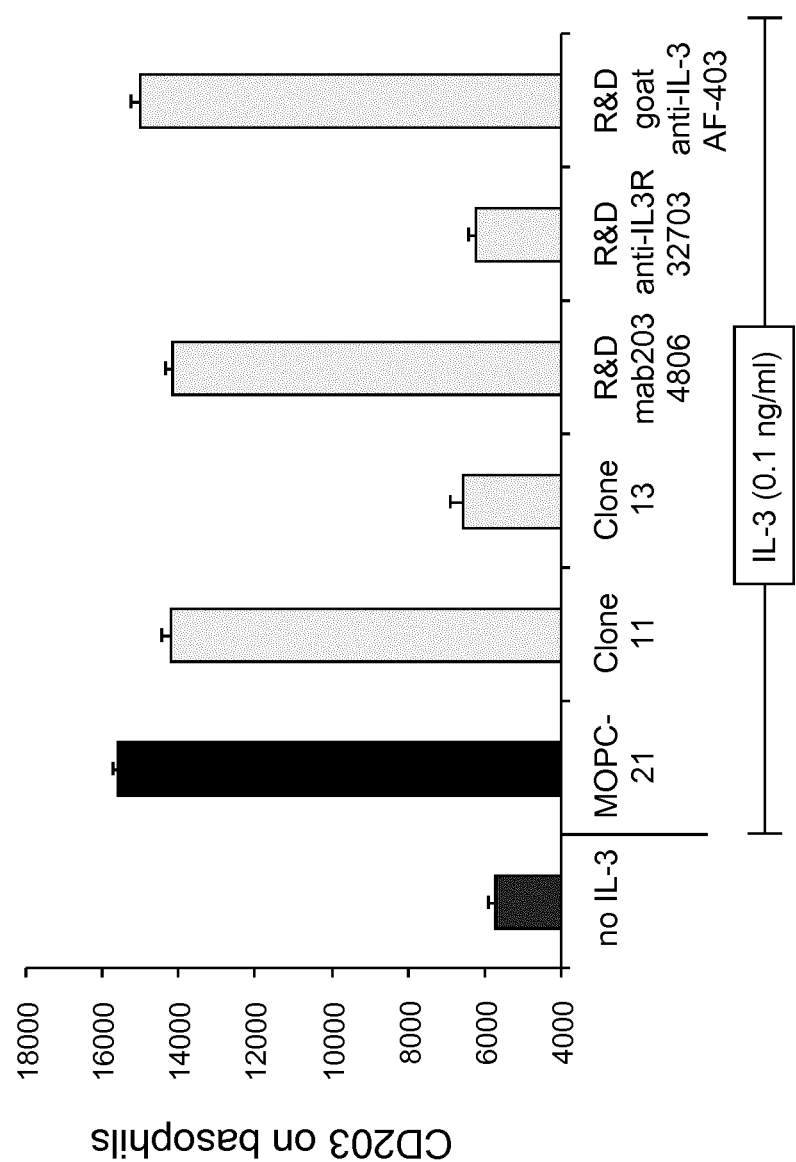

FIG. 27 shows the effects of antibodies on IL-3 induced upregulation of CD203c on basophils.

IL-3 (0.1 ng/ml) was preincubated with antibodies (10 µg/ml) for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

MOPC-21=mouse IgG1 kappa isotype control antibody. Clone 11, 13, 36, 4806=anti-human IL-3 antibodies.

Figure 28:
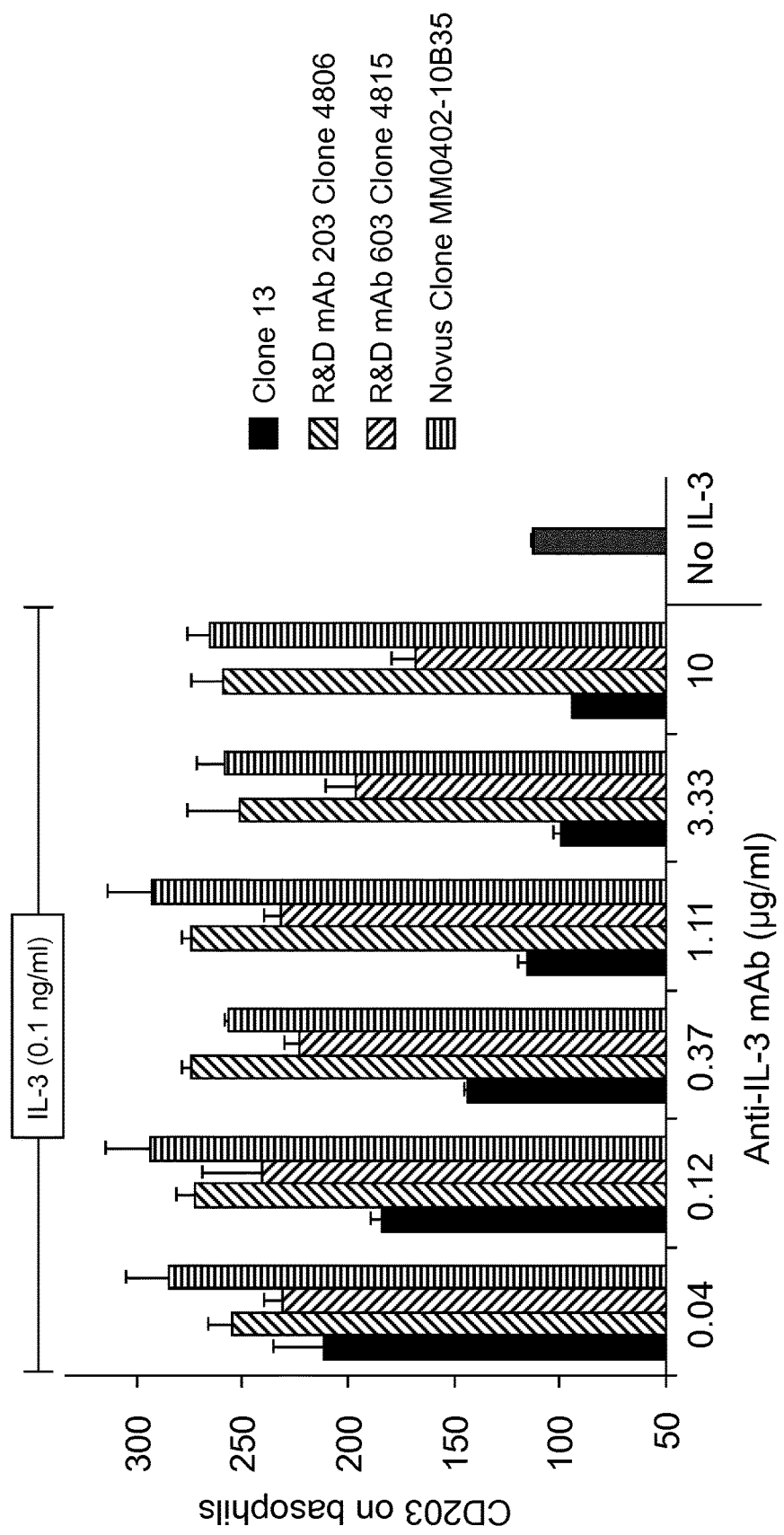

Clone 32703=anti-human IL-3 receptor antibody. AF-403=polyclonal goat anti-human IL-3 from R&D Systems FIG. 28 shows the effects of antibodies on IL-3 induced upregulation of CD203c on basophils.

IL-3 (0.1 ng/ml) was preincubated with various concentrations of anti-IL-3 antibodies for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 29:
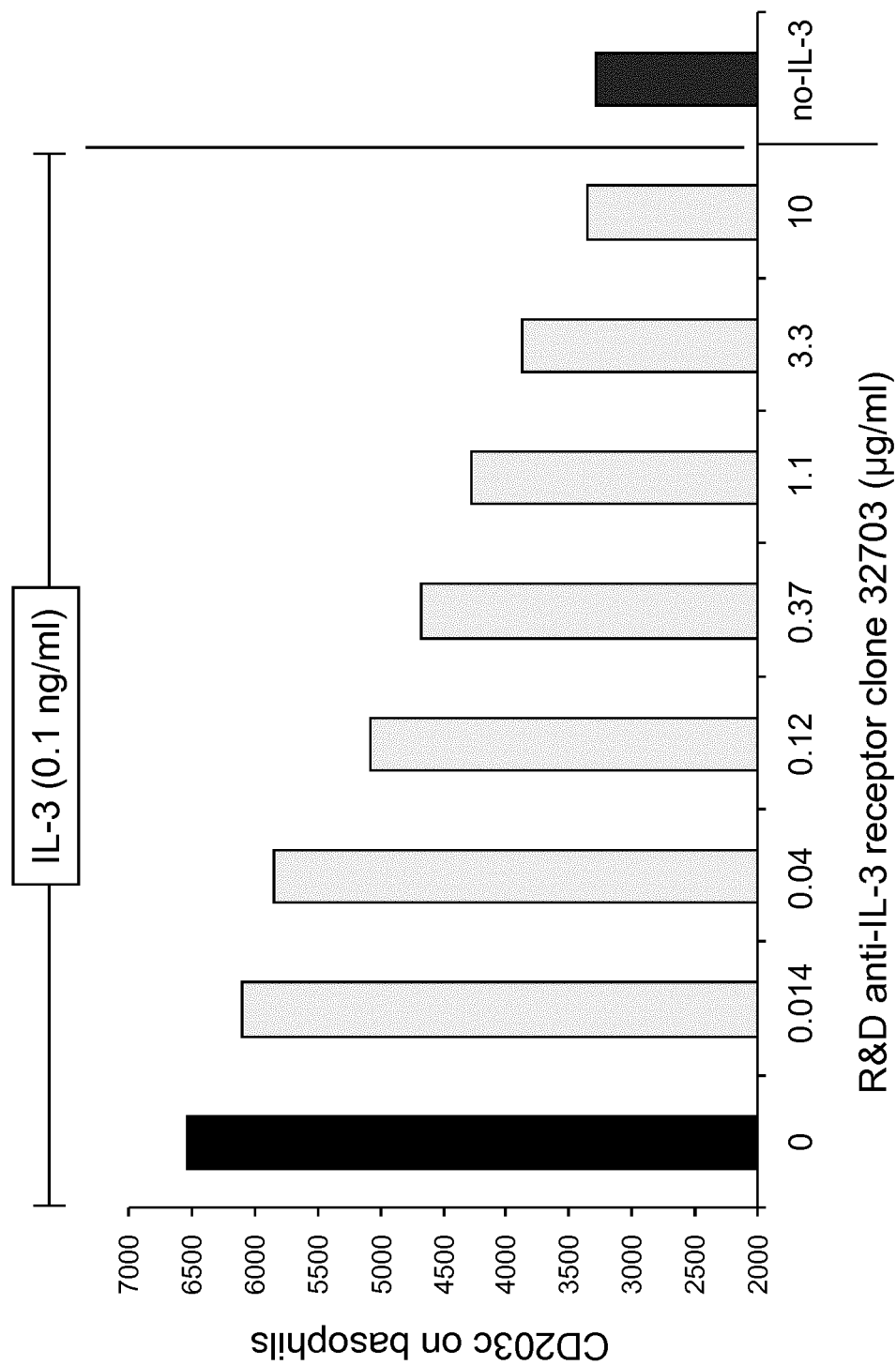

FIG. 29 shows the blocking effects of R&D anti-IL-3 receptor clone 32703 on IL-3 induced upregulation of CD203c on basophils.

Fresh human EDTA blood was preincubated with various concentrations of the anti-IL-3 receptor clone 32703 (for 20 min at room temperature. Without washing IL-3 (0.1 ng/ml) was added and incubated for 1 h at 37° C. Cells were stained with directly labelled antibodies against CD11b, CD203c, CD123 and HLA-DR for 20 min on ice and analyzed by flow cytometry to identify basophils and to quantify upregulation of CD203c on basophils.

The results shown in FIGS. 17 to 29 were obtained by using human IL-3 expressed by insect cells (Recombinant Human IL-3 (carrier-free) Cat. #578002 from Biolegend). Therefore the human IL-3 peptide was glycosylated.

Figure 30:
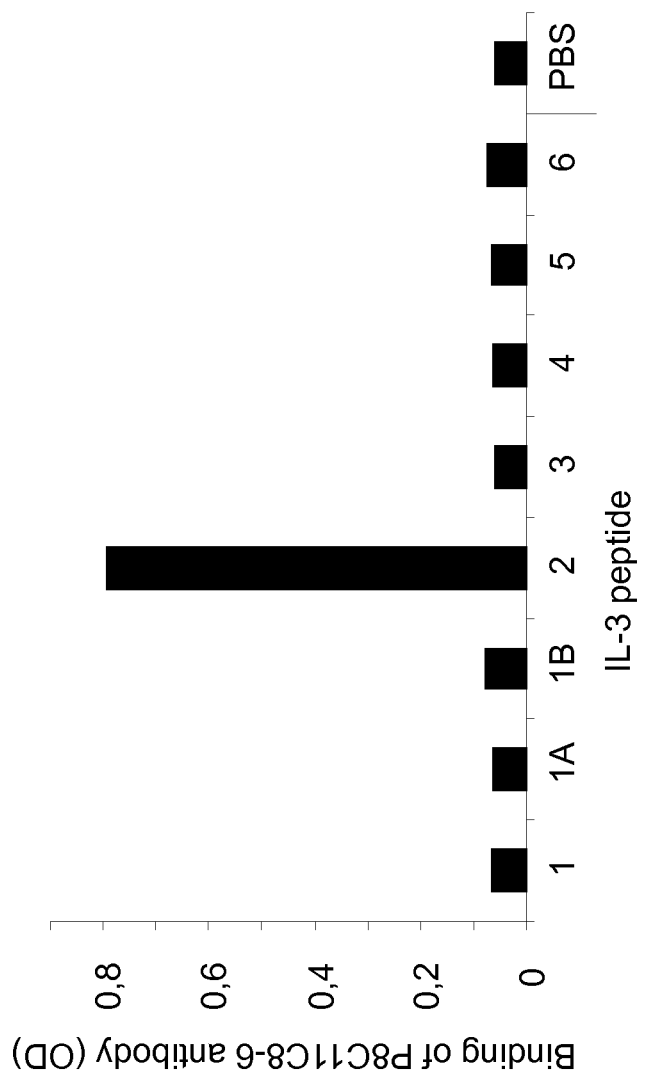
Figure 31:
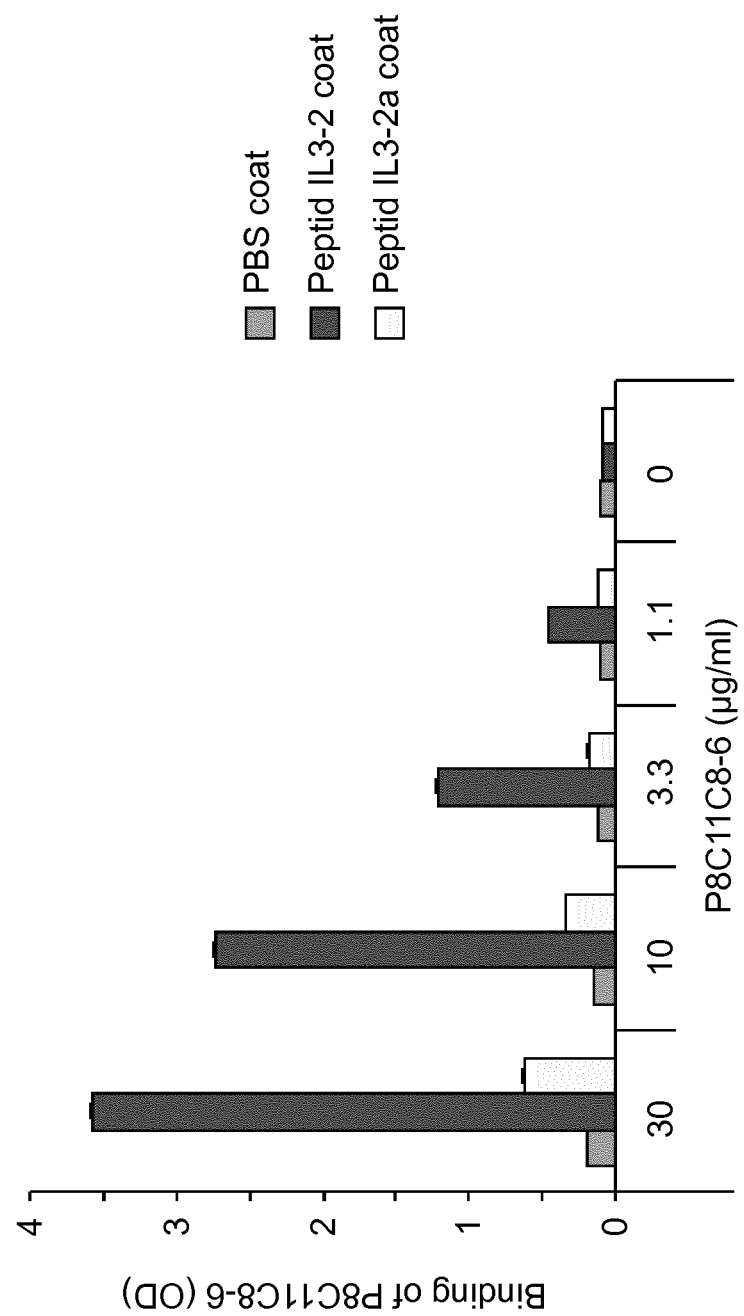

FIGS. 30 and 31A and 31B show binding of P8C11C8-6 to various peptides derived from human IL-3. The epitope recognized by P8C11C8-6 includes amino acids 27-29 (LKQ). It is located within amino acids 22-48 and it seems that some or all of amino acids 26 (H) to 36 (D) of the amino acid sequence as defined in SEQ ID NO:10 are involved in binding.

Figure 32:
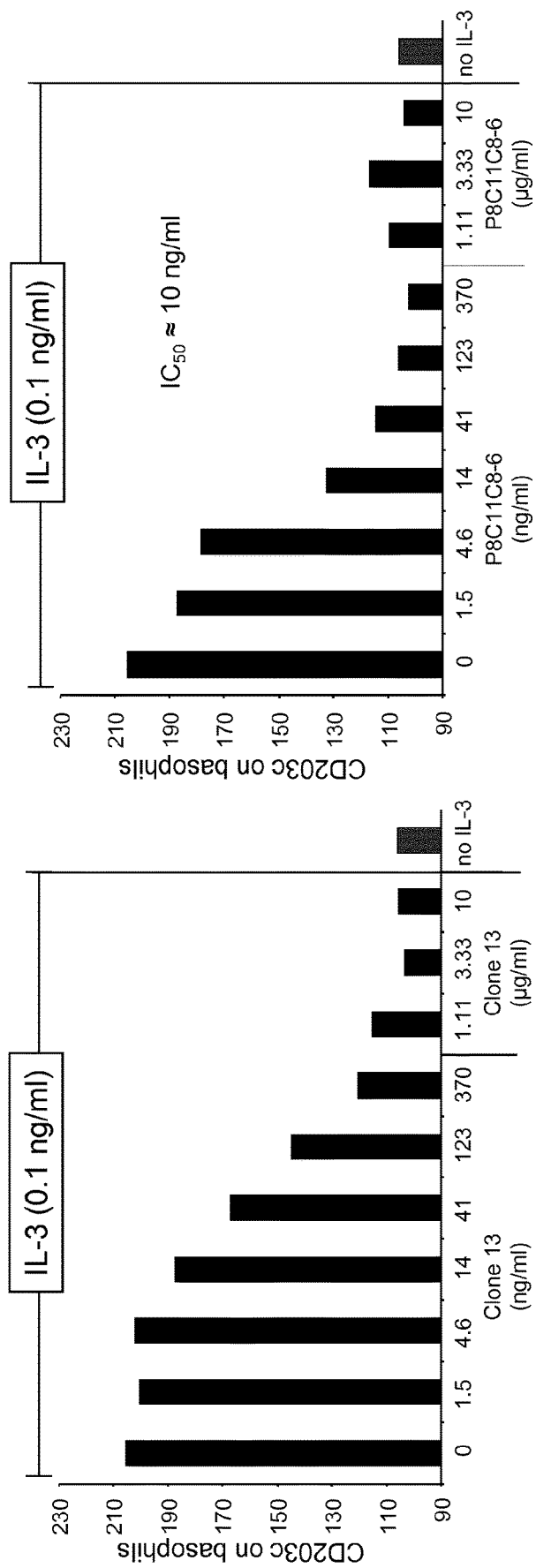
Figure 33:
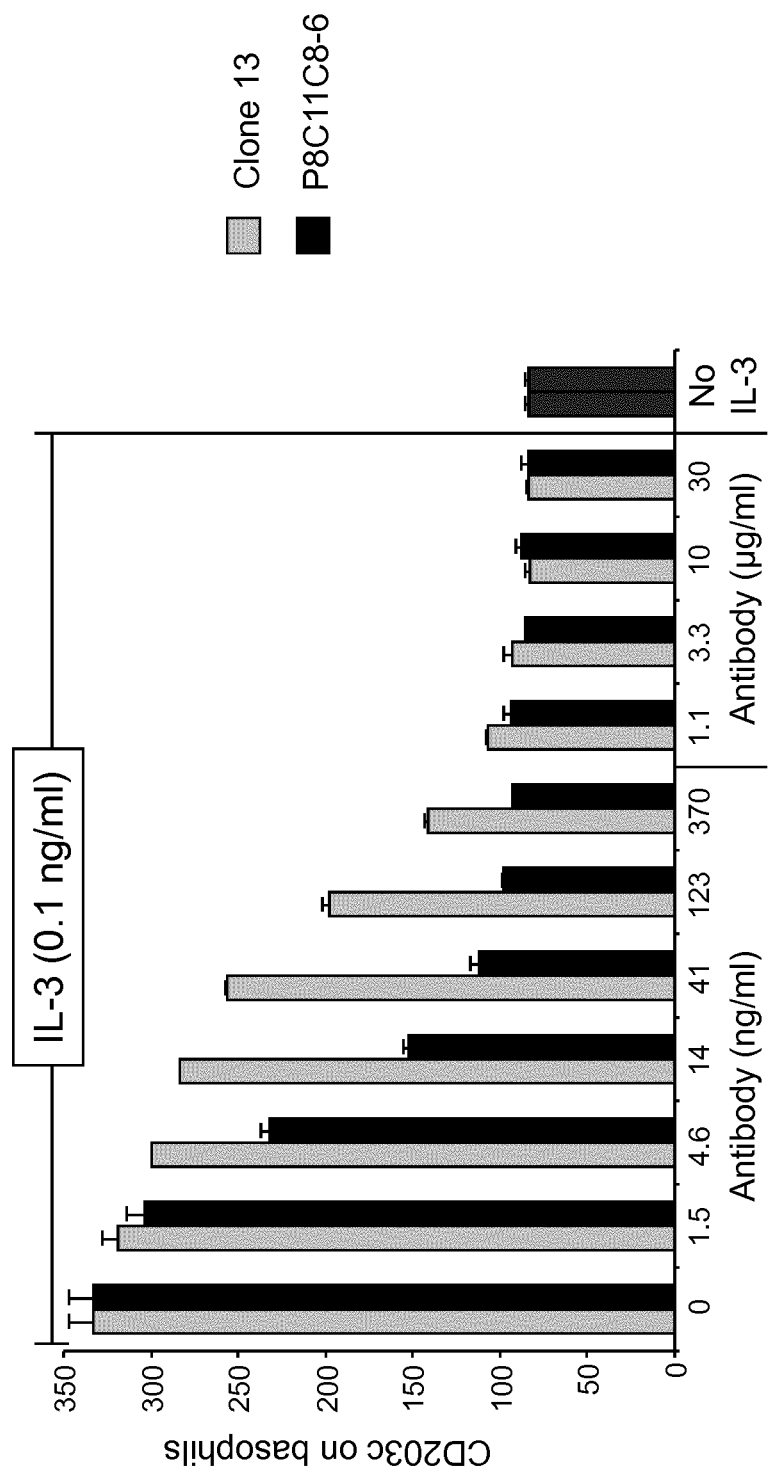

FIGS. 32 and 33 show blockage of IL-3 induced upregulation of CD203c on basophils by clone 13 and clone P8C11C8-6.

IL-3 (0.1 ng/ml) was preincubated with various concentrations of anti-IL-3 antibodies for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify upregulation of CD203c on basophils.

Figure 34:
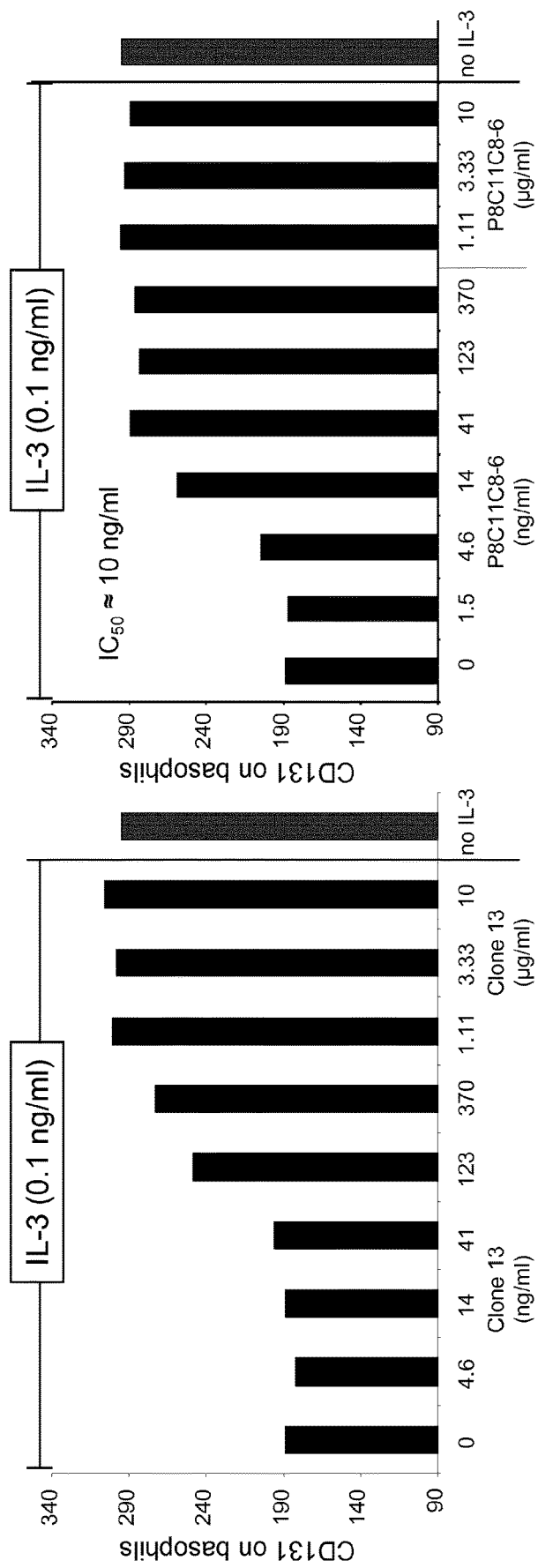
Figure 35:
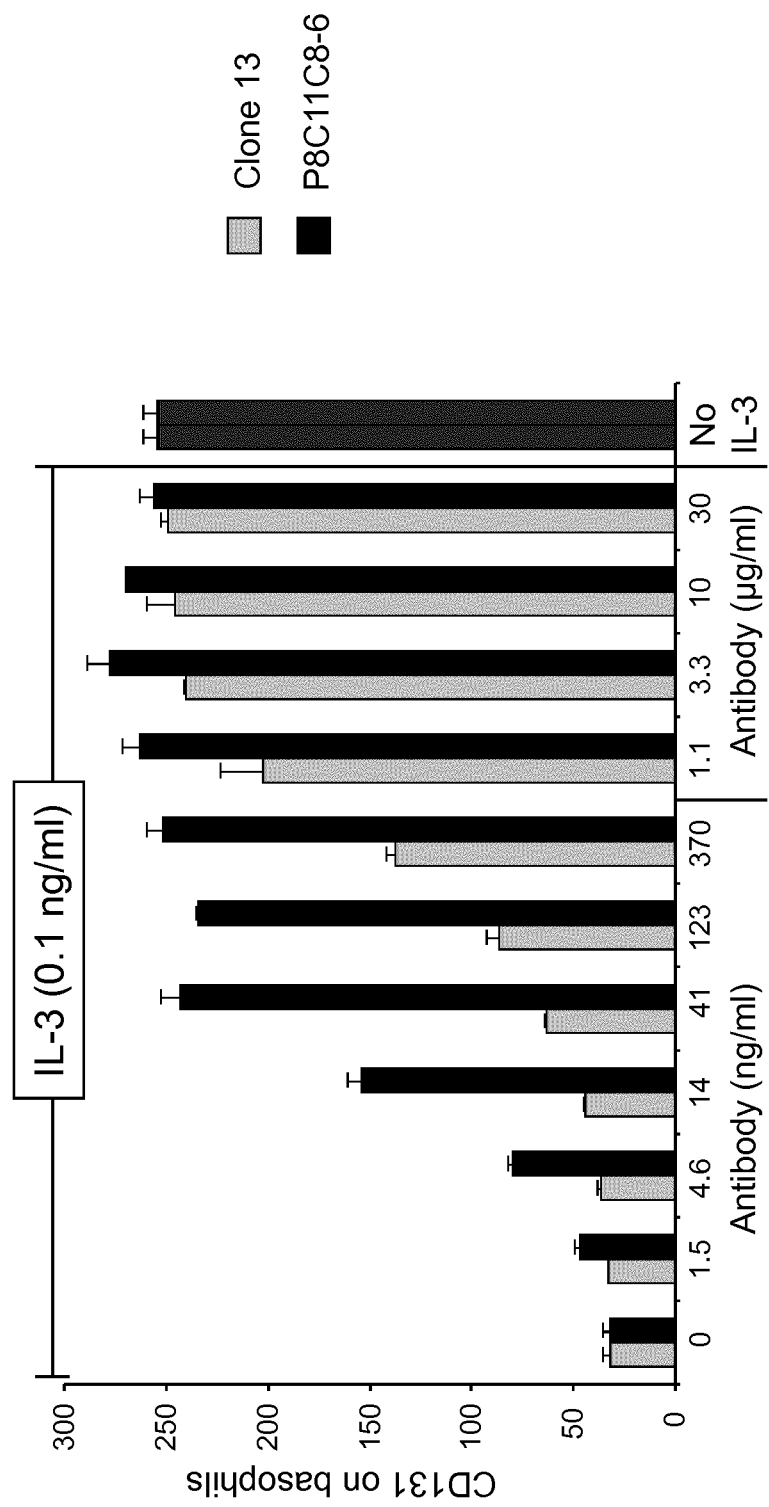

FIGS. 34 and 35 show blockage of IL-3 induced downregulation of CD131 on basophils by clone 13 and clone P8C11C8-6.

IL-3 (0.1 ng/ml) was preincubated with various concentrations of anti-IL-3 antibodies for 20 min at room temperature and added to fresh human EDTA blood. After 1 h incubation at 37° C. cells were stained with directly labelled antibodies against CD11b, CD203c, CD123 and HLA-DR for 20 min on ice and analyzed by flow cytometry to identify basophils and to quantify downregulation of CD131 on basophils.

Figure 36:
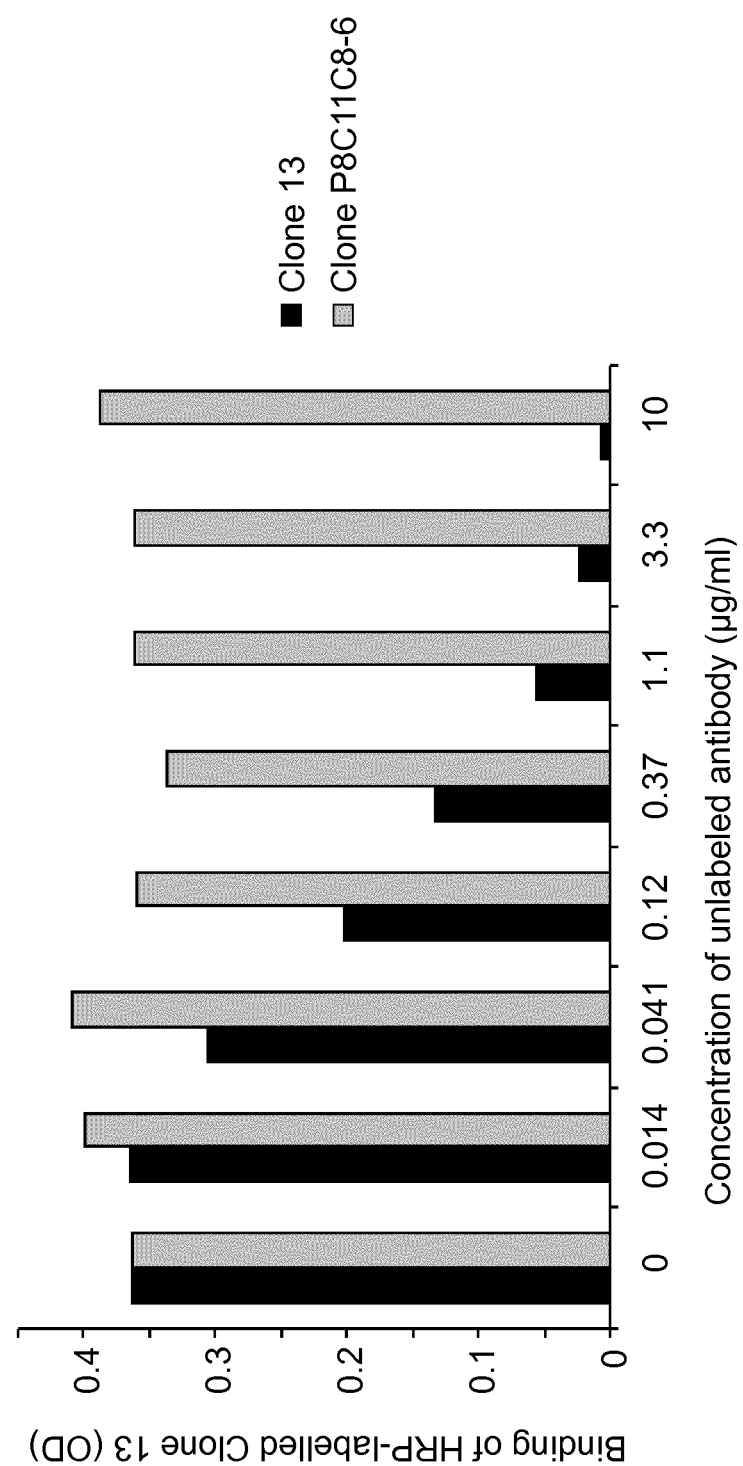

FIG. 36 shows that clone 13 and clone P8C11C8-6 do not bind to the same epitope of IL-3.

Figure 37:
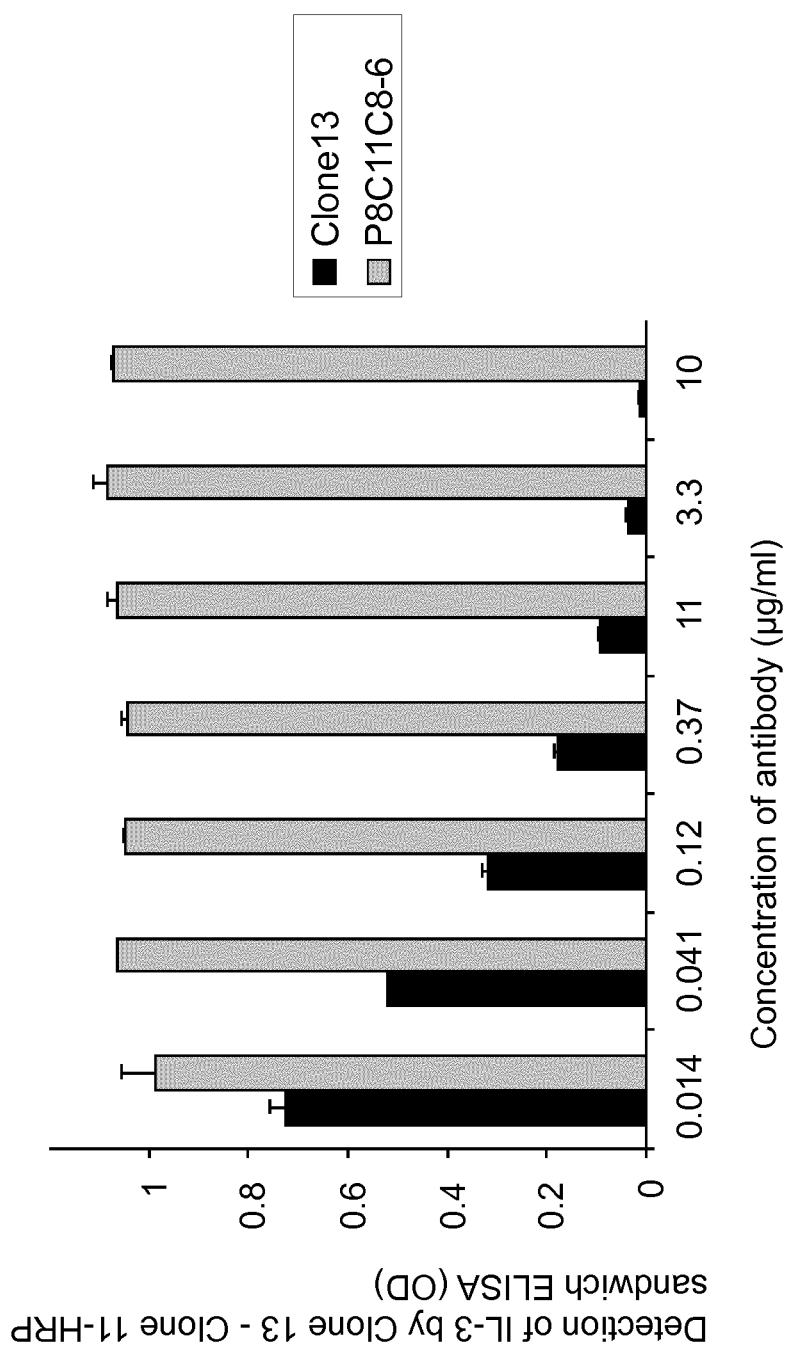

FIG. 37 shows that P8C11C8-6 does not interfere with the binding of clone 13 or clone 11 to IL-3.

Figure 38:
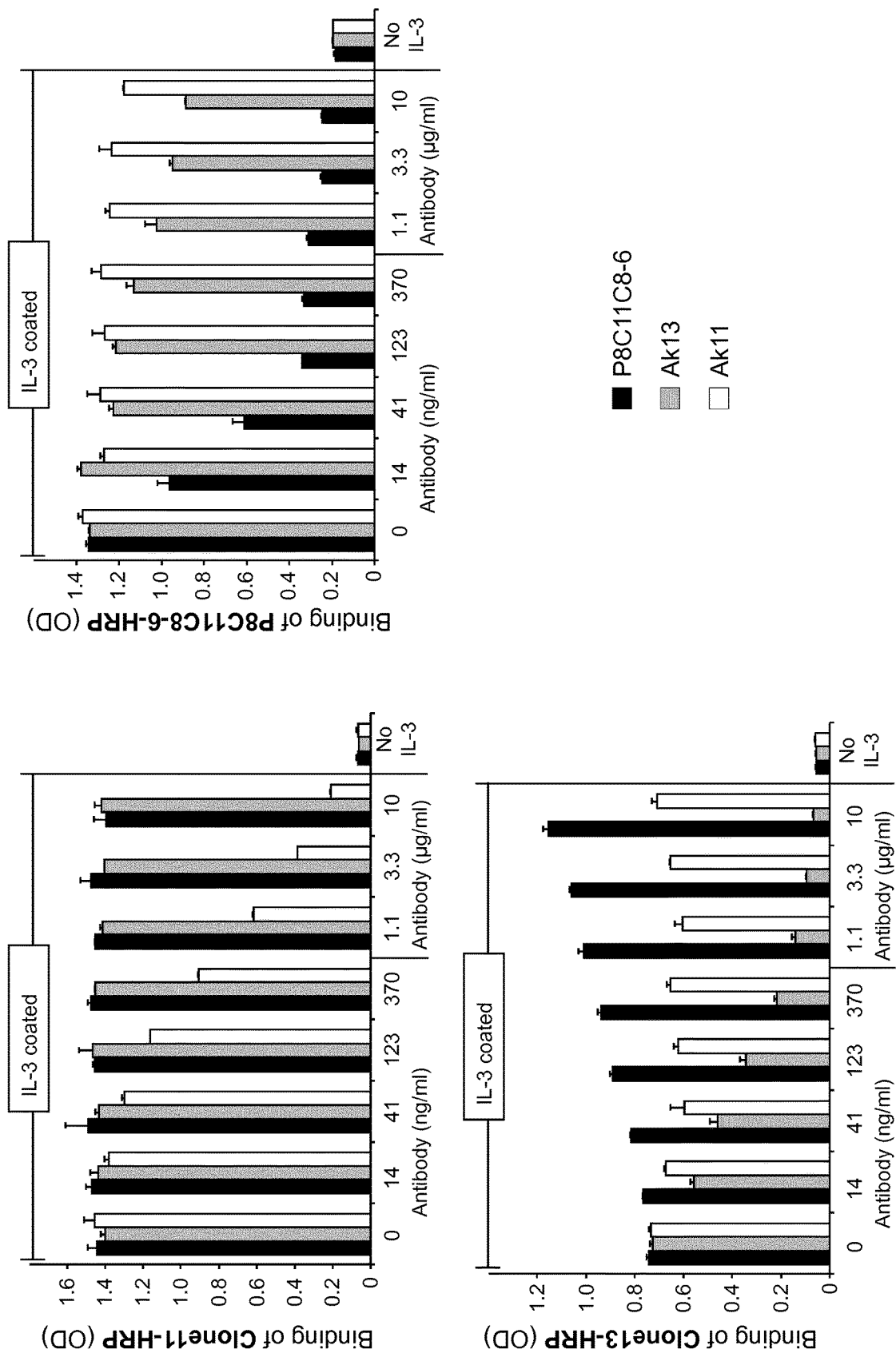

FIG. 38 shows that P8C11C8-6 does not prevent binding of clone 13 (AK13) or clone 11 (AK11) to IL-3.

The results shown in FIGS. 32 to 38 were obtained by using human IL-3 expressed by insect cells (Recombinant Human IL-3 (carrier-free) Cat. #578002 from Biolegend). Therefore the human IL-3 peptide was glycosylated.

Figure 39:
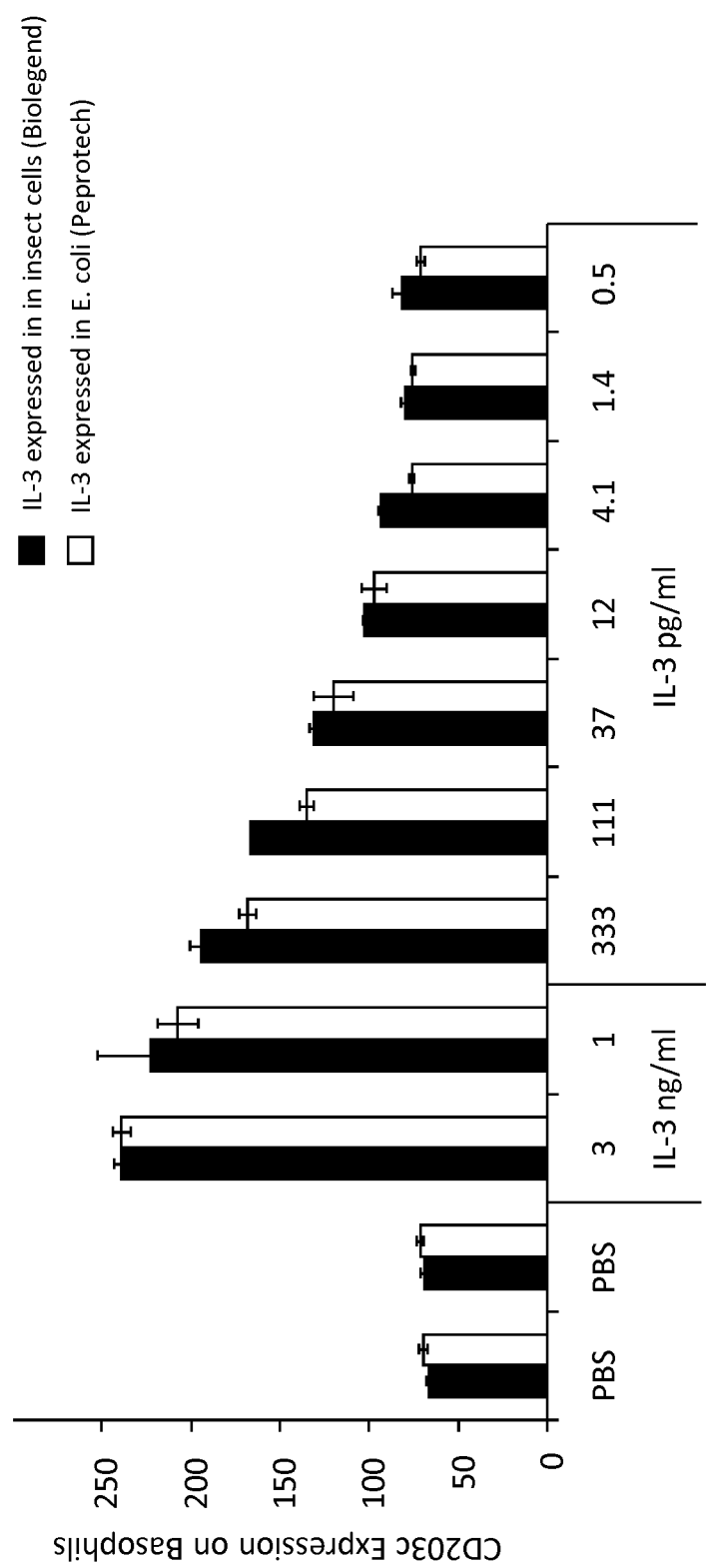

FIG. 39 shows the comparable activity of *E. coli* or insect cell derived IL-3 on human basophils.

Figure 40:
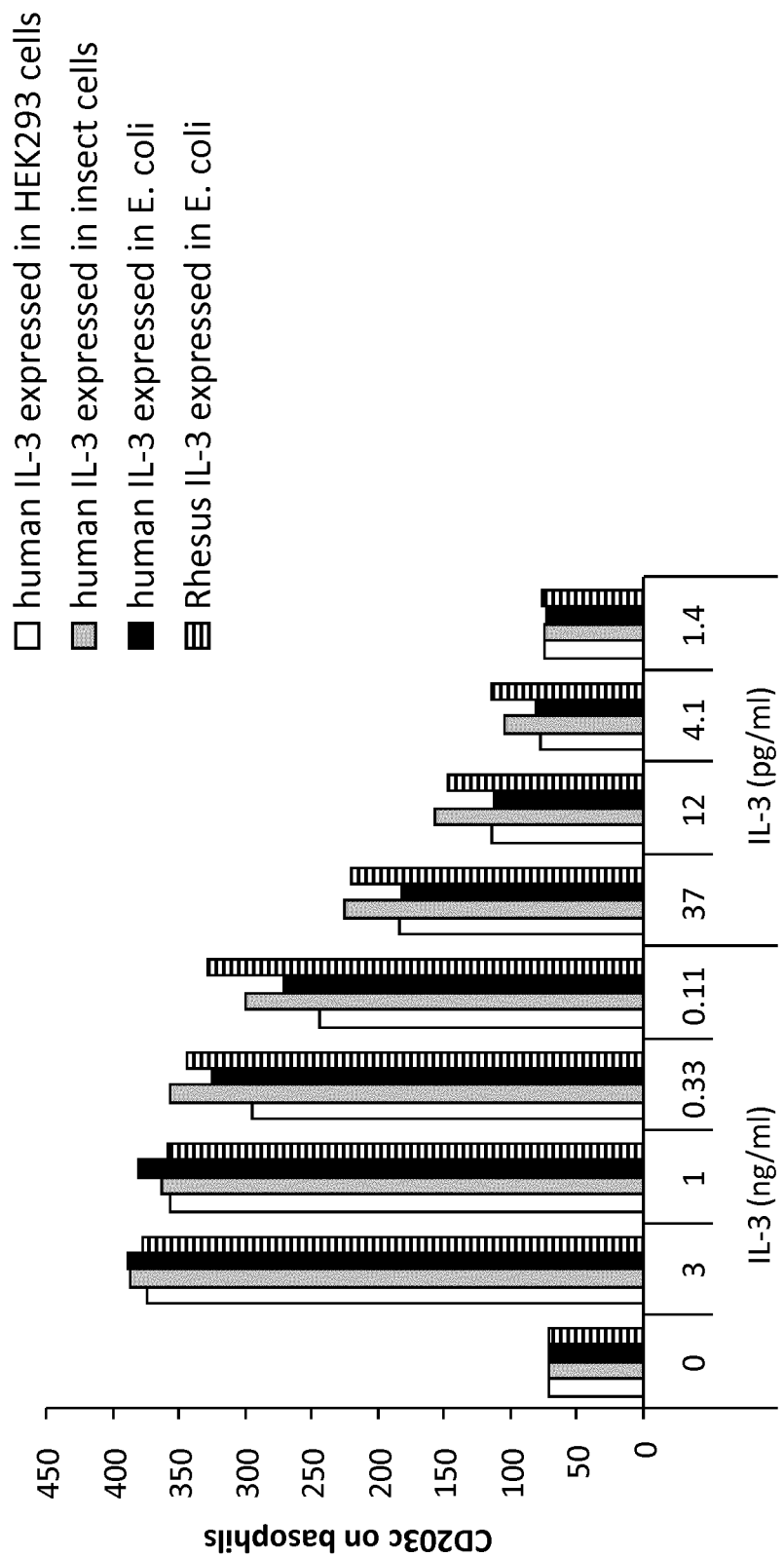

FIG. 40 shows the similar activity of IL-3 from various sources in a bioassay with human basophils.

Figure 41:
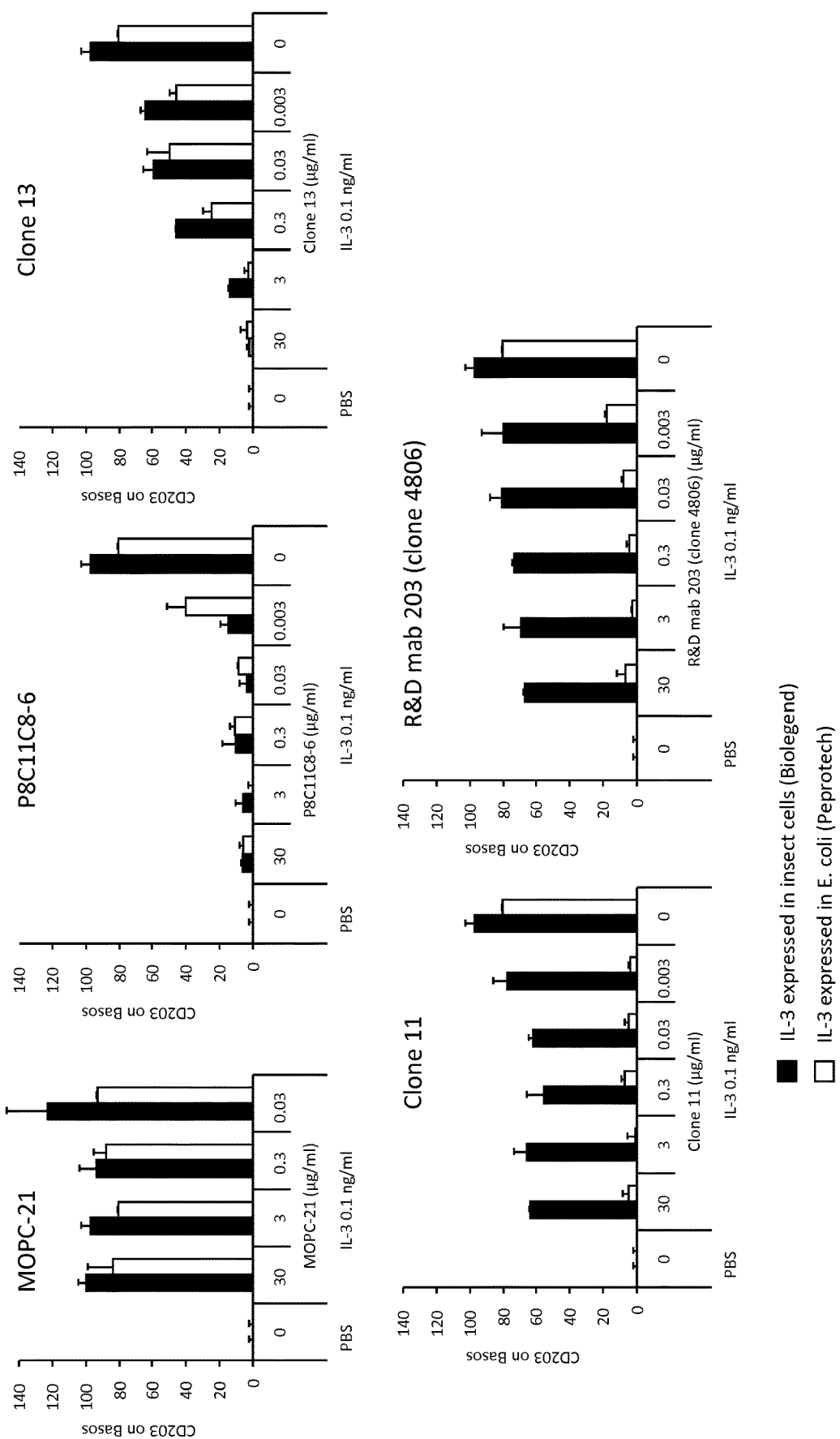

FIG. 41 shows that Clone 11 and R&D mab 203 only block the activity of *E. coli* derived IL-3, but not the activity of insect cell or HEK293 cell derived IL-3 in an assay with basophils.

Figure 42:
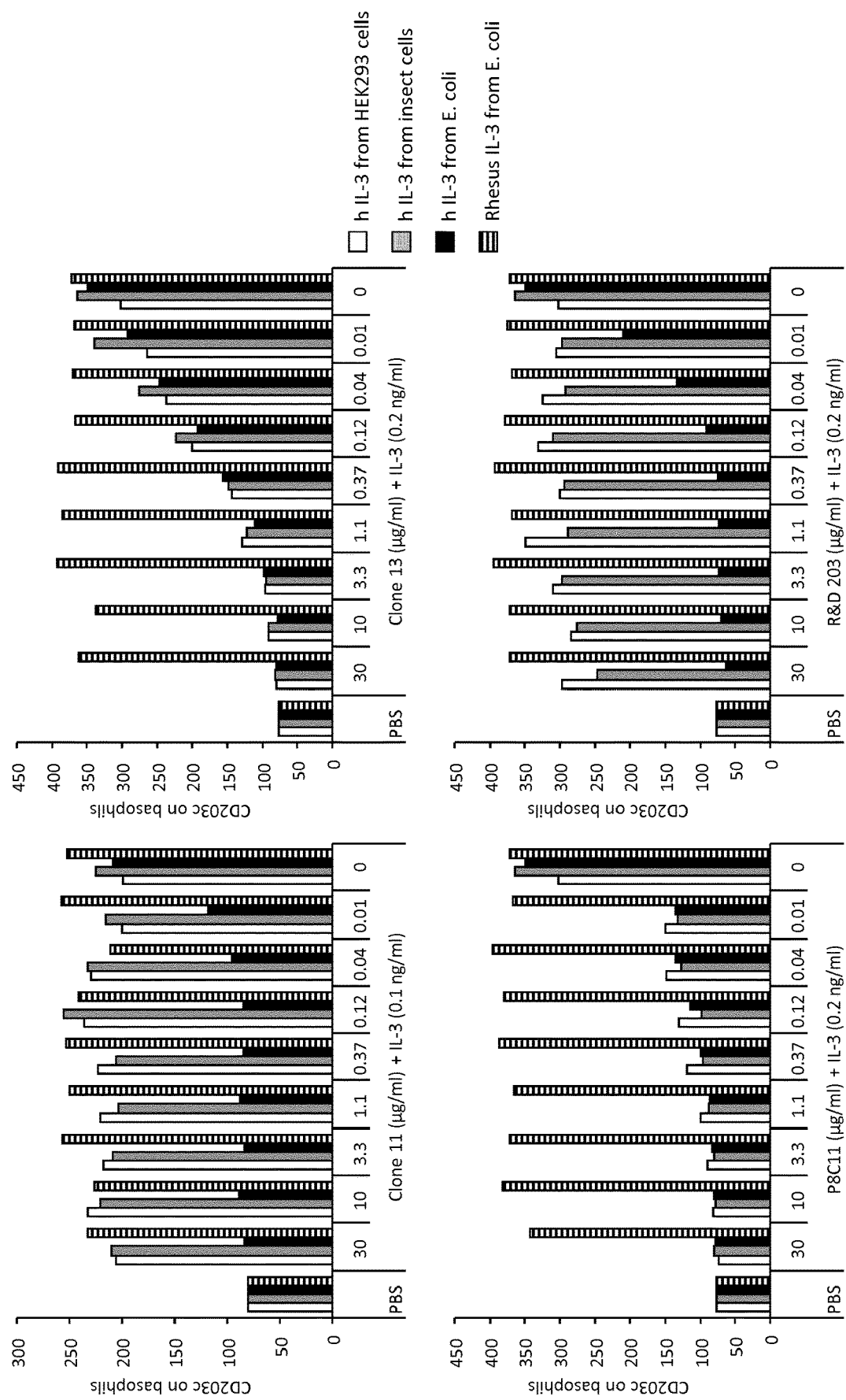

FIG. 42 shows that clone 11 and R&D mab 203 only block the activity of *E. coli* derived IL-3, but not the activity of insect cell derived IL-3 in an assay with basophils.

Figure 43:
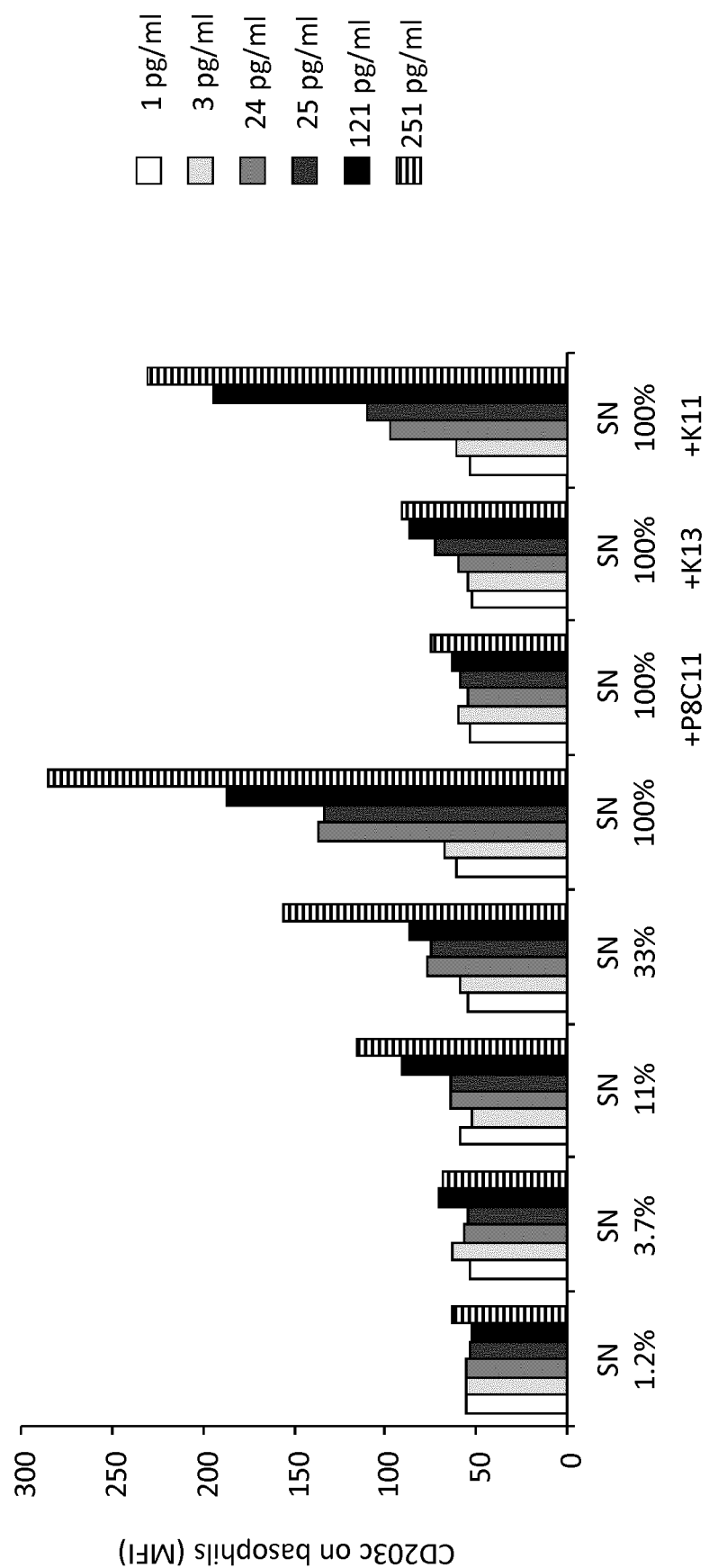

FIG. 43 shows that clone 13 and P8C11C8-6 block bioactivity of IL-3 released by primary T cells from RA-patients and that Clone 11 has little inhibitory activity.

Figure 44:
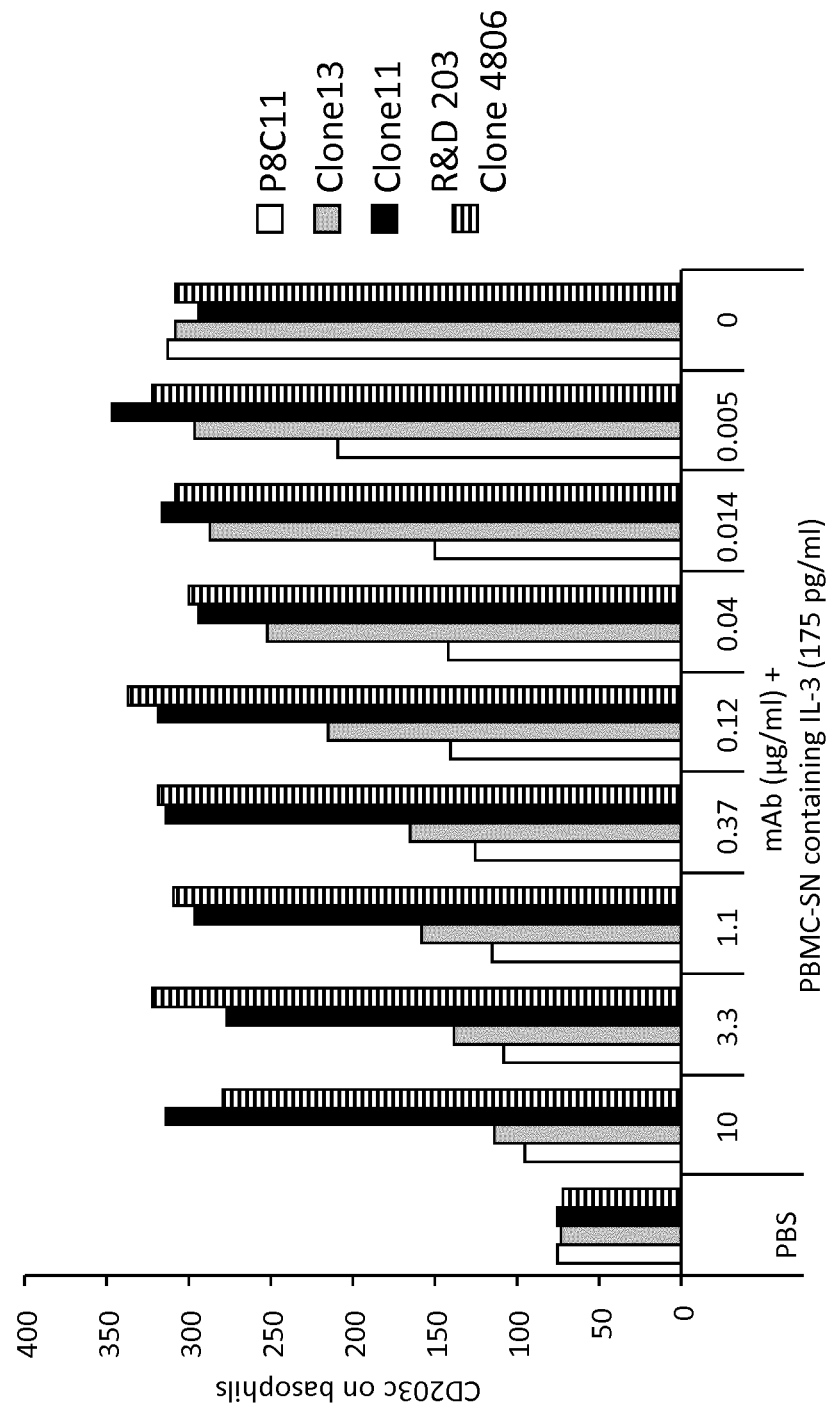

FIG. 44 shows that clone 13 and P8C11C8-6 block bioactivity of IL-3 produced by human PBMC and that Clone 11 and R&D mab203 have little inhibitory activity.

Figure 45:
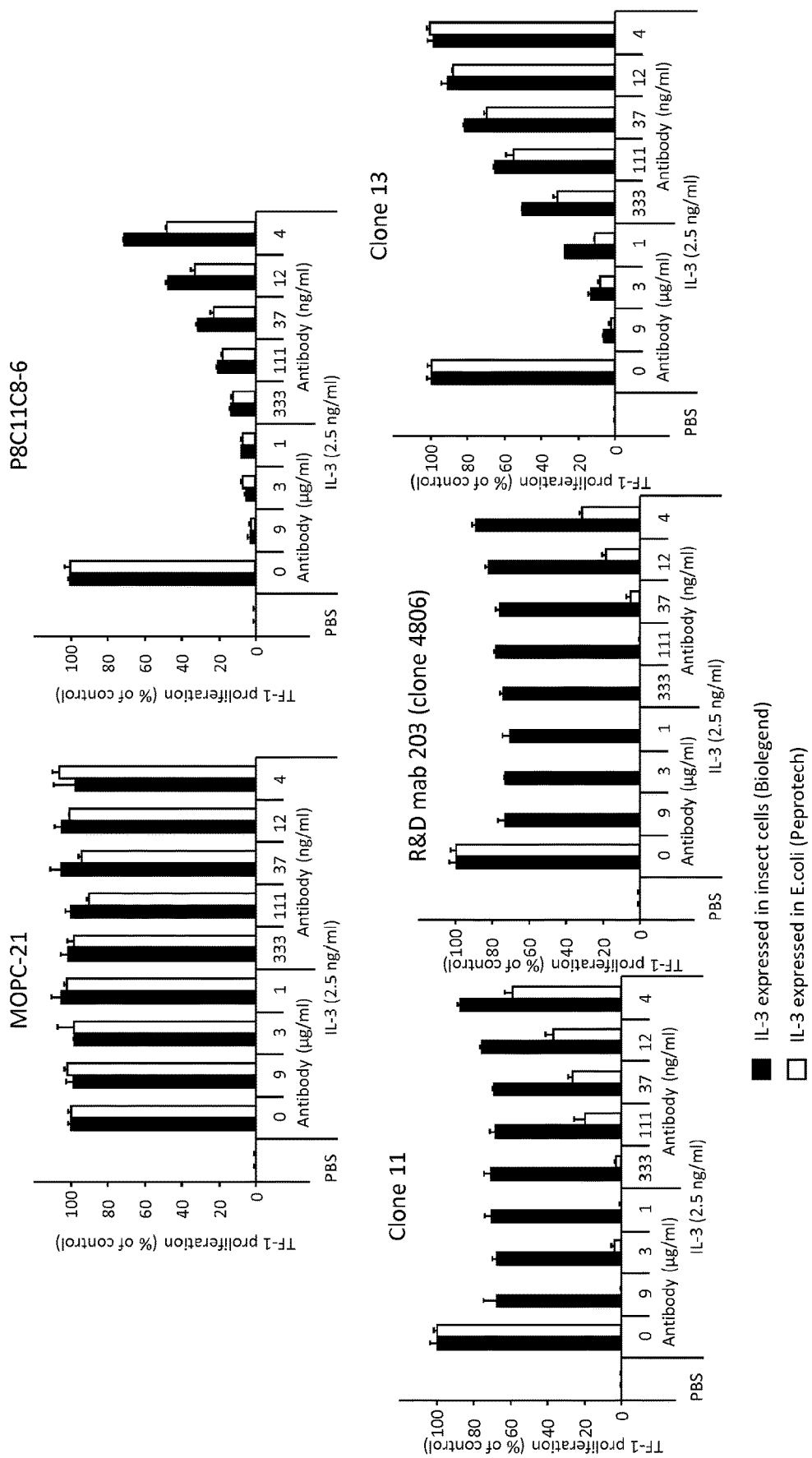

FIG. 45 shows that clone 11 and R&D mab 203 only block the activity of *E. coli* derived IL-3, but not the activity of insect cell derived IL-3 in the TF-1 assay.

Figure 46:
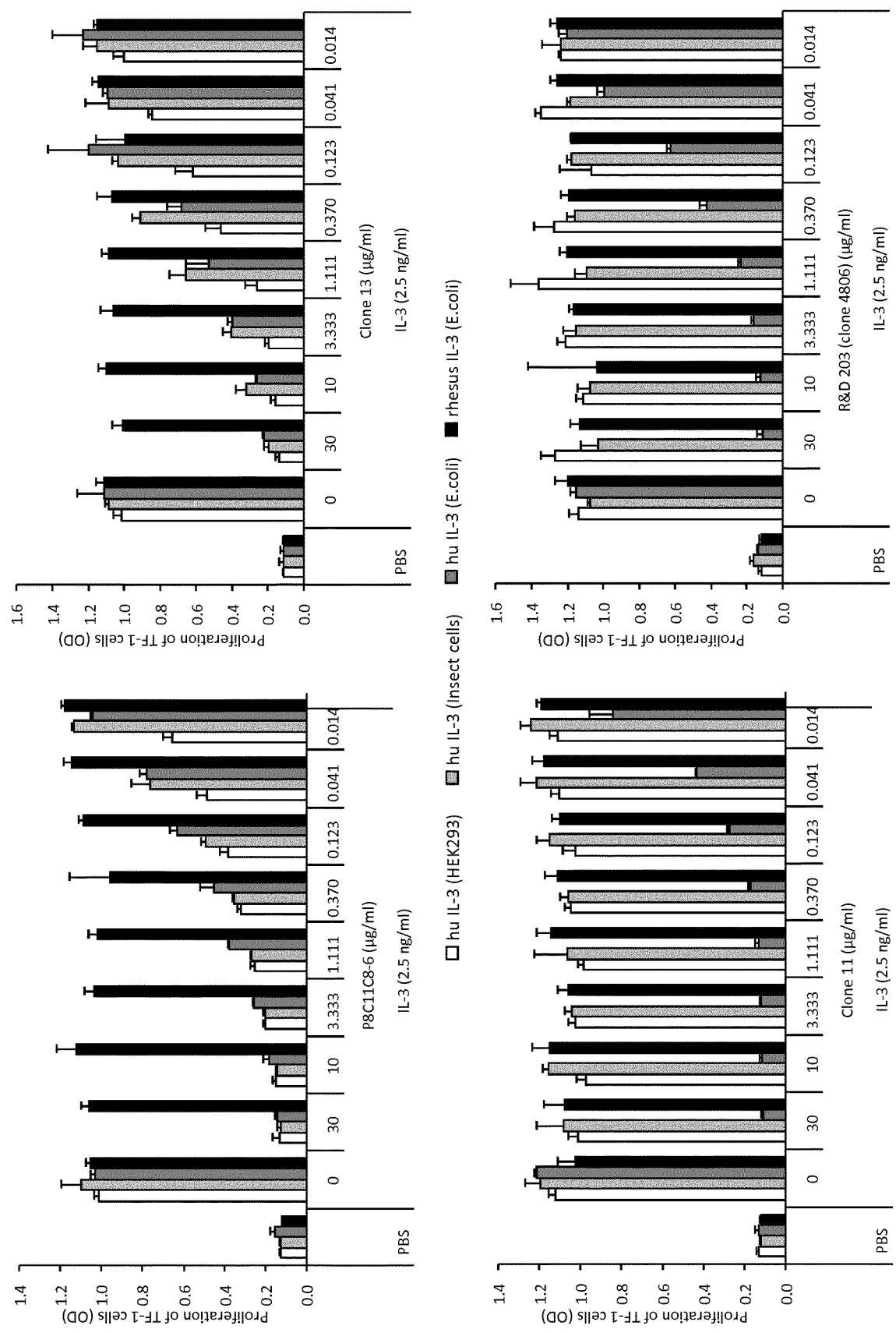

FIG. 46 shows that clone 11 and R&D mab 203 only block the activity of *E. coli* derived IL-3, but not the activity of IL-3 from insect cells or HEK293 cells in the TF-1 assay; and that Rhesus IL-3 is not blocked by the antibodies.

Figure 47:
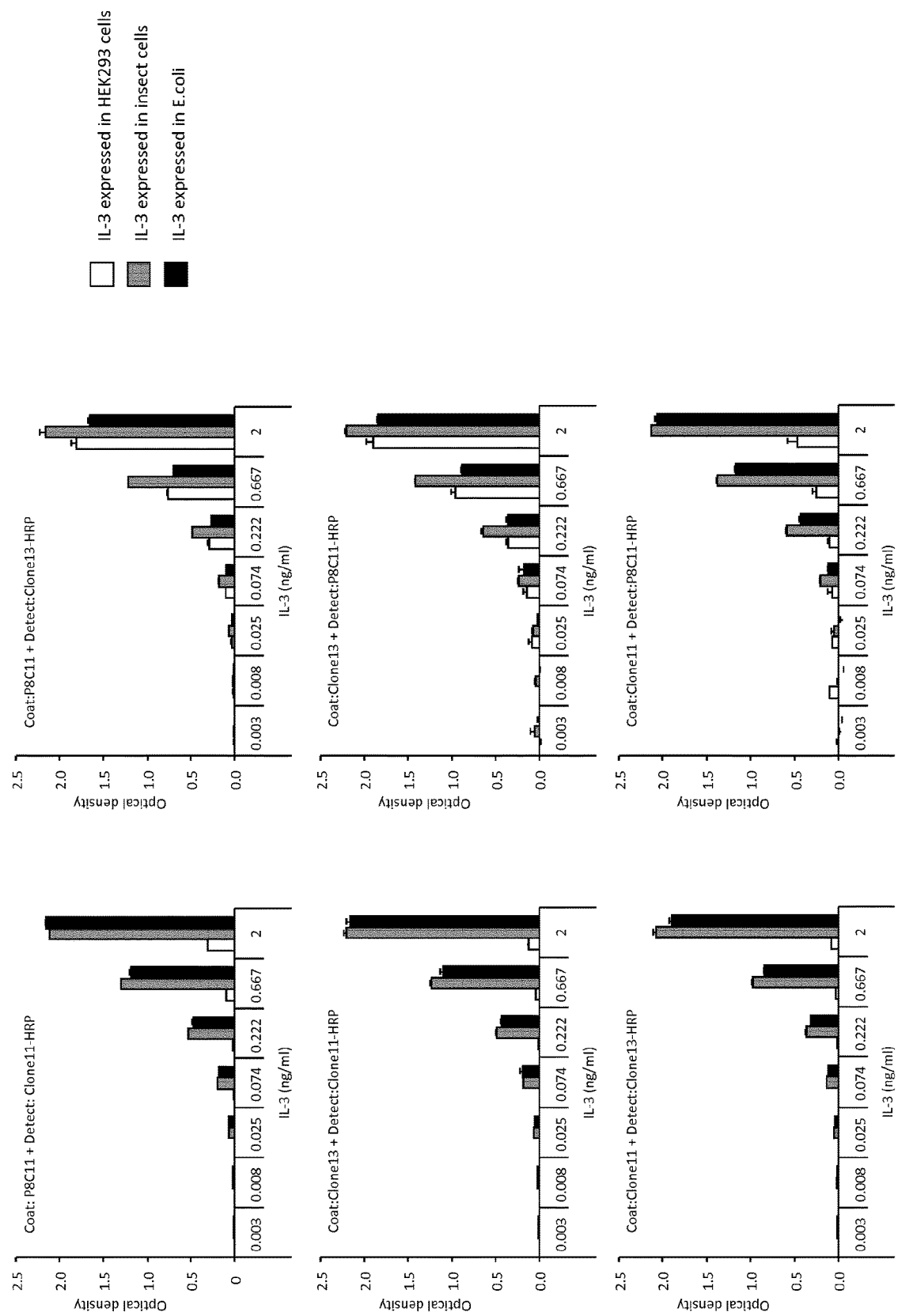

FIG. 47 shows the detection of IL-3 from various sources by sandwich ELISA and that only the pair of clone13+ P8C11C8-6 detects IL-3 expressed in HEK293 cells.

Figure 48:
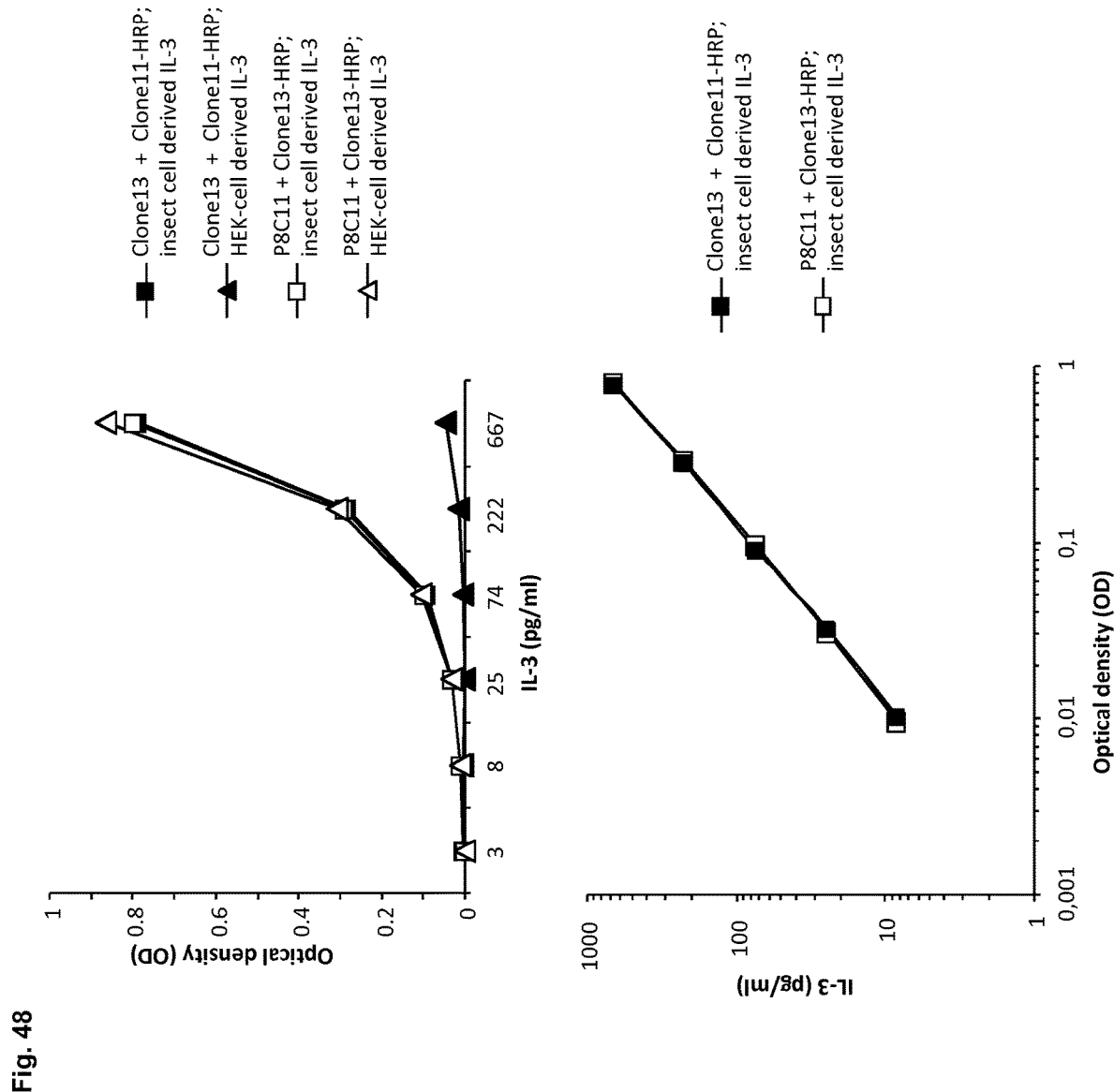

FIG. 48 shows the detection of IL-3 from various sources by two different sandwich ELISAs and the standard curves for quantification of IL-3 (lower diagram in FIG. 48).

Figure 49:
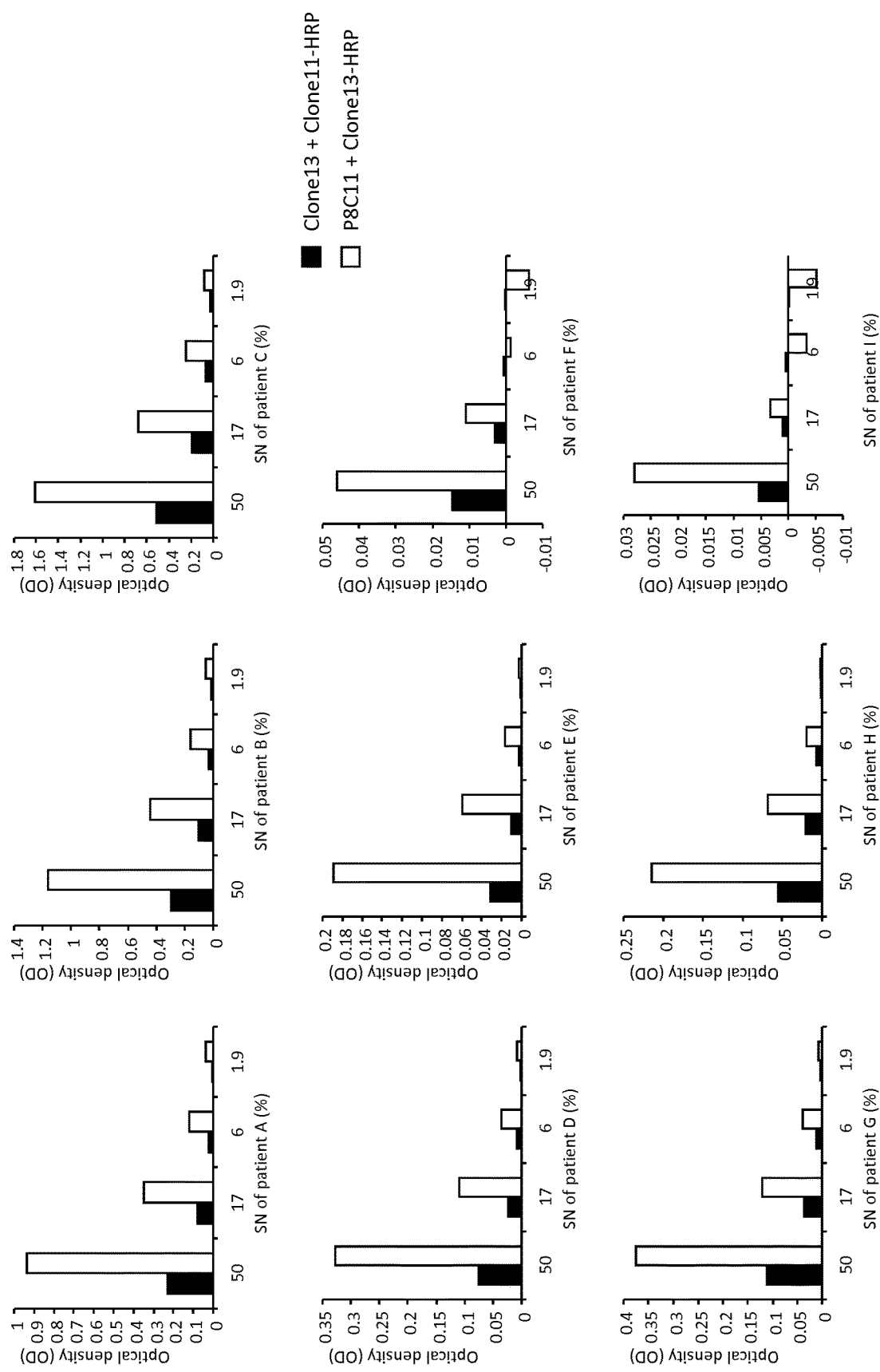

FIG. 49 shows the detection of IL-3 produced by human PBMC using two different sandwich ELISAs.

Figure 50:
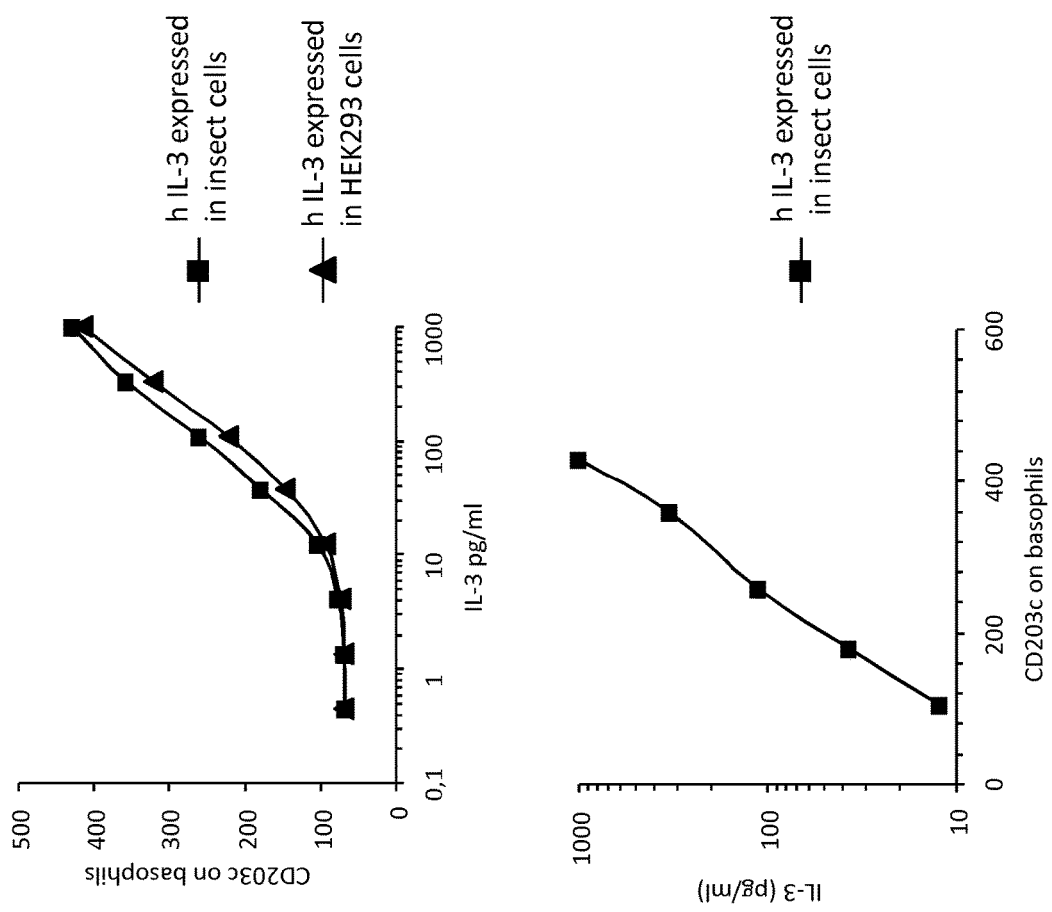

FIG. 50 shows the result of a bioassay with human basophils for detection of IL-3 from various sources and the standard curve for quantification of IL-3 bioactivity (in lower diagram of FIG. 50).

Figure 51:
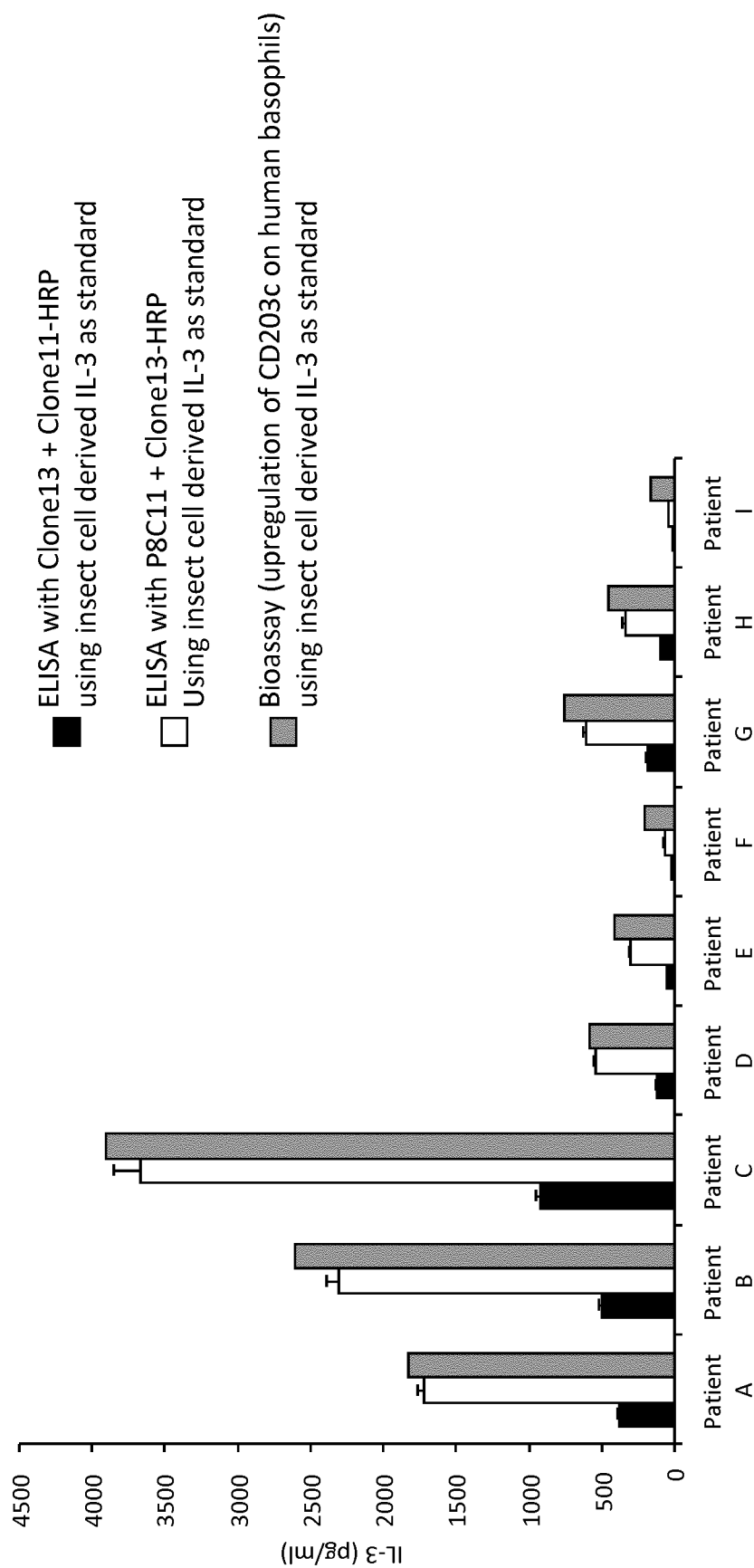

FIG. 51 shows the quantification of human PBMC derived IL-3 with ELISAs and Bioassay and that the Quantification of IL-3 with ELISA (P8C11C8-6+Clone13-HRP) correlates very well with the bioactivity of human PBMC-derived IL-3. Insect derived IL-3 was used as standard.

Figure 52:
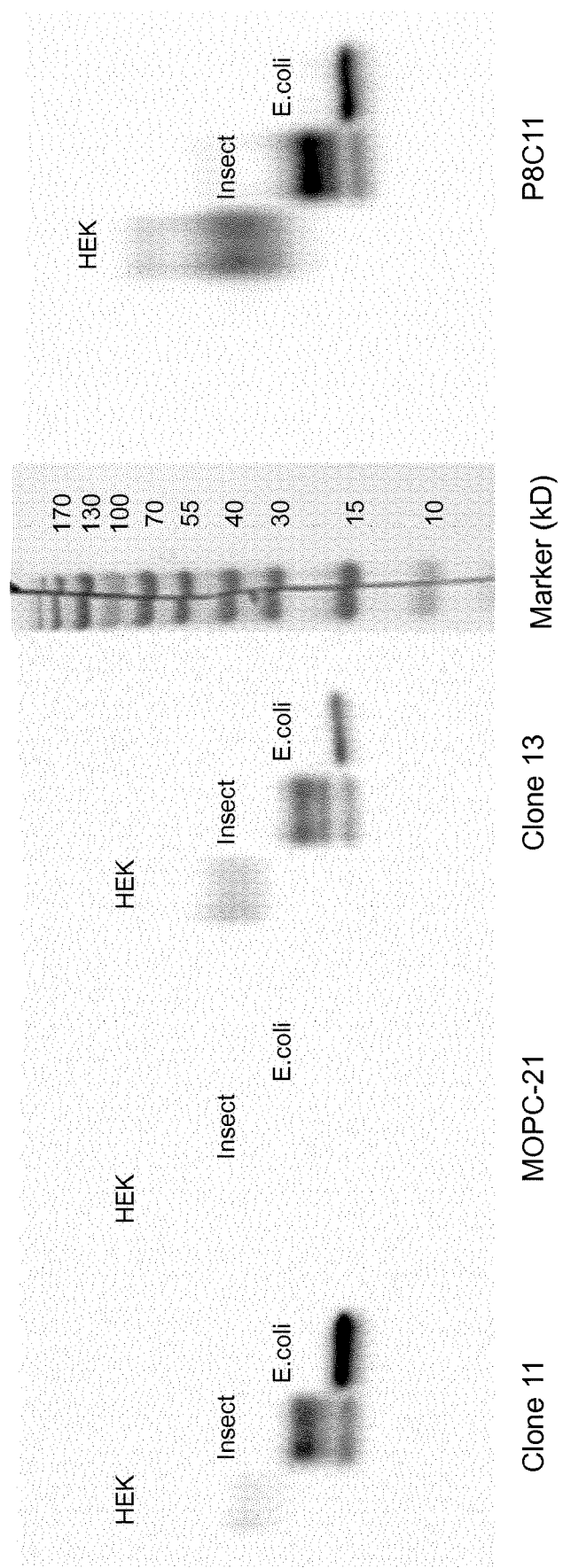

FIG. 52 provides a Western blot showing the difference in molecular weight caused by the degree of glycosylation of human IL-3. It furthermore shows the differing binding capabilities of several anti-hIL-3 antibodies depending on the glycosylation status of the hIL-3 (1 µg IL-3 blotted per lane; Antibodies applied at 1 µg/ml; HEK: IL-3 expressed in HEK cells (Biomol); Insect: IL-3 expressed in insect cells (Biolegend); *E. coli*: IL-3 expressed in *E. coli* (Peprotech))

DESCRIPTION OF THE PRESENT INVENTION

In the prior art, the efficacy of potential IL-3 specific antibodies was tested on leukemia cell lines or TF1 cells.

TF1 is a model human erythroblast cell line, which has been established by T. Kitamura in 1987 from bone marrow of a 35 year old male Japanese suffering from severe pancytopenia. Growth of TF1 cells is completely dependent on the presence of IL-3 or GM-CSF. Thus, a test based on the cell proliferation of TF1 cells can be used to determine blocking of the IL-3 activity which in turn leads to a decrease or even a complete inhibition of the growth of TF1 cells.

For using an antibody in the treatment of humans, the capability of blocking IL-3 activity should also be assayed in a model which is not as remote from the in vivo context, as is the TF1 cell line model. Therefore, the inventors tested IL-3 antibodies of the present invention with primary human cells obtained from a patient to be treated with the IL-3 antibodies or from healthy subjects as controls. Primary cells and use of IL-3 produced by primary human cells are superior to a cell line model.

However, it was found that IL-3 antibodies, that efficiently blocked the TF1 cell line growth, did not necessarily have the same effect on the growth of primary human cells obtained from a patient to be treated with IL-3 antibodies. An example of an antibody, which shows efficient blocking capability in the TF1 cell line model, but no longer in the assay using primary human blood cells, is an antibody produced by the hybridoma cell line DSM ACC 3163, which is herein referred to as "clone 11". The inventors found that results obtained with an in vitro model using the TF1 cell line, cannot be used to predict correctly if a potential IL-3 antibody is effective for treatment of an IL-3 related disease or malfunction in a patient and the inventors found the reason for this. On the other hand, it was found that IL-3 antibodies, which did not very efficiently block the TF1 cell line growth, could be used to efficiently block the growth of primary human cells. In other words, the results obtained with TF1 cell lines only are not reliable and can yield "false positive" as well as "false negative" results, i.e. can indicate activity for antibodies that are inactive in primary human cells or inactivity or low activity for antibodies that are active in primary human cells. One example for this scenario is an antibody produced by the hybridoma cell line DSM ACC3164, which is herein also referred to as "clone 13". Due to its behavior in the cell line model, clone 13 was thought to not be an efficient therapeutic antibody. The inventors, however, found that this antibody has a surprisingly high potential when used in primary human blood cells. Thus, testing antibodies in cells of TF1 cell line not necessarily provides reliable results for the intended use in patients.

The inventors now found the reason for the unpredictability of the behavior of IL-3 antibodies. It was first assumed by the inventors that this could be due to the concentration of IL-3 necessary to observe any IL-3 induced effect. With TF1 cells half-maximal stimulation of cell growth can be seen with about 1 ng/ml IL-3. In contrast, half-maximal upregulation of CD203c basophils can already be observed at about 0.01 ng/ml IL-3. Another explanation was that TF1 cells express an N-terminal truncated splice variant of the IL-3 receptor alpha chain (J Biol Chem. 2009; 284:5763-73). Expression of this splice variant may be less pronounced on primary human cells.

The inventors, however, then found another reason for the difficulties with prediction of hIL-3 blocking activity in vivo. Surprisingly, they found that the glycosylation and the degree of glycosylation of IL-3 determines whether an antibody binds to IL-3, and, that antibodies that bind to glycosylated hIL-3, can block IL-3 activity.

The glycosylation status is depending on the type of cell producing the human IL-3. If IL-3 is produced recombinantly by E. coli cells, the resulting human IL-3 will not be glycosylated. The molecular weight of non-glycosylated human IL-3 is about 15 kD. If IL-3 is produced by insect cells, the resulting human IL-3 will be weakly glycosylated. The molecular weight of this weakly glycosylated IL-3 is from about 15 to about 20 kD, with a maximum at about 18 kD. If IL-3 is produced by human cells, such as HEK cells, the resulting human IL-3 will be more strongly glycosylated. The molecular weight of glycosylated human IL-3 produced by HEK cells is from about 17 to about 40 kD, with a maximum at about 25 to 35 kD. Therefore, a glycosylated human IL-3 suitable in the present invention can be defined as glycosylated human IL-3 having a molecular weight of at least 17 kD, preferably at least 20 kD or more.

A "glycosylated human IL-3" suitable in the present invention can also be defined as a glycosylated human IL-3, wherein the glycosylation is, with reference to structure, type, and/or length of the glycosyl chain, very similar to the structure, type, and/or length of the glycosyl chain in hIL-3 produced by HEK cells or primary human cells. A glycosyl chain is deemed to be "very similar" if the length and/or structure of the glycosyl chain is at least 80%, 90%, 95%, or 100% of the length/structure in glycosylated hIL-3 produced by HEK cells or primary human cells. The human cell can be a human cell line, or a primary human cell. A "strongly glycosylated" human IL-3 can be defined as "glycosylated human IL-3 with a molecular weight of from at least 20 kD to about 40 kD" (see also FIG. 52).

Antibodies described to be blocking (e.g. clone 11, R&D clone 4806, R&D clone 4815, Novus clone MM0402-10B35) bind and block non-glycosylated IL-3 very well. They also bind weakly glycosylated IL-3 (expressed in insect cells) very well, however, they do not block this type of IL-3. If glycosylation of IL-3 is more pronounced (e.g. expression in HEK cells) these antibody neither bind nor block IL-3. Thus, antibodies having the desired activity can be identified by using glycosylated hIL-3 for testing of inhibitory properties, or in other words, an antibody that binds to glycosylated hIL-3 very well and blocks IL-3 activity in vitro will also have inhibitory properties for hIL-3 when used in vivo. hIL-3 produced by transfected human cells or, even better, IL-3 produced by primary activated human T cells can be used in these tests. Moreover, it might be efficient to use glycosylated hIL-3 as antigen for producing antibodies specific for glycosylated hIL-3 and for screening of monoclonal antibodies produced by hybridomas.

An anti-hIL-3 antibody according to the present invention refers to an antibody that has an inhibitory effect on hIL-3 when administered to a patient, i.e. is blocking glycosylated IL-3 in vivo. The term "anti-hIL-3 antibody" when used in the context of the present invention is used for an antibody specific for the glycosylated form of hIL-3, in particular for hIL-3 with the glycosylation form as found in the human body. Furthermore the term "antibody" is meant to encompass all immunologically effective units or elements such as whole antibodies, fragments, variants, constructs, or conjugates of antibodies, or recombinant antibodies comprising at least one CDR of an active antibody as defined above.

The terms "human IL-3" or "hIL-3", respectively, refer to hIL-3 in a form as naturally occurring, i.e. human IL-3 in glycosylated form, produced in a primary human cell or recombinantly produced IL-3 having the sequence of human IL-3 in glycosylated form, such hIL-3 expressed by human cells, or a fragment thereof having the same binding properties. The terms IL-3 and hIL-3 are used interchangeably with regard to the function. Whenever the term hIL-3 is used, it refers to human or human derived IL-3.

When the term "hIL-3 blocking activity in vivo" is used in the context of the present invention it refers to the activity of an anti-hIL-3 antibody of the present invention that is able to block the binding between hIL-3 and the antibody not only in cells of a cell line but also in vivo.

The present invention provides an efficient way for identifying antibodies that can be used in treatment of an IL-3 related disease or malfunction in a patient, namely the use of hIL-3 in a glycosylated form, in particular glycosylated as in a primary human cell, for testing hIL-3 antibodies. Moreover, to generate specific anti-hIL-3 antibodies, in a preferred embodiment hIL-3 in glycosylated form is used as antigen. Surprisingly, using hIL-3 in glycosylated form is superior to non-glycosylated recombinantly expressed IL-3 and will be more indicative of the results that will be obtained in in vivo context during treatment of a patient with the hIL-3 antibodies. Surprisingly, antibodies binding to hIL-3 in a glycosylated form, that is similar to the human IL-3, are superior to those binding to weakly glycosylated hIL-3, such as obtained in insect cells. In addition, in assays with human blood the antibodies of the present invention give strong hIL-3 signals already at concentration of 0.1 ng/ml hIL-3, while assays with TF-1 cells are typically performed with IL-3 concentrations of 2.5-5 ng/ml. The assays with human blood allow to directly detect bioactivity of hIL-3 present in the supernatant of activated human PBMC.

Antibodies of the present invention can be produced with methods known in the art and outlined in detail below. Thus, mammals like mice can be immunized with an antigen, which is IL-3 or a fragment thereof comprising at least the epitope as described below. In one embodiment glycosylated hIL-3 is used for immunisation. Hybridomas can be created with a method based on the well-known Köhler-Milstein method and are then screened for their binding to IL-3. IL-3 binding clones can then be tested by their binding to glycosylated hIL-3. Phage display methods can also be used to select antibodies for further testing and it is preferred to use glycosylated hIL-3 for panning.

It is critical for the present invention to carry out functional tests for selecting anti-hIL-3 antibodies for diagnostic and therapy only with hIL-3 in glycosylated form, such as hIL-3 as expressed by primary human T cells or by transfected human cells. Functional tests in this regard refer in particular to tests for binding to hIL-3, or for properties of the tested antibody in blocking, inhibiting, interfering binding of an antibody to hIL-3. hIL-3 or a derivative thereof can be used as long as it has the same binding properties as native i.e. glycosylated hIL-3 in vivo. Most preferred is the use of hIL-3 obtained from primary human cells, such as activated T-cells. Recombinant hIL-3 can also be used as long as it is glycosylated as defined herein. Examples are hIL-3 obtained from primary human cells or expressed in HEK cells. hIL-3 in non-glycosylated form as obtained for example from *E. coli* and weakly glycosylated hIL-3 from insect cells is not useful, as it is not or not as suitable for any functional screening or selection of IL-3 binding antibodies.

The primary cells used to determine the efficiency of the hIL-3 antibodies of the present invention are primary human blood cells as known to the skilled person, and are preferably obtained from a patient suffering from rheumatoid arthritis (RA). The primary human blood cells can also be obtained from a healthy subject, and can be used as a control. For testing a blood sample can be treated with heparin, citrate, or EDTA as anti-coagulant as is known in the art. Preferably, EDTA is added to the blood sample as anti-coagulant. This kind of blood sample is also referred to as "EDTA blood".

Primary human blood cells contain basophil granulocytes, also termed "basophils", which can be detected with known methods, such as flow cytometry using labelled antibodies, such as combinations of fluorescently labelled antibodies directed against basophil expressed cell markers, such as CD11b, CD123, CCR3, and CD203c. Capability to block hIL-3 activity can for example be tested by assaying hIL-3 induced upregulation of CD203c in basophil granulocytes (Hauswirth A W et al., *Int J Immunopathol Pharmacol.* 2007; 20:267-278). IL-3 also induces upregulation of CD11b and downregulation of CD131 in basophils. Furthermore, hIL-3 induces upregulation of HLA-DR and down-modulation of CD131 in plasmocytoid dendritic cells (pDC), which are also comprised in a blood sample comprising primary human blood cells. pDCs can be detected as is known in the art, such as by flow cytometry using combinations of fluorescently labelled antibodies directed against dendritic cell expressed cell markers, such as HLA-DR, CD123, and CD4. In addition, IL-3 induced downregulation of CD131 can be quantified on CD14+CD16+ monocytes, CD14++ monocytes, and eosinophils. Therefore, the capability of anti-hIL-3 antibodies to efficiently block hIL-3 activity can be assayed by known tests, such as by quantifying the upregulation of CD11b and CD203c in basophils, or of HLA-DR in pDCs, or the downregulation of CD131 in various cell types including basophils, pDC, monocytes or eosinophils. Basophils are the preferred cell type to quantify the bioactivity of IL-3 in a human sample, because basophils strongly react to IL-3 and show little reactivity to closely related cytokines such as IL-5 and GM-CSF.

It has been found that to preserve the primary nature of the human blood cells, and therefore their suitability as an in vivo model, no steps leading to isolation or purification of subfractions of the primary human blood cells obtained should be done. For example, it has been surprisingly shown that a basophil cell population obtained by an isolation and purification step (e. g. Ficoll preparation, or cell sorting) yielding the basophil granulocytes does not respond very well to IL-3. Consequently, high concentrations of IL-3 are necessary to be able to observe any IL-3 induced effect. Therefore isolated and purified populations comprising subfractions of the primary human blood cells such as the basophils, are not very suitable to investigate neutralizing properties of IL-3 antibodies.

Thus, a crucial step in identifying useful hIL-3 antibodies and in developing new anti-hIL-3 antibodies in a specific and efficacious way has been identified. To obtain a specific antibody in an efficient way it is important to provide for the correct antigen for screening, while developing the antibody, for example a monoclonal antibody using the hybridoma cell technique. Based on the prior art knowledge glycosylation was deemed not to affect bioactivity of hIL-3 to a major degree and that all monoclonal antibodies characterized for inhibitory activity against IL-3 recognize IL-3 largely independent of its glycosylation. Thus, it appeared very unlikely that glycosylation would affect the ability of monoclonal antibodies to block hIL-3 bioactivity.

Surprisingly however, it was found by the inventors that for preparing a specific and efficient antibody it is crucial to test an antibody for the binding using hIL-3 in its glycosylated state as antigen to produce an hIL-3 specific antibody, such as a monoclonal anti-IL-3 antibody.

It could be shown that the ability of anti-hIL-3 antibodies to block hIL-3 bioactivity in humans is dependent on the glycosylation of hIL-3, i.e. an anti-hIL-3 antibody having strong affinity to non-glycosylated hIL-3 not necessarily shows blocking activity against glycosylated hIL-3. However, in vivo hIL-3 is present in glycosylated form, therefore any antibody foreseen to be used in vivo or for therapy, respectively, has to be tested for its binding properties against glycosylated hIL-3. Using this specific screening results in antibodies that have a very low $IC_{50}$ and, thus, are very valuable for therapy.

The corresponding data showing this effect are outlined in detail in the examples. Different forms of IL-3 were tested for their bioactivity. Three types of recombinant human IL-3 were compared: E. coli expressed non-glycosylated IL-3 (about 15 Kilodalton (kD)), insect cell expressed glycosylated IL-3 (about 15-20 kD) and HEK cell expressed glycosylated IL-3 (about 17-40 kD).

It was found that all versions of IL-3 have a very similar bioactivity in assays with primary human basophils or TF-1 cells. E. coli expressed non-glycosylated IL-3 is very efficiently blocked by the IL-3 antibodies Clone 11 and R&D Systems mab 203 (Clone 4806), while the glycosylated insect cell or HEK cell expressed IL-3 is only blocked to a very minor degree. In contrast, the antibodies produced by hybridoma cell clone 13 and clone P8C11C8-6 block the bioactivity of both glycosylated and non-glycosylated IL-3. The ability of the antibodies to block IL-3 was similar in an assay with TF-1 tumor cells and primary human basophils.

Human IL-3, recombinantly expressed in insect cells or HEK cells, may have a different type of glycosylation than hIL-3 expressed by primary human cells. To analyze the effect of the antibodies on hIL-3 expressed by primary human cells, human PBMC were activated from RA-patients for 3 days with anti-CD3 antibodies and the concentration of IL-3 in the cell culture supernatant was measured. The supernatant of PBMC producing very low, medium and high levels of IL-3 were tested in a very sensitive bioassay for IL-3 activity using human primary basophils. The supernatant was preincubated with various IL-3 antibodies. The results show that Clone 13 and P8C11C8-6 block the bioactivity of primary human IL-3, while Clone 11 and R&D 203 were almost ineffective (see Example 9).

The present invention, thus, provides an efficient method for development of blocking antibodies against human IL-3 and especially for analysis of inhibitory activity of the antibodies, glycosylated hIL-3 (e.g. from insect cells) or hIL-3 expressed by human cells is used. E. coli derived IL-3, as used frequently in the prior art to characterize the inhibitory activity of monoclonal antibodies against IL-3, can be misleading and is not suited to produce antibodies as specific and affine as the antibodies of the present invention.

Further tests were carried out by the inventors as described in detail in the examples and the results show the favorable properties of the antibodies of the present invention. The ability of various combinations of IL-3 antibodies to recognize glycosylated and non-glycosylated hIL-3 was measured in sandwich ELISAs (see Example 10). Various combinations of the antibodies clone 11, clone 13 and P8C11C8-6 were tested. While all combinations detected E. coli-derived non-glycosylated hIL-3 and insect cell derived glycosylated hIL-3, only the combination of clone 13 and P8C11C8-6 also detected HEK cell-derived hIL-3 with a comparable efficacy. HEK cell derived hIL-3 is more heavily glycosylated than insect cell derived hIL-3. Any combination containing clone 11 in the sandwich ELISA yielded only very low signals with HEK cell derived hIL-3.

Furthermore, antibodies were analyzed for their selectivity and accuracy in detecting IL-3 expressed by primary anti-CD3 activated human PBMC (see above). In these experiments the concentration of IL-3 by ELISA and in a functional bioassay with human basophils was measured, using insect cell derived and HEK cell-derived hIL-3 as standard. The IL-3 concentration in the supernatant of activated human PBMC measured by sandwich ELISA with antibodies P8C11C8-6+Clone13-HRP correlated very well with the IL-3 concentration measured by the bioactivity assays. The sandwich ELISA with antibodies Clone13+Clone11-HRP resulted in about 4 fold lower IL-3 concentration in the supernatant of activated human PBMC. It was also shown that the commercially available antibodies R&D clone 4806, R&D clone 4815 and Novus clone MM0402-10B35 were not able to detect HEK cell-derived hIL-3, and, thus are not useful for diagnostic methods and are not suitable for therapy. This further shows the superiority of the antibodies of the present invention and the importance of the glycosylation status of the hIL-3 peptide to be detected or inhibited.

The hIL-3 antibodies of the present invention are specific and efficacious in vivo and can be used in an in vivo context. The antibodies of the present invention also show surprisingly low levels of cross-reactivity with IL-3 molecules of other mammalian origin. Moreover, a method is provided to develop and use antibodies in a more efficient way. Apart from a very high specificity for only IL-3 but not for other cytokines, Antibodies of the present invention show surprisingly little cross-reactivity with mammalian IL-3 although amino acid identities of human protein and mammalian protein can be up to 99%, for example for marmoset, rhesus or chimpanzee proteins amino acid identities can be in the range between 72 and 99% (see FIG. 1).

Among further cytokines, which may also be present at an elevated level in autoimmune diseases, IL-5 and GM-CSF are particularly important. A high cross-reactivity of an anti-IL-3 antibody with such cytokines in an immunoassay can lead to incorrect results regarding the fact that an IL-3 overexpression has an important influence in the manifestation and progression of the autoimmune disease. Such results, however, have an important impact on the decision whether the application of an anti-IL-3 antibody can be considered a promising therapeutic approach.

It is thus preferred for inventive antibodies to show the lowest possible cross-reactivity with human IL-5 and GM-CSF. Particularly preferred, it is a characterizing feature of an inventive antibody that it binds to IL-5 or GM-CSF to an extent of below 5%, more preferred below 2% and particularly preferred below 1% as compared to the amount of hIL-3 bound by the antibody. Such antibodies are provided by the present invention and, moreover, methods are provided to develop antibodies having such low cross-reactivity, in particular by using hIL-3 in a glycosylated form for preparation and detection.

The present invention provides anti-hIL-3 antibodies with properties as detailed above that are suitable for therapeutic use as they efficiently block hIL-3 activity in vivo. Thus, in one aspect the invention provides anti-hIL-3 antibodies obtainable by immunization with hIL-3 in glycosylated form and/or by screening with hIL-3 in glycosylated form having an $10_{50}$ value of 100 ng/ml or less and having a cross-reactivity with other cytokines and non-human IL-3 of below 5%, for use in treating IL-3 dependent diseases and conditions.

The capability of the antibodies to efficiently block hIL-3 activity on primary human blood cells and to inhibit bioactivity of glycosylated hIL-3, preferably expressed in human cells can be determined as described below.

To analyze if an IL-3 specific antibody is capable of efficiently blocking hIL-3 activity in primary human cells, methods known in the art can be applied. In the following a method is described that is useful for analysis of this property.

In a first step of a method of determining efficiency of blocking hIL-3 activity of hIL-3 in primary human blood cells, the IL-3 antibody to be tested is preincubated with IL-3.

The test should be carried out with at least one concentration, preferably at least two or various concentrations of the antibody, with a constant concentration of glycosylated hIL-3 for determining an $IC_{50}$ value. For example, a constant concentration of hIL-3 can be 0.1 ng/ml. Optionally, a negative control can be included in the assay by leaving out IL-3 completely. This way it can be ascertained that IL-3 does have activity if added.

A range of concentrations of anti-hIL-3 antibody to be tested can be from about 0 to 100 µg/ml. Preferably, the range is from about 0 to 30 µg/ml. If no antibody to be tested is added, the full effect of hIL-3 induced activity can be determined.

A preincubation can be done under conditions which are well known to the skilled person. For example, the preincubation step can be carried out at room temperature for a period of about 1 to about 60 minutes, such as about 20 minutes.

A mixture comprising IL-3 and preincubated antibody to be tested is then added to a sample, such as a solution comprising primary human blood cells. The sample can be blood or a blood derivative comprising human blood cells, or a tissue. The primary human blood cells can be comprised in a blood sample obtained from a patient suffering from rheumatoid arthritis. The primary human blood cells can also be comprised in a blood sample obtained from a healthy subject to provide a control sample. The blood sample can comprise an anti-coagulant such as heparin, citrate or EDTA. Preferably, the blood sample comprises EDTA as anti-coagulant. This type of blood sample is also called "EDTA blood".

A mixture comprising hIL-3, antibody to be tested, and primary human blood cells, is then incubated under conditions which are well known to the skilled person. For example, the incubation step can be carried out at 37° C. for a period of about 10 to about 120 minutes, such as about 1 hour.

After incubation, the primary human blood cells are analyzed as is known in the art, for example by flow cytometry as is well known to the skilled person. The primary human blood cells are marked by at least one cell marker, which is labelled with a detectable unit, as is known in the art. For example a combination of fluorescently labelled cell markers for basophil and plasmacytoid dendritic cells can be used. Examples for cell markers specific for basophil granulocytes are CD11b, CD123, and CD203c. Examples for cell markers specific for plasmacytoid dendritic cells are CD123, HLA-DR, and CD4. Any combination of these and/or other known markers can be used.

The labelling step can be carried out under conditions well known to the person skilled in preparing cells for analysis by flow cytometry. For example, a staining step can be carried out at lower temperature, such as on ice, and can take about 1 to about 60 minutes, such as 20 minutes.

Labelled cells, such as basophil granulocytes and plasmacytoid dendritic cells, are then identified by flow cytometric analysis as is known to the skilled person.

For assessment upregulation and/or downregulation of the at least one cell marker is quantified. For example, the upregulation of CD203c and/or CD11b on basophils and/or the downregulation of CD131 on basophils and other cell types such as pDC, monocytes, and eosinophils, is quantified. Alternatively or cumulatively, the upregulation of HLA-DR on plasmacytoid dendritic cells can be quantified. Preferably, both the upregulation and downregulation of markers can be quantified in several different cell types. As induced by IL-3 CD203c and/or CD11b on basophils are upregulated, a decrease of these markers shows interference on IL-3/IL-3 receptor interaction by a candidate antibody. As induced by IL-3 CD131 on basophils and other cell types is downregulated, an increase of this marker shows interference on IL-3/IL-3 receptor interaction by a candidate antibody. As induced by IL-3 HLA-DR on plasmacytoid dendritic cells is upregulated, a decrease of this marker shows interference on IL-3/IL-3 receptor interaction by a candidate antibody. Thus, inhibitory activity of a candidate antibody is tested via increase or decrease of cell markers, where a decrease of a cell marker that is upregulated by hIL-3 and/or an increase of a cell marker that is downregulated by hIL-3 is an indication for inhibitory activity. The amount of inhibitory activity can be determined by determination of $IC_{50}$, i.e. half maximal inhibitory concentration necessary to inhibit the biochemical function of hIL-3.

It has been found that it is critical for an IL-3 antibody that shall block hIL-3 activity in vivo to have an inhibitory activity against glycosylated hIL-3 such that the $IC_{50}$ of the hIL-3 antibody is 100 ng/ml or less. Preferably, the $IC_{50}$ is 40 ng/ml or less, preferably 10 ng/ml or less. Methods of determining $IC_{50}$ are known to the skilled person and any method known can be used in the present test.

As antibodies of the present invention have such a low $IC_{50}$, they can be used for all purposes, in particular diagnosis and therapy, and, therefore, are very valuable.

An antibody, a fragment, or variant thereof is deemed to be "efficiently blocking", i.e. is an antibody according to the present invention, if the antibody or fragment, construct, variant or conjugate thereof exhibits an $IC_{50}$ of less than about 100 ng/ml, or less than about 40 ng/ml, or less than about 10 ng/ml for inhibiting hIL-3, which can be measured in a test for measuring blocking activity, such as a flow cytometric test of blocking induced upregulation of CD203c on basophils in the primary human blood cells, or of blocking induced upregulation of HLA-DR on plasmacytoid dendritic cells in the primary human blood cells. In other words, an antibody or a fragment, construct, variant or conjugate thereof that exhibits an $IC_{50}$ of less than about 100 ng/ml, or less than about 40 ng/ml, or less than about 10 ng/ml in a test for measuring inhibitory activity for hIL-3/IL-3 receptor interaction, and, thus, has efficient blocking activity is useful as inhibitor for hIL-3 and can be used in a composition as defined below.

One example for an antibody of the present invention is an antibody produced by hybridoma cell line DSM ACC 3281, which is herein also referred to as "P8C11C8-6". Fragments and variants of this antibody can also be used as well as recombinant antibodies comprising at least one CDR of this antibody.

P8C11C8-6 shows an $IC_{50}$ of about 10 ng/ml as determined with a method as described above.

P8C11C8-6 binds to a linear epitope in hIL-3, which is contained in a peptide having an amino acid sequence corresponding to amino acid residues 22-48 of human hIL-3 without the signal peptide (SEQ ID NO: 10): EIITHLKQP-PLPLLDFNNLNGEDQDIL (SEQ ID NO:1). Experiments suggest that the epitope recognized by P8C11C8-6 is located within amino acids 26 (H) to 36 (D) of the amino acid sequence as defined in SEQ ID NO. 10 and includes at least amino acids 27-29 (LKQ) and amino acids 31-36 might also be involved in binding.

It was found that an epitope recognized by P8C11C8-6 included aa22 (E) to aa 30 (P). Peptide IL-3-2a (SEQ ID NO:9) also gave some signal, indicating that more C-terminal amino acids (e.g. aa31-36) may be involved in binding.

A further example of an antibody of the present invention is an antibody produced by hybridoma cell line DSM ACC3164, which is herein also referred to as "clone 13". Fragments and variants of this antibody can also be used as well as recombinant antibodies comprising at least one CDR of this antibody.

Clone 13 shows an $IC_{50}$ of about 40-100 ng/ml as determined with the method described above.

Clone 13 binds to a different epitope in hIL-3, which is a conformational epitope.

It was found that clone 13 and P8C11C8-6 do not compete with each other indicating that they cover different epitopes that are involved in binding of hIL-3 to the hIL-3 receptor. Therefore, an antibody of clone 13 or P8C11C8-6 does not affect the blocking activity of the other antibody if applied in combination. Therefore, in one embodiment at least one antibody, such as one of the above mentioned antibodies, of the present invention, or a fragment, variant, construct or conjugate thereof, alone or a combination of at least two antibodies or their fragments or variants or constructs or conjugates thereof can be used for treatment and for preparing compositions comprising at least one of the antibodies or fragments of the present invention or a combination of at least two antibodies and/or their fragments and/or variants and/or constructs.

The examples enclosed with this specification show the superior characteristics with regard to specificity and lack of cross-reactivity with IL-3 of other species and with other human cytokines for antibodies according to the present invention.

The antibodies according to the present invention can be of different nature and the following more detailed illustrations of possible antibodies or antibody fragments, constructs, variants, or conjugates are only meant to be exemplary. That means that within the context of the present invention the term antibody is to be understood in its broadest sense. Any antibody, or any part derived thereof or based thereon such as a construct, fragment, variant, or conjugate, containing antibody characteristics and retaining specificity of the antibodies shown in the examples of the present invention, is considered as encompassed within the term antibody in the context of the present invention.

In principle, monoclonal antibodies as well as polyclonal antibodies can be used. Monoclonal antibodies generally have the advantage of a higher specificity as compared to polyclonal antibodies and are thus preferred in view of the present invention. In terms of the present invention, the term "antibody" shall also comprise fragments, bi-, tri- or multimeric or bi-, tri- or multifunctional antibodies having several antigen binding sites which preferably are IL-3-specific binding sites. Regarding the present invention, the term "antibody" further comprises fusion proteins containing as a part of the fusion protein an antibody or antibody fragment or complement determining region (CDRs) of an antibody of the present invention, which show a corresponding specificity and which have furthermore retained their binding ability to hIL-3.

Therefore, in one embodiment an antibody of the present invention is an anti hIL-3 antibody, fragment, variant, construct, or conjugate thereof, which comprises the complementary determining regions (CDRs) of the antibody produced by hybridoma cell line DSM ACC3281 or DSM ACC3164.

Further comprised are single chain antibodies. Moreover, the inventive antibodies can belong to any appropriate antibody class, it is however essential that their use in therapy is possible. Preferably, the anti-IL-3 antibody or the fragment thereof according to the present invention is of the class IgG, IgA, IgE, or IgM.

In the present description of antibodies according to the invention, the term "antibody" is meant to encompass all immunologically effective units or elements such as whole antibodies, fragments, variants, constructs, or conjugates of antibodies, or recombinant antibodies comprising at least one CDR of an antibody as defined above and in the claims. "Immunologically effective" in this regard refers to units or elements that inhibit, decrease, hinder or in any other way influence the interaction between hIL-3 and its receptor and thereby decrease, block, or hinder activity of hIL-3. As far as fragments of the inventive antibody are concerned, it is preferred that the fragments retain an antigen-binding domain and an Fc-domain. As an alternative, Fab or $F(ab)_2$ fragments can be used as long as they intervene with the binding of hIL-3 to its receptor on the cell surface or with the ability of hIL-3 to activate its receptor. A conjugate of the present invention is a unit, wherein an anti-hIL-3 antibody or an active part thereof is linked to a functional molecule, wherein the functional molecule can provide for a desired function like immobilization, labelling, etc.

The term "at least one antibody" when used in this specification means that at least one antibody or at least one antibody fragment or at least one antibody construct or at least one antibody variant or at least one antibody conjugate etc., wherein the fragment, construct, variant or conjugate etc. has the desired activity, is present. A combination of the antibodies of the present invention can be a combination of the two above mentioned antibodies or variants thereof such as humanized forms of these antibodies, or a combination of an antibody and/or a fragment and/or a construct and/or a variant and/or a conjugate of any of the antibodies.

In summary, for the purpose of the present invention, the actual form of a molecule considered to be encompassed by the term "antibody" is irrelevant as long as it specifically binds to hIL-3 in a manner sufficient to inhibit the interaction of hIL-3 with its natural receptor and thus to prevent the cellular reaction triggered thereby.

Antibodies according to the present invention can be produced by any method known to the skilled person. For example, antibodies can be generated using the complete hIL-3 protein as an immunogen and later on selecting for antibodies and antibody clones which are specific for the mentioned sequences. As an alternative, a peptide containing within its sequence the desired parts or epitopes of hIL-3 can be used for immunization. A further possibility is the use of artificial epitopes which contain only the very epitope (conformationally discriminating epitope, CDE) integrated into an environment which allows for the generation of antibodies. Such methods are known to the skilled person and described e.g. in WO2005/051999. In summary, any method for producing antibodies is useful within the context of the present invention as long as it produced antibodies with the required specificity and if necessary allows for the selection of the inventive antibodies from a plurality of antibodies which are produced upon immunization with IL-3 or parts thereof.

The antibody of the invention can be of any origin, e.g. human, mouse, goat, rabbit. Human or humanized antibodies are particularly preferred. As a commonly used method, the production of antibodies is carried out by immunizing appropriate mammals, e.g., mice, rat, hamster or rabbits. As mentioned above, antibodies of the present invention can also be produced recombinantly as long as they have the above defined properties.

For therapeutic use, however, it is less desirable to use non-human proteins since they can cause quite severe adverse reactions of the immune system. This is for example one cause of severe side effects of the presently used mouse antibody infliximab mentioned above.

It is thus particularly preferred for the antibodies to be human antibodies or that a humanization of antibodies produced in other species is performed. Methods for the humanization of antibodies are known to a person skilled in the art and are described in, e.g., Jones P. T. et al., *Nature* 1986; 321:522-525, Santos A. D. and Padlan E. A., Proq *Nucleic Acid Res Mol Biol.* 1998; 60:169-94, Presta L. G., *Curr Opin Immunol.* 2008 August; 20(4):460-70, Almagro J. C. and Fransson J., *Front Biosci.* 2008 Jan. 1; 13:1619-33.

The term humanized antibody is generally used for antibodies with more than 95% of human origin. Antibodies with less human character, e.g., with 70% human antibody parts, are often designated as chimeric antibodies. Humanized or chimeric antibodies are produced by means of biotechnological methods using recombinant DNA-technology, whereby a part of the animal/mammalian protein, which contains at least the antigen-binding parts, is combined with further parts of a human antibody such that a functional antibody or fragment, construct, variant, or conjugate thereof is produced.

A possibility to produce a humanized antibody is, for instance, to replace at least one of the CDRs of a receptor antibody, which is a human antibody, by the ones of an hIL-3 specific antibody which was produced in a non-human mammal. Furthermore, it is possible to use further parts than the at least one CDR of the mammalian antibodies such that the entire CDR-region, the entire variable region or Fab- or Fab'-parts are combined with corresponding further parts of the human antibody.

In addition to humanized and chimeric antibodies, also human antibodies can be used within the context of the present invention. Human antibodies can be prepared using techniques for human monoclonal antibody production as described in the art. One commonly used method is the so-called phage display technique where human antibodies are produced using phage displayed libraries. In this technique, DNA sequences coding for human antibodies are inserted into phage DNA to provide a phage DNA library. Each phage in the library carries a different antibody on its surface. Such libraries can be screened for antibodies that bind the desired antigen. According to the present invention, screening can be performed with regard to the epitope contained within the amino acid residues 22-48 of hIL-3. Upon mixing of such a library with the antigen/epitope-carrying protein or peptide, only phages with antigen-specific antibodies are selected. Such phages carrying specific antibodies can be propagated and the antibody obtained therefrom in high amounts. Similar to hybridoma cells, also mammalian cells which are transformed with genetic information from such phages can produce antibodies consecutively (see, e.g., Beerli et al., *PNAS* Sep. 23, 2008 vol. 105 no. 38 14336-14341).

As a further possibility, human antibodies can also be obtained from transgenic animals. Also by this method, complete human antibodies can be obtained. For this technique, genetically engineered transgenic mice are prepared to carry the human antibody genes. While the expression of mouse-specific antibody genes is suppressed, the expression of human antibody genes is promoted in such mice. Technologies using transgenic mutant mice that are capable of producing human antibodies in response to immunization have been described in the art and are available to the skilled person, e.g. XENOMOUSE® technology (see, e.g., Jakobovits A., *Nature Biotechnology* 25, 1134 1143 (2007)), or ULTIMAB® mouse technology from Medarex.

The hIL-3 specificity and cross-reactivity of the antibodies according to the invention can be easily determined by methods known in the art, such as enzyme-linked immunosorbent assay (ELISA). In one known method for determining specificity and cross-reactivity, recombinantly produced cytokines (e.g. hIL-3, IL-5 and GM-CSF, or IL-3 from other species, respectively) are immobilized, such as coated onto a suitable surface in the test arrangement, the produced anti-human-IL-3-antibodies are added and their binding is detected on the coated surface by means of a detection reagent, such as a labelled anti-IgG-antibody. In such a test regimen, antibodies according to the present invention bind nearly exclusively to IL-3 while binding to IL-5 and GM-CSF occurs only to a very minor extent, if at all. The same is true for antibodies according to the invention as far as IL-3 from other species is concerned (see Example 4).

To identify new antibodies that bind to primary human IL-3 (glycosylated IL-3 produced by primary human cells) and that are useful for detection of primary human IL-3 the antibodies Clone 13 or P8C11 can be used. It has been shown that Clone 13 or P8C11 bind fully glycosylated primary human IL-3, as the concentration of primary human IL-3 measured with both antibodies in a sandwich ELISA using IL-3 recombinantly expressed in *E. coli*, insect cells or human cells as standard correlates very well with the bioactivity of primary human IL-3 and recombinantly expressed IL-3 in functional assays with primary human cells (as described above). To determine whether a new anti-IL-3 antibody (clone X) could be used for detection of primary human IL-3, clone X could be used for coating of ELISA plates. Then primary human IL-3 and recombinantly expressed IL-3 (as standard) is added in various dilutions. Bound IL-3 is then detected in one assay with HRP-labelled clone 13 in a second assay with HRP-labelled P8C11. Clone 13 and P8C11 recognize non-overlapping epitopes of IL-3. If the sandwich ELISA with clone x+clone13-HRP or with clone x+P8C11-HRP gives correct concentrations for primary human IL-3 compared to the standard and the known concentration of primary human IL-3 (e.g. determined by sandwich ELISA with P8C11 and clone 13) then, this new antibody clone x would be suitable for detection of primary human IL-3. Alternatively the new clone X could be used for detection (e.g. HRP-labelled clone X) in combination with clone 13 or P8C11 for coating.

The present invention provides antibodies that are superior to known antibodies in many regards and a method for obtaining them. In many experiments and also in the examples enclosed to the present specification, antibodies of the present invention, such as clone 13 and P8C11C8-6 have proven very superior characteristics with regard to specificity, in vivo blocking capability of hIL-3 induced activity, lack of cross-reactivity but also with regard to affinity and avidity. These preferred antibodies therefore are considered to be especially suitable for use in therapeutic treatment. Therefore, one aspect of the present invention refers to these antibodies including their fragments, variants, constructs and conjugates for use in therapy.

When used in therapy, it is preferred to use an inventive anti-IL-3 antibody, such as clone 13 or of P8C11C8-6, in a humanized version. For this purpose, clone 13 or P8C11C8-6 is humanized in any manner known in the art. In this context, at least one of the CDRs of clone 13 or of P8C11C8-6 is identically maintained/preserved, other parts of the mouse-antibody clone 13 or P8C11C8-6 can entirely or partially be replaced by sequences of human antibody origin. In this context, it is essential that the obtained humanized antibody still shows the same specificity which can easily be determined using known methods. Preferably, such a humanized antibody clone 13 or P8C11C8-6 also shows just as little cross-reactivity with IL-3 of species other than the human and with other human cytokines as the deposited mouse clone 13 or P8C11C8-6.

A further subject-matter of the present invention is a nucleic acid which encodes an antibody, an antibody fragment, an antibody variant an antibody construct, an antibody conjugate, or sequences for CDRs conveying specificity of antibodies according to the present invention. Besides the production of antibodies via the immunization of animals/mammals route and/or via the hybridoma technique for the production of monoclonal antibodies, it has for some time now also been established to produce antibodies by means of recombinant methods.

Hence, it is also a possible and preferred method to use respective nucleic acids to produce e.g. antibody fragments in bacteria or eukaryotic cells. Corresponding methods for producing recombinant antibodies or antibody fragments are known to a person skilled in the art (see e.g., Jeong K J, Jang S H, Velmurugan *N, Biotechnol* J. 2011 January; 6(1):16-27; Li J et al., *J Immunol Methods*. 2007 Jan. 10; 318(1-2):113-24).

The advantages of recombinantly obtained antibodies are that they can be produced entirely outside the animal/mammal organism. In this respect, it is also possible to obtain antibodies which could not be produced in animals/mammals, for instance, because the antigens are substances which are harmful to the organism or because certain biochemical conditions are relevant for the desired antibodies which can only be controlled in an exact manner in an in-vitro system.

Especially for the production of human or humanized antibodies, in particular for therapy, the use of the recombinant antibody technology can be advantageous, since, as already mentioned above, an immune response of the patient against antibodies produced in other organisms can be prevented. Such an immune response to the non-human part of an antibody could neutralize the therapeutic agent or can even jeopardize any positive effect to the patient by entailing severe side effects.

By means of recombinant methods, antibodies and/or their fragments can also readily be coupled with other proteins and, thus, multifunctional constructs, multispecific or bi- or polyfunctional conjugates, multi-functional and multispecific antibodies etc. can be produced (Dübel and Kontermann 2001, Recombinant Antibodies. In: R. Kontermann and S. Dübel (EDS), Antibody Engineering, Springer Verlag, Heidelberg/New York, pages 3-16.) According to the present invention, a nucleic acid sequence which codes for an inventive antibody comprises nucleotides which encode at least those parts of the antibody which confer the specific binding properties of the antibody to the specific epitope within the amino acid residues 22-48 of hIL-3.

In a preferred embodiment, the nucleic acid codes for the antibody produced by hybridoma cell line DSM ACC3164 ("clone 13") or DSM ACC3281 ("P8C11C8-6") or fragments, variants, constructs, or conjugates thereof. Hybridoma cell line DSM ACC3164 was deposited with the Deutsche Sammlung von Mikroorganismen und Zellkulturen (DSMZ) (Inhoffenstraße 7B, 38124 Braunschweig, Germany), on Mar. 14, 2012. Hybridoma cell line DSM ACC3281 was deposited with the Deutsche Sammlung von Mikroorganismen und Zellkulturen (DSMZ) (Inhoffenstraße 7B, 38124 Braunschweig, Germany), on Oct. 7, 2015. A further, especially preferred nucleic acid codes for a humanized clone 13 or P8C11 C8-6, whereby it comprises at least those nucleotides coding for the regions in antibody clone 13 or P8C11 C8-6, which entail the binding to the specific hIL-3-epitope according to the present invention.

A further subject-matter of the present invention is a hybridoma cell line which produces a monoclonal anti-IL-3 antibody according to the present invention. Production of hybridoma cell lines and obtaining monoclonal antibodies therefrom is well known in the art. Starting from and based on the first publications of the method by Köhler and Milstein, this method has been widely used and further improved. Generally, for the production of monoclonal antibodies, Balb/c mice are immunized with an antigen, in the present case hIL-3, for example glycosylated hIL-3, and preferably those parts of hIL-3 which contain amino acids 22-48 of hIL-3. Methods for the generation of a specific antibody against a desired epitope are well-known in the art. Splenocytes of the immunized mice are fused with myeloma cells and the obtained hybridomas tested for the production of antibodies using, e.g., an ELISA assay. Clones which have been tested positive for the production of specific antibodies are further propagated to form a stable hybridoma cell line that can be maintained and used for the consecutive production of the desired antibody.

An especially preferred hybridoma cell line according to the present invention is cell line DSM ACC 3164 producing antibody clone 13 or cell line DSM ACC 3281 producing antibody clone P8C11C8-6.

It is vital that antibodies used in therapy do not entail drawbacks brought on e.g. by cross-reactivity with other unrelated cytokines or severe immunological responses experienced with known antibodies.

The antibodies of the present invention are valuable for therapeutic use. Therefore, further subject and embodiment of the present invention is an antibody as defined above for therapeutic use, and a composition comprising at least one antibody as defined above and optionally a pharmaceutically acceptable excipient or carrier for therapeutic use. Such pharmaceutical compositions according to the invention are characterized by the presence of a pharmaceutically effective amount of at least one antibody or an active part thereof, such as an antibody fragment, antibody construct, antibody variant, or antibody conjugate, as described herein as an active ingredient. Usual excipients and/or carrier substances for pharmaceutical preparations can be included as desired and deemed appropriate. Such excipients and carriers are well-known in the art and the skilled person knows the optimal substances and dosages thereof.

Antibodies of the present invention and pharmaceutical compositions containing at least one antibody as defined above (including fragments, variants, constructs and conjugates thereof) can be used for the treatment or for the prevention and prophylaxis of diseases or malfunctions which are associated with elevated levels or IL-3. As discussed in the introductory part of this specification, IL-3 has a significant growth stimulating and differentiating effect on various hematopoietic precursor cells and is also a growth factor for mast cells. The signal transduction caused by IL-3 has major impact on the immune system. Any disease or medical condition in which IL-3 plays a direct or indirect role in development or progression is a candidate for the treatment by administering the antibodies according to the present invention. Preferably such disease or malfunction connected with elevated levels of IL-3 or elevated expression of IL-3 by cells capable of producing IL-3 such as basophils, eosinophils, plasmacytoid dendritic cells, monocytes, B cells, T cells, endothelial cells, and certain types of cancers/tumors, neurons, and others is related to the immune system, mostly an autoimmune disease and especially RA or acute or chronic graft-versus-host disease and multiple sclerosis.

The disease or malfunction connected with elevated levels of IL-3 or elevated expression of IL-3 by cells capable of producing IL-3 to be treated with the antibodies of the present invention can be a disease or malfunction selected from acne vulgaris, asthma, hypersensitivities, allergies; autoimmune diseases such as myocarditis, postmyocardial infarction syndrome, postpericardiotomy syndrome, subacute bacterial endocarditis, glomerulonephritis (various types), glomerulopathies (various types), interstitial cystitis, lupus nephritis, autoimmune hepatitis, primary biliary cirrhosis, primary sclerosing cholangitis, antisynthetase syndrome, alopecia areata, autoimmune angioedema, autoimmune progesterone dermatitis, autoimmune urticaria, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease, morphea, pemphigus vulgaris, *pityriasis* lichenoides et varioliformis *acuta*, Mucha-Habermann disease, psoriasis, systemic scleroderma, vitiligo, Addison's disease, autoimmune polyendocrine syndrome, autoimmune polyendocrine syndrome type 2, autoimmune polyendocrine syndrome type 3, autoimmune pancreatitis, diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, celiac disease, Crohn's disease, microscopic colitis, ulcerative colitis, antiphospholipid syndrome, aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, evans syndrome, IgG4-related systemic disease, paroxysmal nocturnal hemoglobinuria, pernicious anemia, pure red cell aplasia, thrombocytopenia, adiposis dolorosa, adult-onset Still's disease, ankylosing spondylitis, CREST syndrome, drug-induced lupus, enthesitis-related arthritis, eosinophilic fasciitis, Felty syndrome, juvenile arthritis, Lyme disease (chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, dermatomyositis, fibromyalgia, inclusion body myositis, myositis, myasthenia gravis, neuromyotonia, paraneoplastic cerebellar degeneration, polymyositis, acute disseminated encephalomyelitis, acute motor axonal neuropathy, anti-N-methyl-D-aspartate receptor encephalitis, Balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, Oshtoran syndrome, pediatric autoimmune neuropsychiatric disorder associated with *streptococcus*, progressive inflammatory neuropathy, restless leg syndrome, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease, Ménière's disease, anti-neutrophil cytoplasmic antibody-associated vasculitis, Behçet's disease, Churg-Strauss syndrome, giant cell arteritis, Henoch-Schonlein purpura, Kawasaki's disease, leukocytoclastic vasculitis, lupus vasculitis, rheumatoid vasculitis, microscopic polyangiitis, polyarteritis nodosa, polymyalgia rheumatica, urticarial vasculitis; or autoinflammatory diseases such as familial mediterranean fever; hyperimmunoglobulinemia D with recurrent fever (HIDS); TNF receptor associated periodic syndrome (TRAPS); Muckle-Wells syndrome (urticaria deafness amyloidosis); familial cold urticaria; neonatal onset multisystem inflammatory disease (NOMID); periodic fever, aphthous stomatitis, pharyngitis and adenitis (PFAPA syndrome); Blau syndrome; pyogenic sterile arthritis, pyoderma gangrenosum, acne (PAPA); deficiency of the interleukin-1-receptor antagonist (DIRA)); or transplant rejection, reperfusion injury, sepsis; or hematological malignancies such as lymphomas, leukemia, or other hematological tumors; or non-hematological malignancies.

Further circumstances which are preferably treated by administering the pharmaceutical composition according to the invention is a use in suppressing the activity of human basophils in persons suffering from an allergic reaction and for the stratification of patients having increased IL-3 levels in serum or plasma or elevated expression of IL-3 by cells capable of producing IL-3 (e.g. T cells).

To be eligible for treatment with the pharmaceutical composition of the present invention, in the respective disease or malfunction elevated levels of hIL-3 or elevated expression of hIL-3 by cells capable of producing hIL-3 (e.g. T cells) as compared to healthy persons should be present in any body fluid including synovial fluids but also blood, plasma and serum. The antibodies of the present invention which are contained in the pharmaceutical composition bind specifically to hIL-3 and thereby inhibit the activity of hIL-3.

Especially in view of RA it has been found that for a large group of patients elevated levels of hIL-3 produced by T cells are correlated with the aggravation caused in the patient and the progression of the disease. IL-3 is detected mainly in active RA, whereas patients with a non-active stage of RA usually do not show elevated expression or elevated levels of hIL-3. Thus the pharmaceutical compositions of the present invention are especially useful in treating patients with active episodes of autoimmune diseases, such as RA, and for the prophylactic treatment to avoid the occurrence of active episodes of the disease.

Since available therapies are only effective in about 50% of treated patients, providing the pharmaceutical compositions according to the invention is a major step to a new and gentle treatment of auto-immune disease in patients. Based on the lack of an overt phenotype of IL-3 deficient mice (*Nature* 1998; 392(6671):90-3) and no obvious side effects of mice treated with antibodies against IL-3 (Arthritis Rheum. 2009; 60(5):1352-61) IL-3 targeted treatment should exhibit less severe side effects than currently used pharmaceuticals, especially regarding to infection or neoplasia. In certain cases, it could be desirable to combine treatment with the antibodies and pharmaceutical compositions of the present invention with other medicines like methotrexate or leflunomide. An individualized treatment strategy according to IL-3 expression or IL-3 levels in plasma, serum or other body fluids, presents an advantage compared to available biologicals, since currently it is not possible to predict reliably, which patient will respond to a specific therapy (including biologicals). Further an individualized approach improves the safety of treatment by reducing the risk of side effects of an ineffective therapy and reduces the costs for treatment of RA.

Also the treatment with the antibodies of the present invention would preferentially be started as soon as elevated expression of hIL-3 or elevated hIL-3 levels in blood, plasma or serum are detected. Thus, early-on treatment can be applied in patients where RA activity is correlated with elevated hIL-3 levels and long term joint damage can be avoided or kept to a minimum. In addition, treatment with anti-IL-3 antibodies would preferentially be started, if patients failed to a previous treatment with DMARDs or biologicals. Further it is expected that the use of the antibodies of the invention can reduce cell infiltration of synovial tissue which can be a further negative factor in the disease pathology.

An effective dose of hIL-3 antibody contained in the pharmaceutical composition of the present invention can easily be determined by a physician as generally known in the art. An effective dose is an amount that alleviates the symptoms of the disease or prevents any further progress of the disease or deterioration of the condition of the patient. Progress of disease and condition of the patient can be monitored by determining hIL-3 expression or hIL-3 level and other markers for inflammation or autoimmunity in body fluids, preferably blood, plasma or serum, and by determining other disease scores or using known diagnostic methods. For RA, progress of the disease and the status of the patient can be determined using e.g. the DAS28 activity score. To prevent joint damage a DAS28<=2.6 should be achieved. Effectiveness of a therapy can be measured as the percentage of patients that achieve a certain (e.g. 30%, 50% or 70%) reduction in disease activity. Any decrease of hIL-3 or other markers for inflammation in body fluids is also an indication of a successful treatment. Effective doses of the pharmaceutical composition can be determined using dose-response-curves as is well-known to the skilled artisan. The amount of hIL-3 present in the body fluids of a patient as determined using the diagnostic methods according to the present invention can also be a basis for determining the effective dose of antibody in the pharmaceutical composition for each patient and the severity of the disease and malfunction.

For the pharmaceutical composition according to the invention and the amount of hIL-3 antibody contained therein, dosage further depends on the activity, avidity and the half-life of the antibody. For antibodies having a half-life of about one to two weeks, the dosage is preferably in the range of 1 to 1000 mg and more preferably 10 to 100 mg per application. The pharmaceutical composition is preferably applied once a day to once a month, again depending on the half-life of the antibody. The pharmaceutical composition of the present invention can be in any form that is useful for the intended purpose, such as solid or liquid forms. Useful are for example suspensions, solutions or emulsions. The composition can be provided for administration in any useful form, such as an injectable preparation.

Also with regard to a pharmaceutical composition and its use for the treatment of diseases which are correlated with increased hIL-3 levels in body fluids, antibody clone 13 and P8C11C8-6 are especially preferred candidates. Antibody clone 13 and P8C11C8-6 do not show detectable cross-reaction with GM-CSF and IL-5 and therefore does not influence the activity of these cytokines in the patient (see Example 4b). Further it has been shown that clone 13 and P8C11C8-6 are very effective in blocking hIL-3 activity in primary human blood cells using glycosylated hIL-3 expressed in human cell lines or primary human cells.

Clone 13 and P8C11C8-6 also show a very high affinity and avidity and already very small amounts of this antibody are sufficient for its inhibitory activity in primary human blood cells (see Example 5).

The antibodies of the present invention can also be used in a detection method, such as a sandwich ELISA, wherein hIL-3 expressed by primary human cells, such as PMBC, can be reliably and efficiently detected. In a preferred embodiment, the antibodies used in the detection method are the antibodies termed Clone 13 and P8C11C8-6.

Due to the novel identification of the glycosylation state as cause for activity, it is now possible to more efficiently screen and/or develop novel anti-hIL-3 specific antibodies. As antigen the glycosylated hIL-3 peptide is used in these instances. A "glycosylated hIL-3 peptide" is defined herein as a peptide, which comprises N-glycoslyation at either amino acid 15 or 70 of SEQ ID NO: 10, or at both amino acid 15 or 70 of SEQ ID NO:1. Such peptides can be produced by eukaryotic expression systems, such as insects cells, or human cell lines such as HEK cells, or by expression of primary human cells, such as activated PBMC.

Therefore the present invention also comprises a method of obtaining anti-hIL-3 antibodies of the present invention, wherein glycosylated hIL-3 peptide is used as antigen and as cytokine to measure binding and inhibitory activity of antibodies. In preferred embodiments of this method the glycosylated hIL-3 peptide is expressed and translated from human cells.

EXAMPLES

Preferred embodiments of the invention are outlined in the following examples which should not be interpreted as restricting the scope or spirit of the invention.

Example 1—Generation of Monoclonal Anti-IL-3 Antibodies

Anti-IL-3 antibodies were produced by immunizing Balb/c mice using at least 6 i. p. injections of human eukaryotic glycosylated IL-3 in alum at four week intervals. Two days before cell fusion, IL-3 in PBS was injected intraperitoneally. Antibody-producing splenocytes obtained from the immunized mice (HGPRT positive, able to grow on HAT medium) were fused with the myeloma cell line X63Ag8.6.5.3 in the presence of polyethylene glycol (PEG) and a selection of hybridomas performed in an HAT-selection medium. Hybridomas were cultivated in RPMI-1640 medium supplemented by 10% FCS (neat inactivated, HIA), P/S and glutamine (1:100). Obtained cells are able to grow in suspension and are split every three days in a ratio of 1:4.

For storage purposes hybridoma cells are transferred from a cell culture bottle into 50 ml or 15 ml cell culture flasks (BD FALCON™). After centrifugation at 1400 rpm for 5 minutes at room temperature, the supernatant is completely removed. Cells are resuspended in a freezing medium (90% FCS (HIA)+10% DMSO) and 1.5 ml aliquots are filled into vials. The cells are prefrozen in a freezing container in a freezer at −80° C. and after 1-2 days transferred to a liquid nitrogen storage tank.

Cloning and recloning of the obtained hybridoma cell lines are performed using limited dilution to provide long-term stable sources for monoclonal antibodies.

Obtained antibodies are shown in Table 1.

For determining the isotypes of the antibodies, ELISA assays were performed using hIL-3 coated plates to which the antibodies were added. Bound antibodies were detected using isotype specific secondary antibodies. For further analyses, only antibodies of isotype IgG were used.

TABLE 1

Overview of mAbs against human IL-3

| Original clone | First cloning | Second cloning | Isotype |
| --- | --- | --- | --- |
| Clone 2 | 2.28 | 2.28.11 | IgM, kappa |
| Clone 3 | 3.47 | 3.47.20 | IgG1, kappa |
| Clone 5 | 5.3 | 5.3.2 | IgM, kappa |
| Clone 6 | 6.38 | 6.38.14 | IgG1, kappa |
| Clone 7 | 7.42 | 7.42.45 | IgM, kappa |
| Clone 8 | 8.36 | 8.36.38 | IgG1, kappa |
| Clone 10 | 10.12 | 10.12.4 | IgG1, kappa |
| Clone 11 | 11.14 | 11.14.6 | IgG1, kappa |
| Clone 13 | 13.47 | 13.4.4 | IgG1, kappa |
| Clone 36 | 36.26 | 36.26.10 | IgG1, kappa |
| Clone 38 | 38.18 | 38.18.5 | IgG1, lambda |
| Clone 41 | 41.28 | 41.28.4 | IgG1, kappa |
| Clone 42 | 42.47 | 42.47.36 | IgG1, kappa |
| Clone 43 | 43.14 | 43.14.28 | IgG1, kappa |
| Clone 44 | 44.16 | 44.16.16 | IgG1, kappa |
| Clone 45 | 45.14 | 45.14.27 | IgG1, kappa |
| Clone 46 | 46.21 | 46.21.1 | IgG1, kappa |
| Clone 47 | 47.28 | 47.28.15 | IgG1, kappa |
| P8C11 | P8C11C8 | P8C11C8-6 | IgG1, kappa |

Example 2—Determination of the Amount of IgG1 in the Hybridoma Supernatants

Several of the obtained antibodies of the type IgG1 were isolated from hybridoma clones and their concentration determined. The determination of the concentration was performed according to following method: 96-well-plates are coated overnight at room temperature with anti-mouse IgG (1:100 in PBS) in a concentration of 100 μl/well. Blocking is performed by adding 100 μl per well of 2% BSA in PBS and incubation at room temperature for two hours. After the blocking reaction, the plates are washed twice. Two samples and blanks, respectively, of supernatants of clones 3.47.20, 6.38.14, 8.36.38, 10.12.4, 11.14.6 are incubated undiluted, as well as with dilutions of 1:3, 1:9, 1:27, 1:81, 1:243, 1:729 and 1:2187 (100 μl per well, dilution in 2% BSA in PBS) at room temperature. Mouse IgG1 in a starting concentration of 1 mg/ml is used as standard, whereas a concentration of 20 ng/ml is applied in dilutions of 1:2, 1:4, 1:8, 1:16, 1:32, 1:64 and 1:128.

The plate is washed three times and then incubated with biotinylated anti-mouse IgG1 (diluted by 1:250 in 2% BSA in PBS) for one hour at room temperature with 100 μl per well. After washing the plate a further three times, strepta-vidin-HRP (1:1000 in 2% BSA in PBS) is added for one hour at room temperature and in the dark. The concentration of the antibodies is determined after adding ABTS and incubating for further 30 minutes and measuring the signal at 405 and 490 nanometers on a spectrophotometer. Based on this determination, a desired amount of the antibodies tested is applied for the further tests.

Example 3—Detection of IL-3 by Monoclonal Antibodies in a Western-Blot Assay

For preparing the gel and performing the western-blot analysis, standard methods are used. A 12% PAA resolving gel is poured, overlayed with about 1-2 ml of water and polymerization conducted for 30 to 45 min until a recognizable "line" is formed. The water is removed, a stacking gel poured onto the resolving gel and a Teflon comb is inserted. Polymerization is performed for 30 min, then the comb is carefully removed.

Samples of IL-3 are prepared by mixing of recombinant human IL-3 1:1 with Laemmli buffer and heating the samples at 60° C. for 5 min. An amount of 1 μg per lane of IL-3 as well as a usual standard for determining molecule sizes is loaded onto the gel. The gel is then mounted in a SDS-PAGE gel electrophoresis apparatus which already contains a running buffer. The inserted gel is then cautiously overlayed with additional running buffer and electrophoresis performed at 20 to 25 mA with voltage adjusted to infinite for approximately 1.5 hours. When the run is completed, the gel is retrieved from the apparatus and the stacking gel is removed.

Six layers of Whatman paper that has been presoaked in transfer buffer, and a PVDF membrane are cut to fit the size of the gel. The transfer stack is adjusted in the usual way and transfer effected by semi-dry blotting for 40 min at 20-25 mA and voltage adjusted to infinite. The membrane is then incubated overnight at 4° C. on a shaking apparatus with a blocking solution (5% powdered skim milk in PBS) and the membrane washed three times for 5 min each with PBS at room temperature.

Antibody clones are incubated at a concentration of 5 μg/ml in blocking solution for 2 hours at room temperature under agitation on the shaking apparatus. After three washing steps, HRP labelled anti-mouse immunoglobulin (1:1000 in blocking solution) is added and incubation is conducted for 1 hour at room temperature while shaking. After three further washing steps, a detection solution (1:1 mixture of solutions A and B of the Western blotting Luminal Reagent obtained from NALGENE) is added and incubated for 1 min at room temperature. Films are then adjusted on the membranes with different times of expositions and developed in the dark room.

Figure 2:
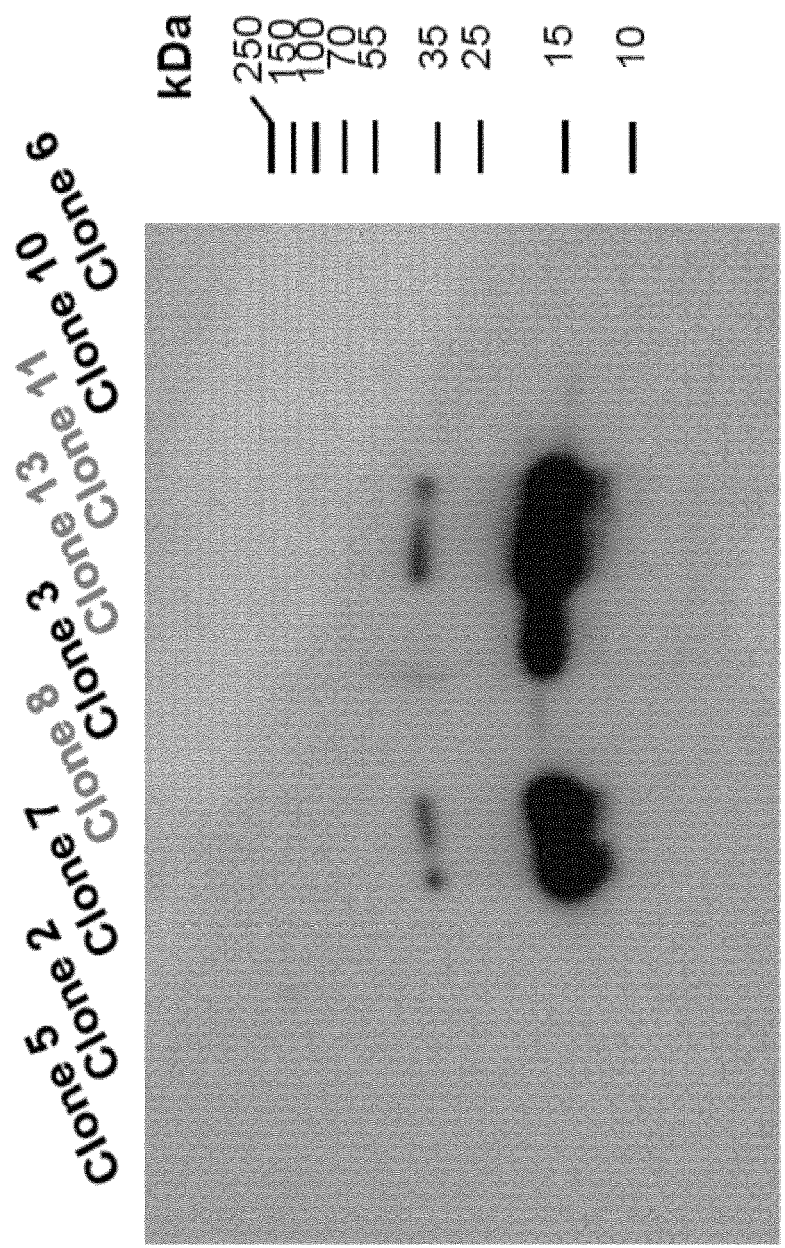
FIG. 2 shows in a Western blot the ability of monoclonal antibodies to bind to IL-3.

FIG. 2 shows the results of binding of antibody clones 2, 3, 5, 6, 7, 8, 10, 11 and 13. Binding to IL-3 at the given concentration was detected for clones 8, 11 and, to a lesser extent, for clone 13.

Example 4—Analysis of the IL-3 Affinity and Specificity of Monoclonal Antibodies a) Affinity of the Antibodies for IL-3

The affinity of the obtained antibodies for IL-3 was measured in an ELISA assay. ELISA plates were coated overnight with different concentrations (2 μg/ml, 0.66 μg/ml, 0.22 μg/ml, 0 μg/ml) of anti-human IL-3 antibody (RD, goat IgG anti-human IL-3 AF-203-NA). For each concentration, duplicates were used (2×12 wells). For this purpose, the first concentration (2 μg/ml) is diluted in PBS, further dilutions are made in PBS containing 2 μg/ml control goat IgG to keep the total concentration of IgG constant. Blocking with 2%

BSA is performed for 2 hours at room temperature, followed by 5 washing steps using PBS.

The wells are then incubated with hIL-3 (0.25 µg/ml in PBS) for 2 hours at room temperature, for the control group no hIL-3 is added. After five further washing steps with PBS, the wells are incubated overnight at 4° C. with serial (1:3) dilutions of antibodies clone 8 and 11 obtained in example 1, the antibodies being used in PBS buffer containing 2% BSA and with a starting concentration of 20 µg/ml.

After five further washing steps, bound antibody is detected using goat-anti-mouse-HRP antibody (1:500 in PBS with 2% BSA) and incubation for 1 hour at room temperature. After five further washing steps, ABTS (ROCHE, 1 mg/ml) is added as substrate and the optical density measured in a spectrometer at 405 nm.

Figure 3:
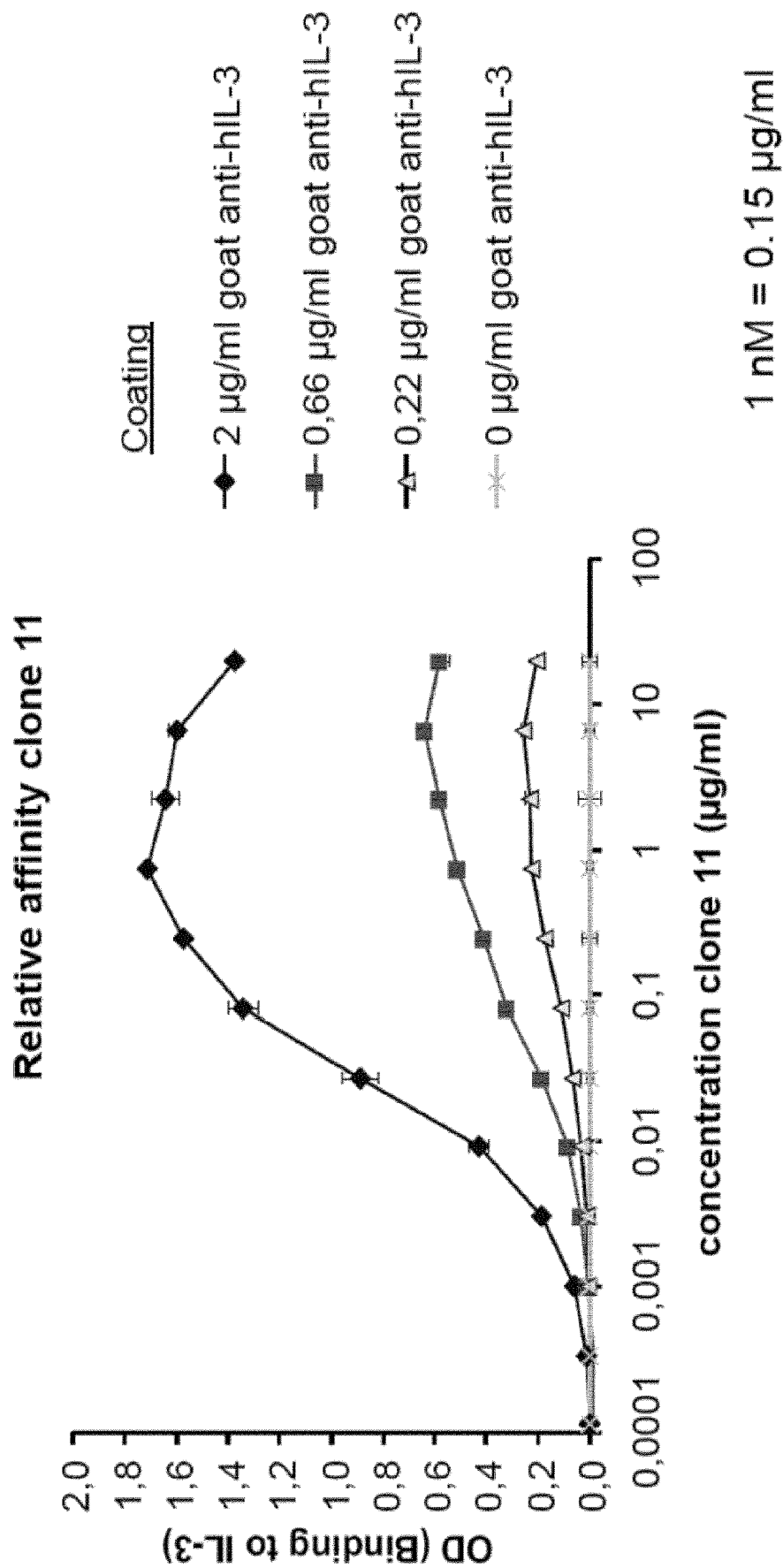
FIG. 3 shows the relative affinity of antibody clone 11 for IL-3 as determined by using varying amounts of the antibodies in ELISA assays for which different amounts of IL-3 were bound via goat anti-human-IL-3 antibodies to a solid surface via increasing amounts of coated goat anti-hIL-3 antibody.
Figure 4:
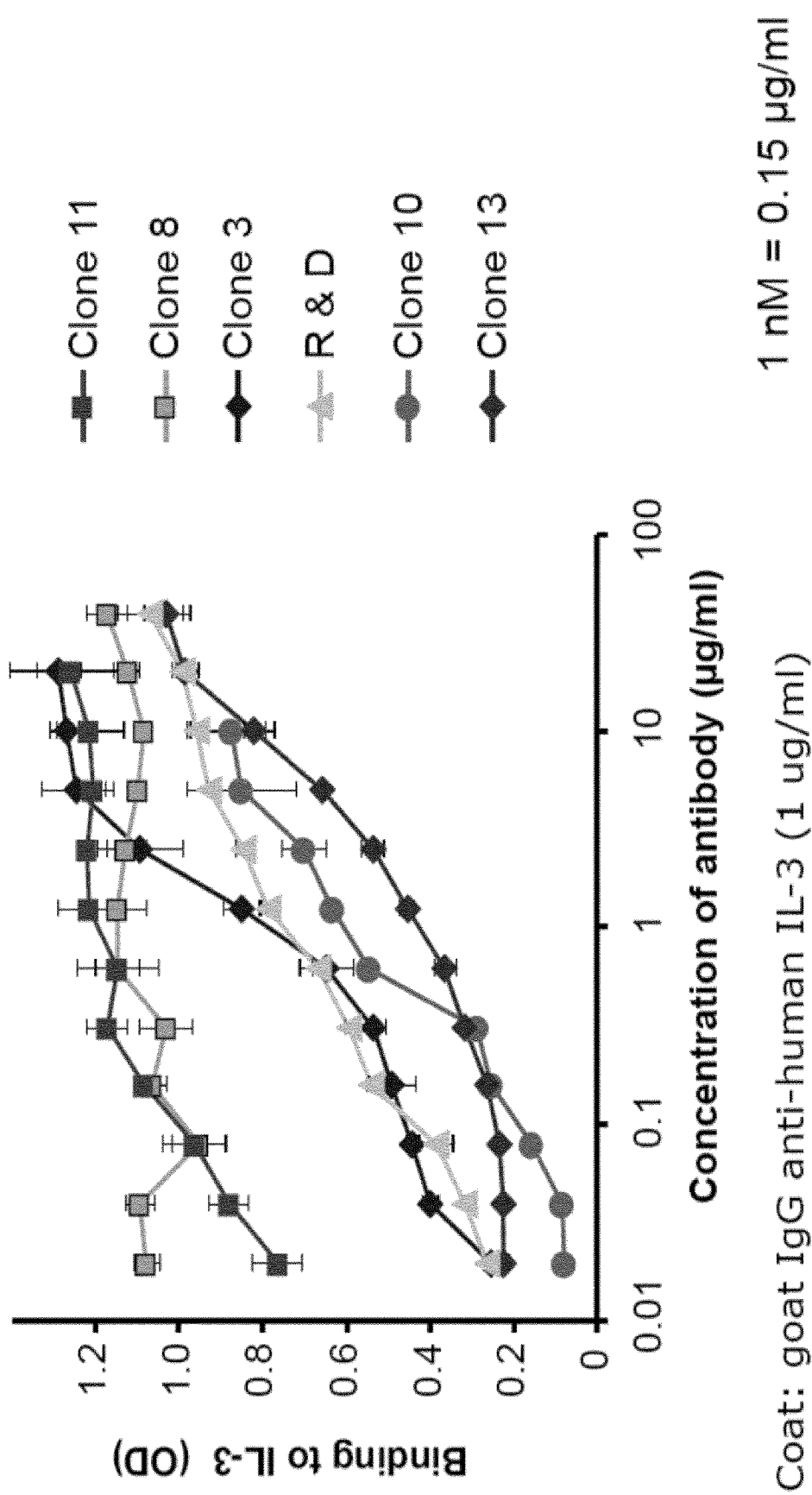
FIG. 4 shows the relative IL-3 affinity of antibodies determined using varying concentrations of antibodies at a constant amount of IL-3 which was bound to the solid phase in an ELISA assay.

Results are shown in FIG. 3 for antibody clone 11. Antibody clone 11 shows a high affinity for IL-3 in the assay. FIG. 4 shows the results of further tests including other antibodies. The tests were performed in the same manner as described, however, coating of the solid phase was performed using 1 µg/ml goat IgG anti-human IL-3 (see above) and different concentrations/dilutions of antibodies as shown in the figure.

b) Cross-Reactivity with Other Cytokines

To determine the usefulness of the obtained monoclonal antibodies for diagnostic assays, it is important to be able to exclude cross-reactivity with closely related cytokines which are also present in blood, plasma, serum or other body fluids of patients. To this end, wells of ELISA plates were coated by adding 100 µl/well of human IL-3 (1 µg/ml), GM-CSF (1 µg/ml) or IL-5 (1 µg/ml) in PBS. As negative control PBS was used (100 µl/well). For each tested antibody, different dilutions were tested mandatorily on a common plate with hIL-3, hGM-CSF, hIL-5 and PBS.

The cytokine coated plates were washed three times and blocking performed for 2 hours at room temperature using 2% BSA in PBS. After three further washing steps, antibodies clone 3.47.20, 8.36.38, 10.12.4, 11.14.6, 13.4.4 and just medium (RPM11640 containing 10% FCS) as control were added at a concentration of 40 µg/ml and 1:5 and 1:25 dilutions thereof in a volume of 100 µl/well and incubated for 1 hour at room temperature. On each plate a negative control is used.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

Figure 5:
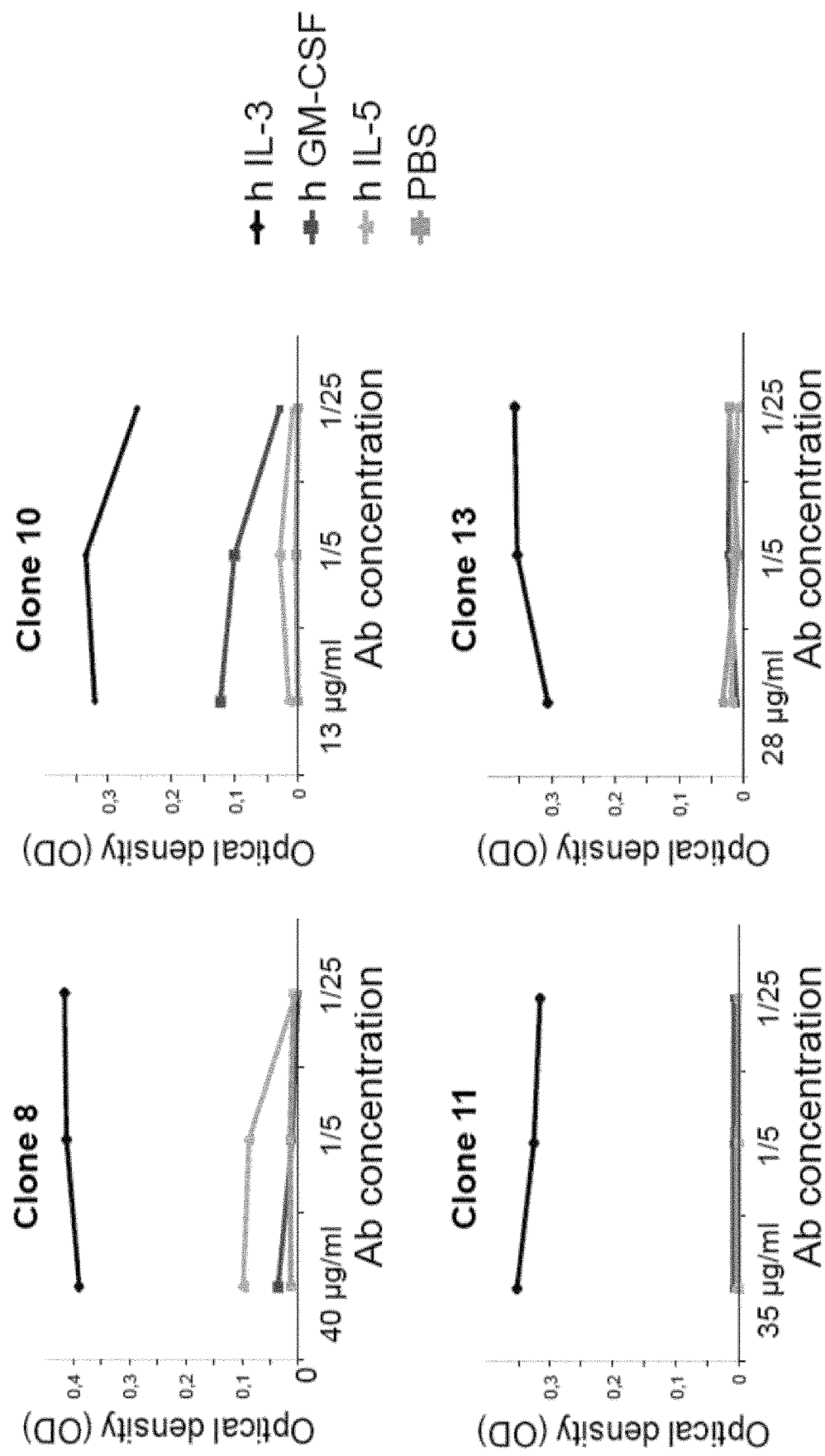
FIG. 5 shows the results of tests performed to detect a possible cross-reactivity of anti-IL-3 antibodies with other human cytokines. In the tests, binding of the antibodies to IL-3, GM-CSF and IL-5 was compared.
Figure 6:
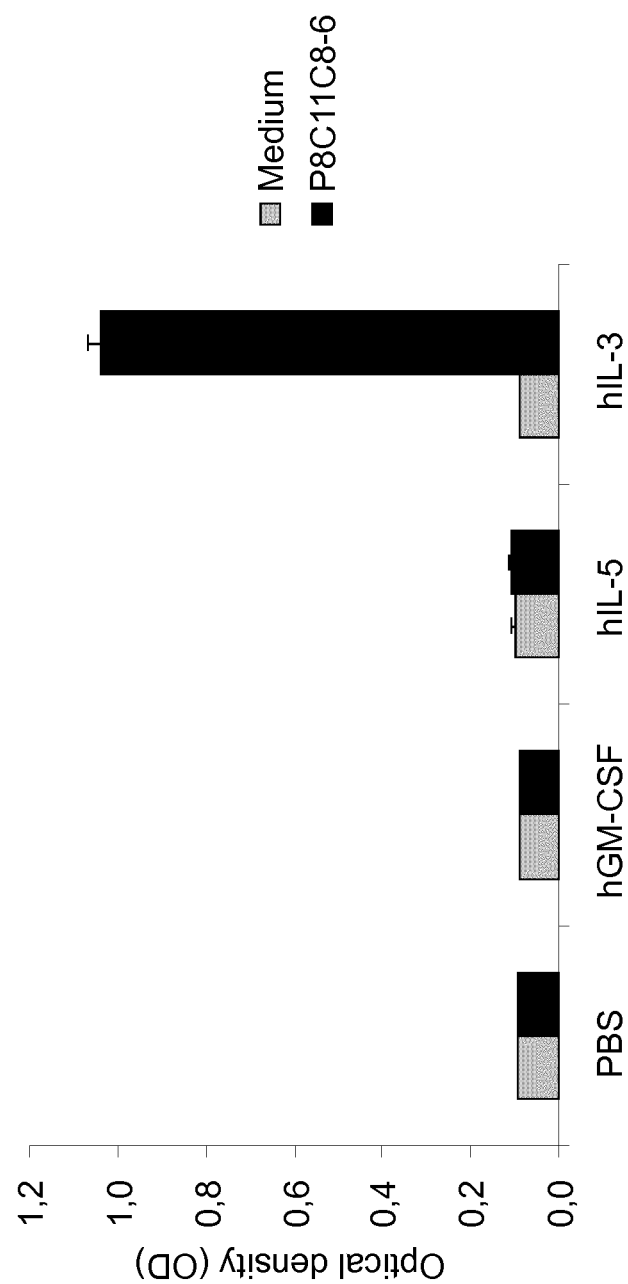
FIG. 6 shows that clone P8C11C8-6 does not exhibit cross-reactivity with human IL-5 or human GM-CSF. ELISA wells were coated overnight with PBS, human GM-CSF, human IL-5 or human IL-3 (1 µg/ml) in PBS. After washing and blocking with PBS/1% BSA (bovine serum albumin) clone P8C11C8-6 (40 µg/ml) or medium was applied for 1 h at room temperature. After washing a secondary HRP-labelled rabbit anti-mouse polyclonal antibody (P260, DakoCytomation) was applied. After washing a color substrate reaction was performed with ABTS and optical density was measured. The results shown in FIG. 6 were obtained by using human IL-3 expressed by insect cells (Recombinant Human IL-3 (carrier-free) Cat. #578002 from Biolegend). Therefore the human IL-3 peptide was glycosylated.

The results are shown in FIG. 5 indicating some weak cross-reactivity for clones 8 and 10, but no significant cross-reactivity for clones 11 and 13. FIG. 6 shows the results obtained with clone P8C11C8-6.

c) Cross-Reactivity with IL-3 from Other Species

As a further property of the monoclonal antibodies, their cross reactivity with IL-3 from other species was determined. For a respective assay, the wells of ELISA plates were coated with human, murine, rat and rhesus IL-3 (1 µg/ml) in PBS as well as with PBS as background with 100 µl/well and incubated overnight in a refrigerator. For each antibody, different dilutions were tested mandatorily on a common plate with hIL-3, murine IL-3, rat IL-3, rhesus IL-3 and PBS negative control.

Figure 7:
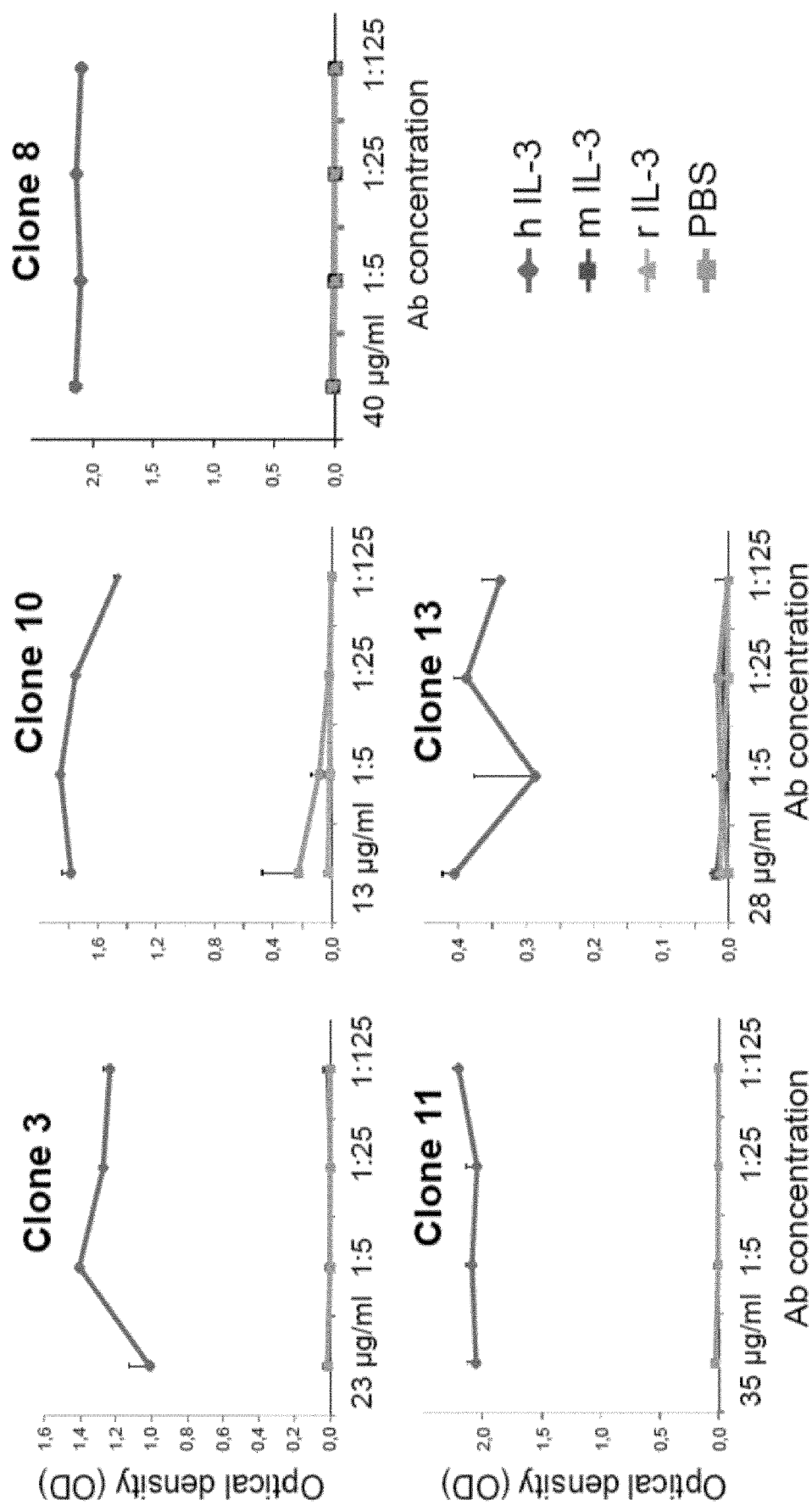
FIGS. 7-9 show the results of tests performed to detect possible cross-reactivity of the various anti-IL-3 antibodies with IL-3 from other species.
Figure 8:
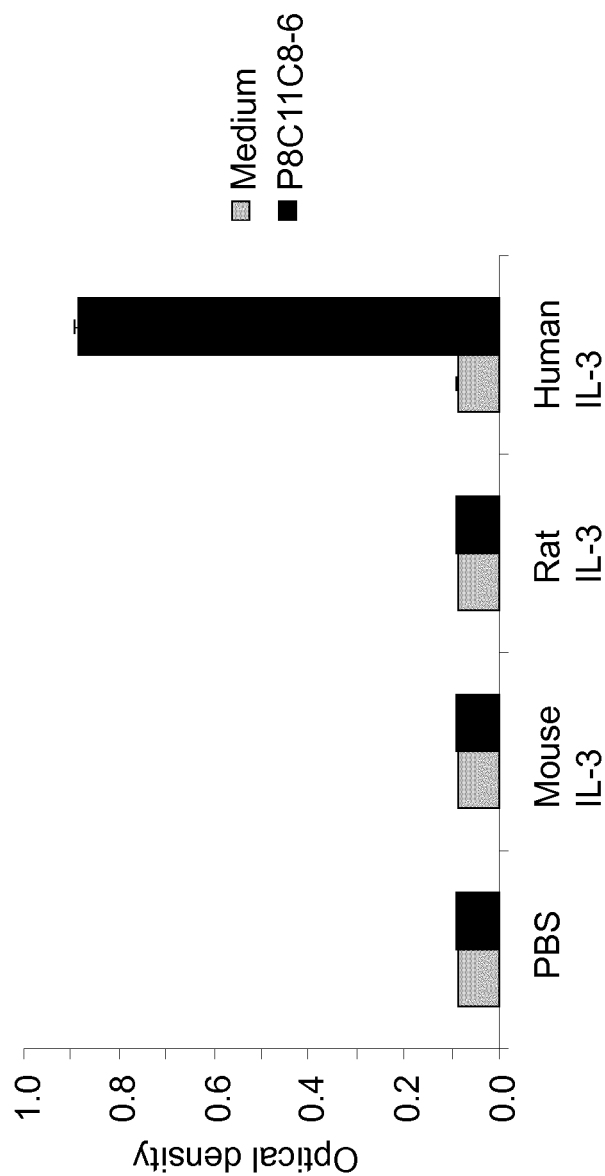
Figure 9:
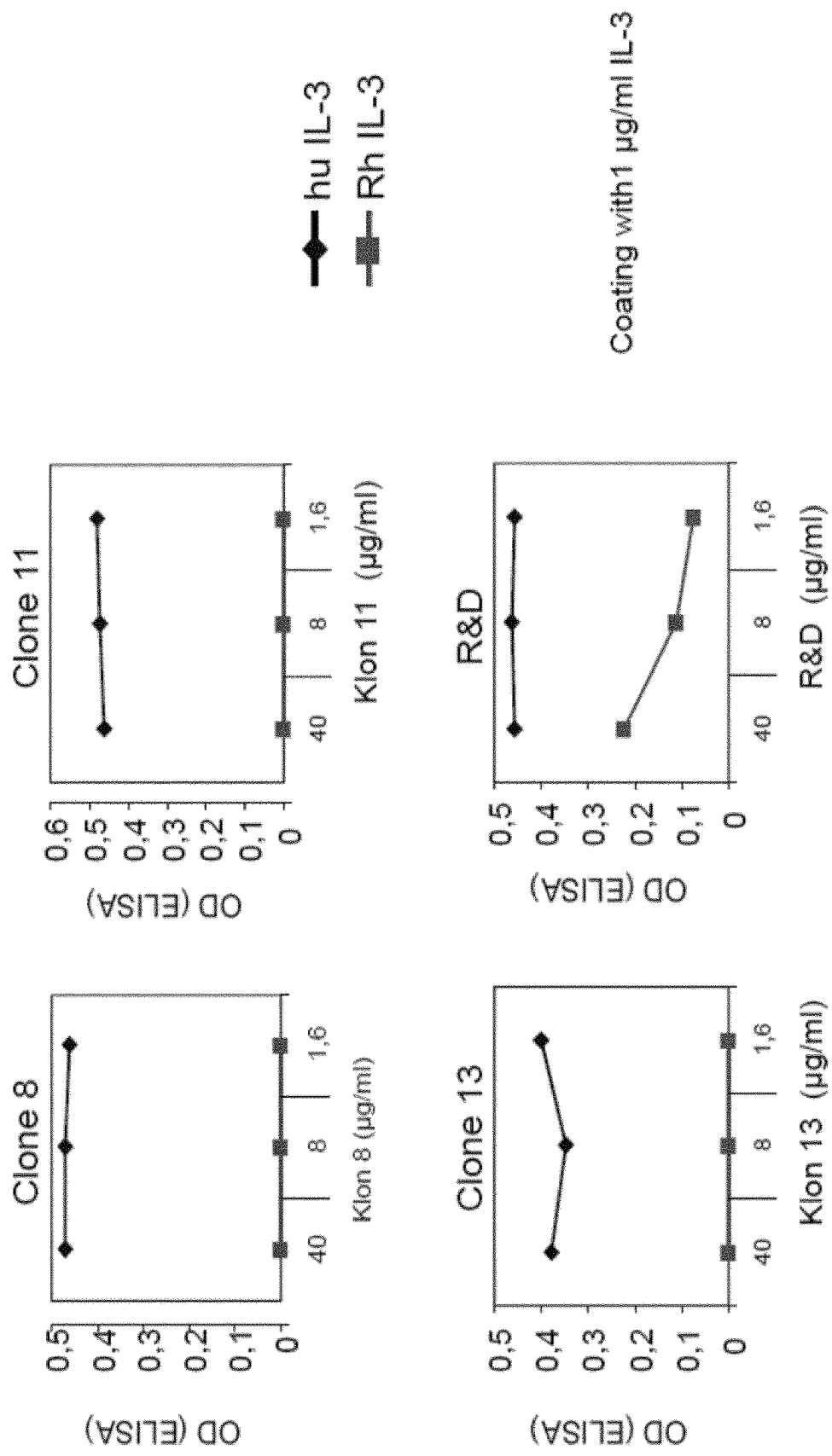

The IL-3 coated plates were washed three times and blocking performed for 2 hours at room temperature with 2% BSA in PBS. After three washing steps, antibody clones 3.47.20, 8.36.38, 10.12.4, 11.14.6, 13.4.4 in certain concentrations as indicated in FIGS. 7 and 9, and 1:5, 1:25 and 1:125 dilutions thereof were added at volumes of 100 µl/well. R&D monoclonal anti-IL-3 antibody clone 4806 (R&D Systems, Inc., catalogue No. MAB203) was used (100 µl/well) in concentrations of 40 µg/ml, 20 µg/ml, 10 µg/ml, 5 µg/ml and 2.5 µg/ml and, as negative control, medium (100 µl/well) without antibody (RPMI 1640 containing 10% FCS) was used. On each plate a negative control was used. FIG. 8 shows the results obtained with clone P8C11C8-6.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

Results are shown in FIGS. 7-9, as mentioned above, indicating that albeit a faint cross reactivity of clone 10, none of the antibodies of Example 1 showed detectable cross-reactivity. The R&D antibody on the other hand, showed some cross-reaction with rhesus IL-3.

Example 5—Analysis of the Blocking Properties of Monoclonal Antibodies

To analyze the ability of antibodies obtained according to Example 1 to block IL-3 activity, several different experiments were performed.

a) Analysis of the Ability of Antibodies to Block IL-3 Based on the IL-3 Dependent Growth of TF1 Cells:

TF1 cells are human erythroblasts and the cell line has been established by T. Kitamura in 1987 from bone marrow of a 35 year old male Japanese suffering from severe pancytopenia. Growth of TF1 cells is completely dependent on the presence of IL-3 or GM-CSF. Thus, a test based on the cell proliferation of TF1 cells can be used to determine blocking of the IL-3 activity which in turn leads to a decrease or even a complete inhibition of the growth of TF1 cells. For such a test, a MTT-cell-proliferation assay is performed to determine the viability of cells based on the activity of the mitochondrial dehydrogenase. The dehydrogenase's substrate MTT (3-(4,5-dimethylthiazol-2-yl)-2,5-diphenyl tetrazolium bromide) which shows a yellow color in solution, is cleaved at the tetrazolium ring by the enzymatic activity leading to formation of purple MTT formazane crystals. Such crystals can be dissolved in isopropanol, the purple solution measured in a spectrometer and the results correlated to the amount of viable TF1 cells.

Cultivation of TF1 Cells:

TF1 cells were grown in suspension in a culture medium (RPMI-1640 containing 10% FCS (HIA), P/S and glutamine (1:100) and supplemented with either 5 ng/ml of IL-3 or 5 ng/ml of GM-CSF) and split 1:4 every third day.

For storage, cells were transferred from a cell culture bottle to 50 ml or 15 ml cell culture flasks (BD Falcon™). After centrifugation at 1400 rpm for 5 minutes at room temperature, the supernatant is completely removed. Cells are resuspended in culture medium (RPMI-1640 containing 10% FCS (HIA)+P/S+glutamine+5 ng/ml IL-3) and 5% DMSO and 1.5 ml aliquots are filled into vials. The cells are pre-frozen in a freezing container in a freezer at −80° C. and after 1-2 days transferred to a liquid nitrogen storage tank.

Blocking Experiment:

TF-1 cells that had been split every third day according to the protocol described above are split 1:2 in culture medium containing 5 ng/ml human IL-3 on the day before the experiment is performed.

For the experiment, cells are centrifuged for 5 minutes at 1600 rpm at room temperature. The culture medium is removed and the cells washed twice in RPMI medium before cells are resuspended in 1 ml RPMI-1640+10% FCS (HIA)+P/S+glutamine (1:100), counted and supplemented with buffer to a final concentration of $1 \times 10^5$ cells/ml.

In a 96-well-plate, 10,000 cells in 100 µl medium (RPMI+ 10% FCS+P/S+glutamine) are provided to each well. 100 µl of IL-3 which has been preincubated with monoclonal antibody of Example 1 for 60 min at 37° C. For the preincubation different final concentrations of antibody and IL-3 are used. To obtain such final concentrations, the concentration of the antibody and IL-3 solutions needs to be twice the amount of the end concentration. After 5 days of incubation at 37° C. and addition of 5% $CO_2$, 100 µl of medium are removed from each well and 10 µl MTT solution (LCG Standard-ATCC) are added to each well and the plates incubated for another 4 hours in an incubator at 37° C. and 5% $CO_2$. After this further incubation, 100 µl MTT solvent is added and the contents of the wells mixed carefully. After an overnight incubation, optical density is determined at 570 and 690 nm and the number of viable cells calculated therefrom.

Experiments were performed for antibody clones 8.36.38 (clone 8), 11.14.6 (clone 11) 13.4.4 (clone 13), a commercially available anti-hIL-3 antibody clone 4806 (RD catalogue No. MAB203) and a mouse IgG1 kappa MOPC 21 antibody (without azide) as isotype control (Sigma-Aldrich).

Figure 10:
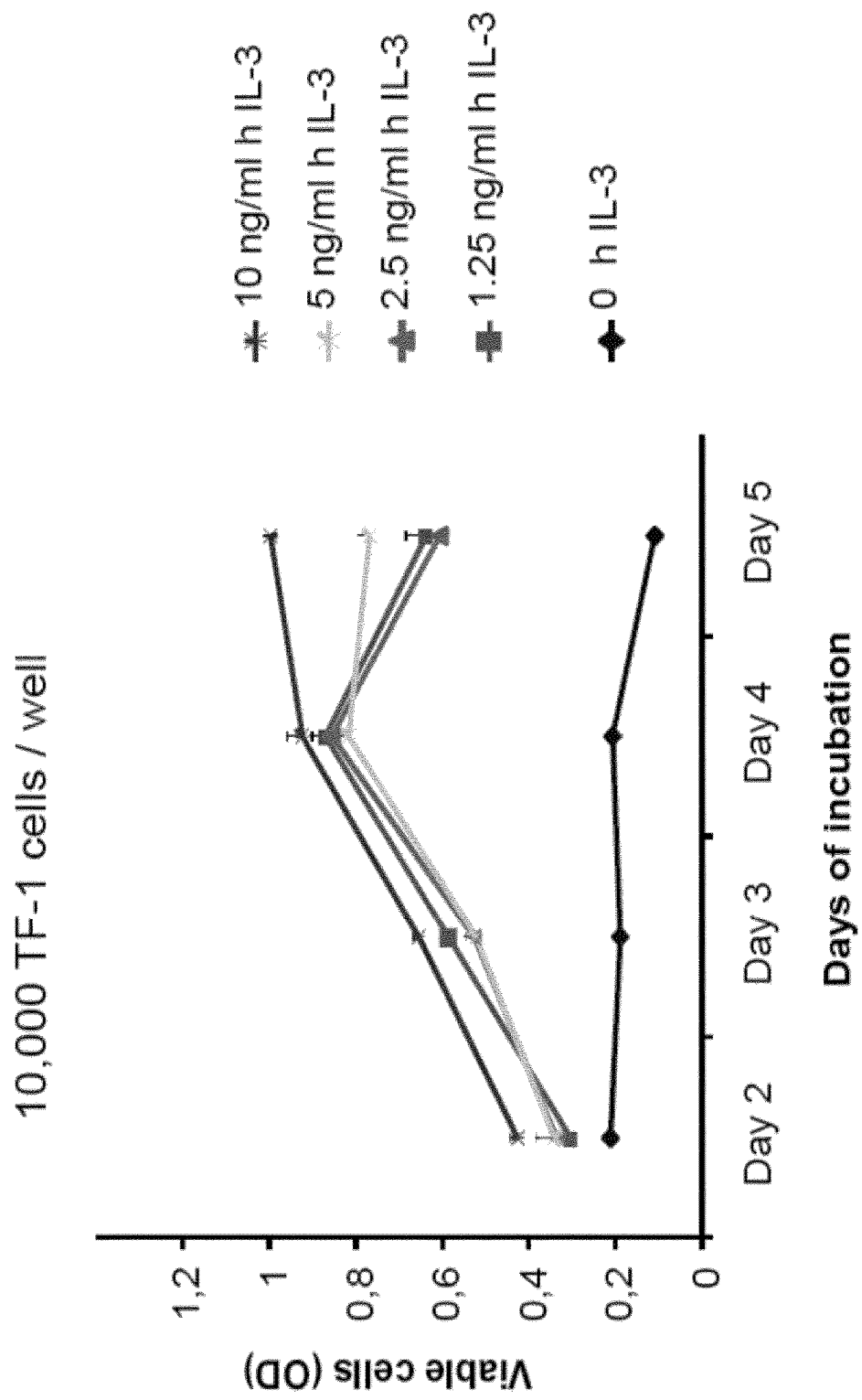
FIG. 10 shows the IL-3 dependent growth of TF1 cells wherein viable cells do not propagate in the absence of IL-3 and cell growth can be shown to be dependent on the amount of IL-3 in the growth medium.
Figure 11:
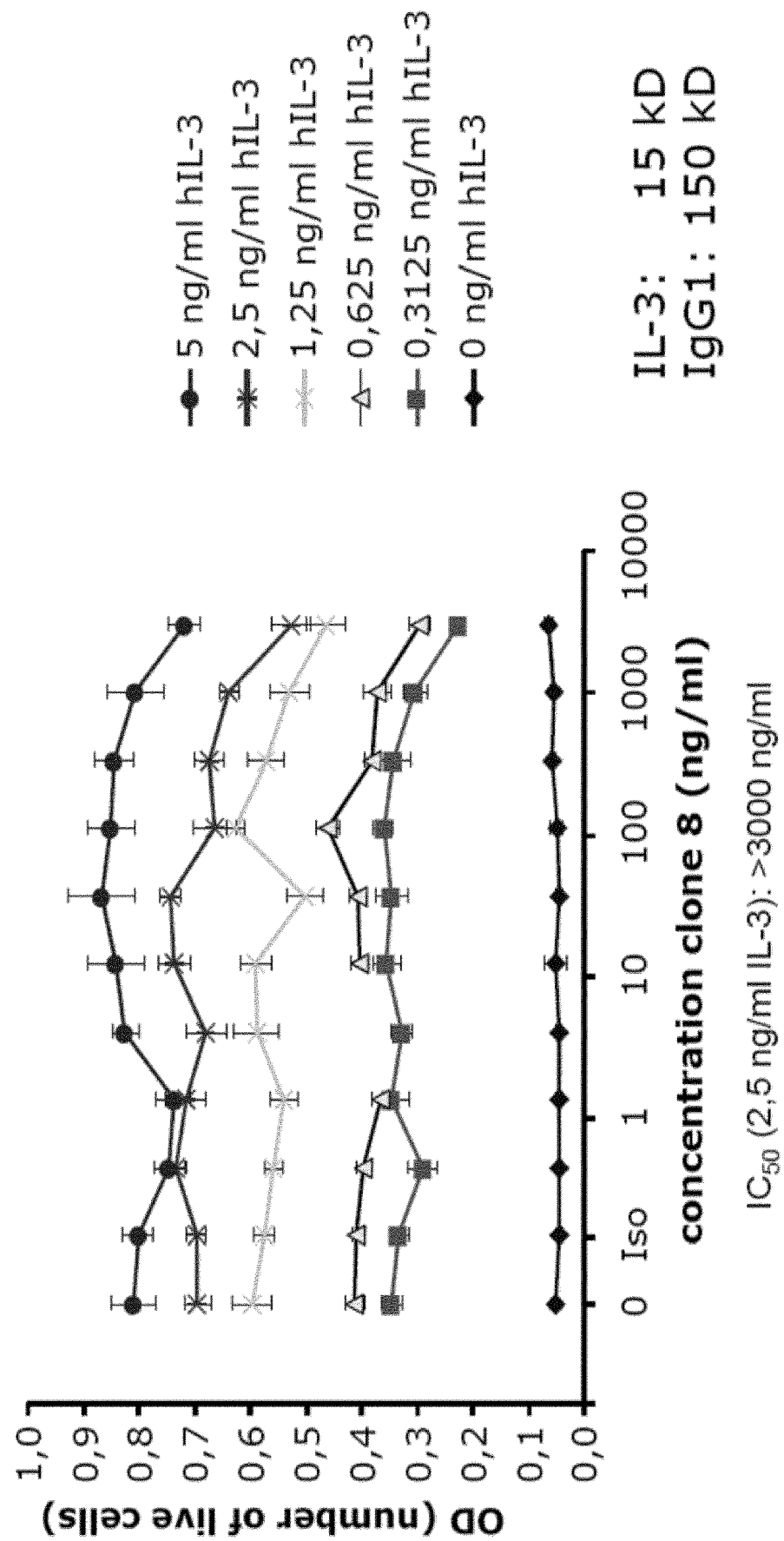
FIGS. 11 to 14 show the ability of various monoclonal antibodies—including a commercially available anti-IL-3 antibody—to inhibit the IL-3 dependent growth of TF1 cells. For differing concentrations of hIL-3 present in the cell growth medium, the effect of the antibodies was tested showing distinct inhibition of cell growth for antibodies clone 11, clone 13 and the commercially available R&D anti-IL-3 antibody, whereas clone 8 had only a minor effect. The human IL-3 used was obtained from Peprotech, and expressed by *E. coli*. Therefore the human IL3-used was a non-glycosylated IL-3 peptide.
Figure 12:
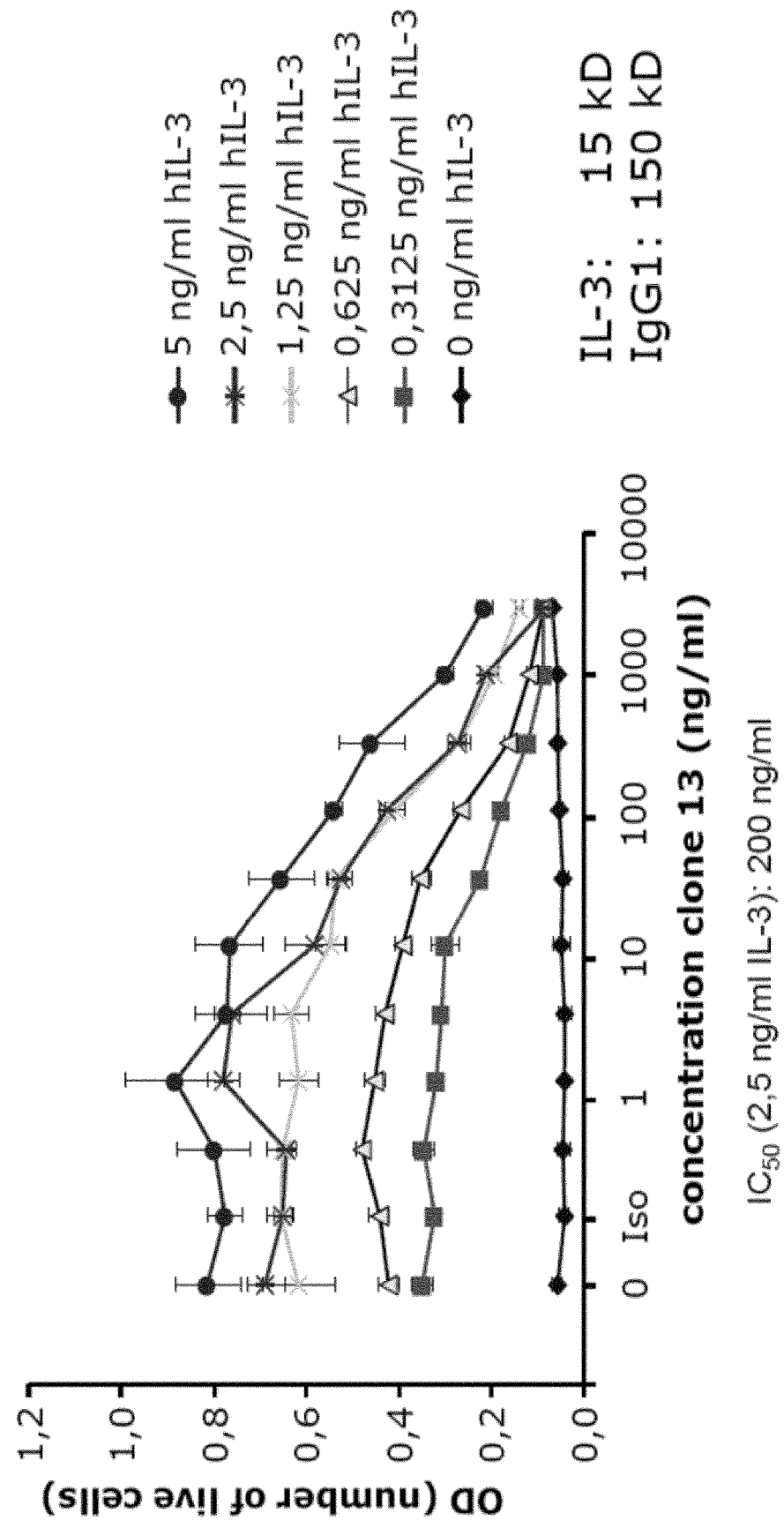

The general influence of IL-3 on the growth of TF1 cells is shown in FIG. 10. Results for different amounts of IL-3 with and without different concentrations of mAbs are shown in FIGS. 11 to 14.

b) Analysis of a Possible Influence of Anti-IL-3 Antibodies on the GM-CSF Dependent Growth of TF1 Cells As mentioned above, growth of TF1 cells is dependent on the presence of IL-3 or GM-CSF. As shown in Example 5a, anti-IL-3 antibodies have a negative effect on the growth of TF1 cells. IL-3 binds to the IL-3 receptor which is comprised of an alpha chain of 70 kDa and a beta chain of about 130 kDa. The same beta chain is also present on receptors for IL-5 and GM-CSF. Therefore, in another experiment it was tested whether anti-IL-3 antibodies also influence the growth of TF1 cells in the presence of GM-CSF. For this purpose, the experiment described above was repeated adding GM-CSF, IL-3 and mixtures thereof preincubated with the anti-IL-3 antibodies to the culture medium of TF1 cells. A control without GM-CSF and IL-3 was included.

Figure 15:
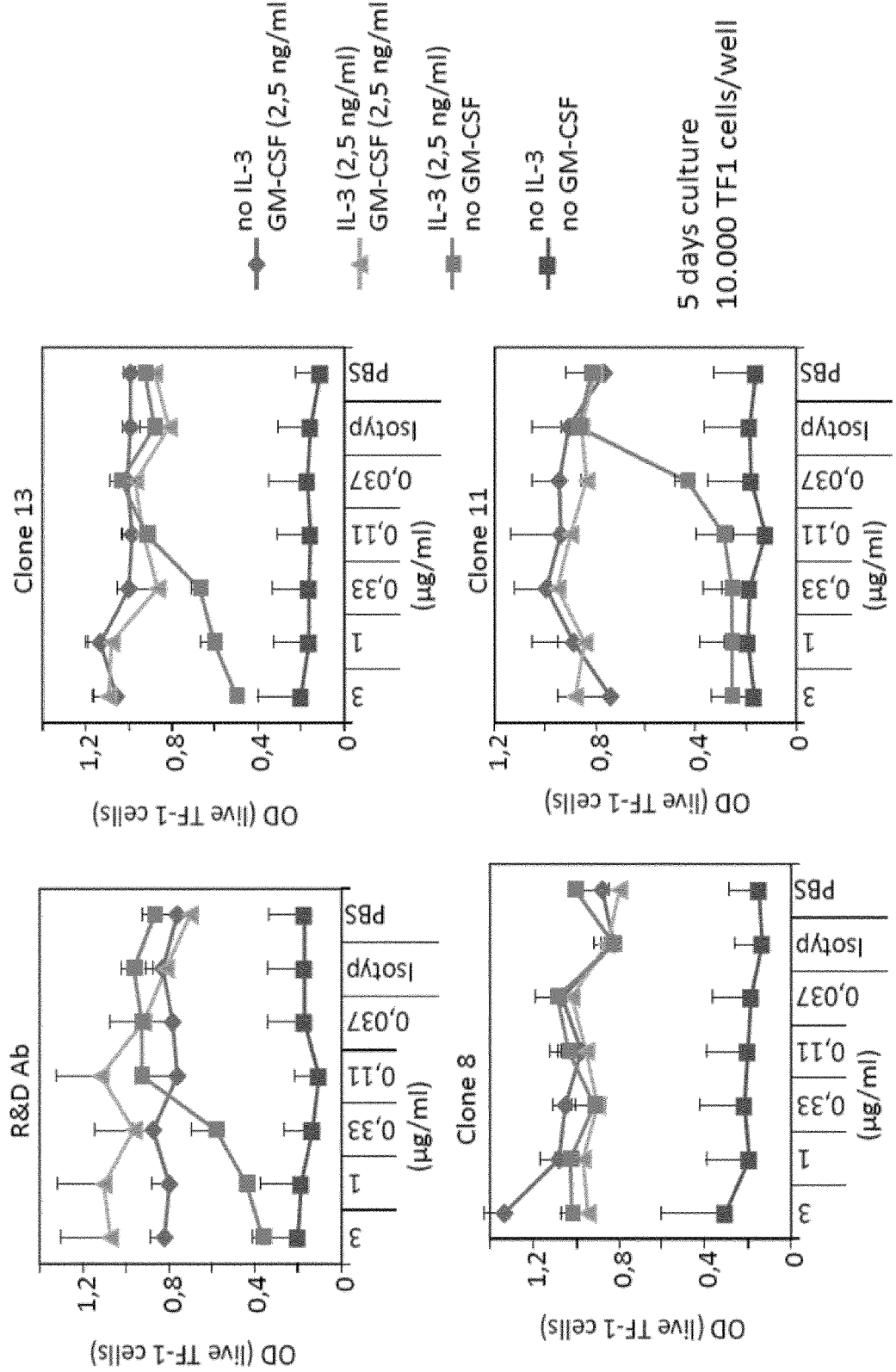
FIG. 15 shows the effect of various antibodies (clone 8, clone 11, clone 13 and R&D) and different concentrations thereof in the medium on the growth of TF1 cells in the presence of IL-3, GM-CSF or a combination thereof, or in the absence of these cytokines. None of the antibodies showed a marked inhibitory effect on the growth of TF1 cells in the presence of GM-CSF whereas, again, clone 11 and at a higher concentration also clone 13 and the R&D antibody clearly inhibited the IL-3 effect on the growth of TF1 cells. The human IL-3 used was obtained from Peprotech, and expressed by *E. coli*. Therefore the human IL-3 used was a non-glycosylated IL-3 peptide.
Figure 16:
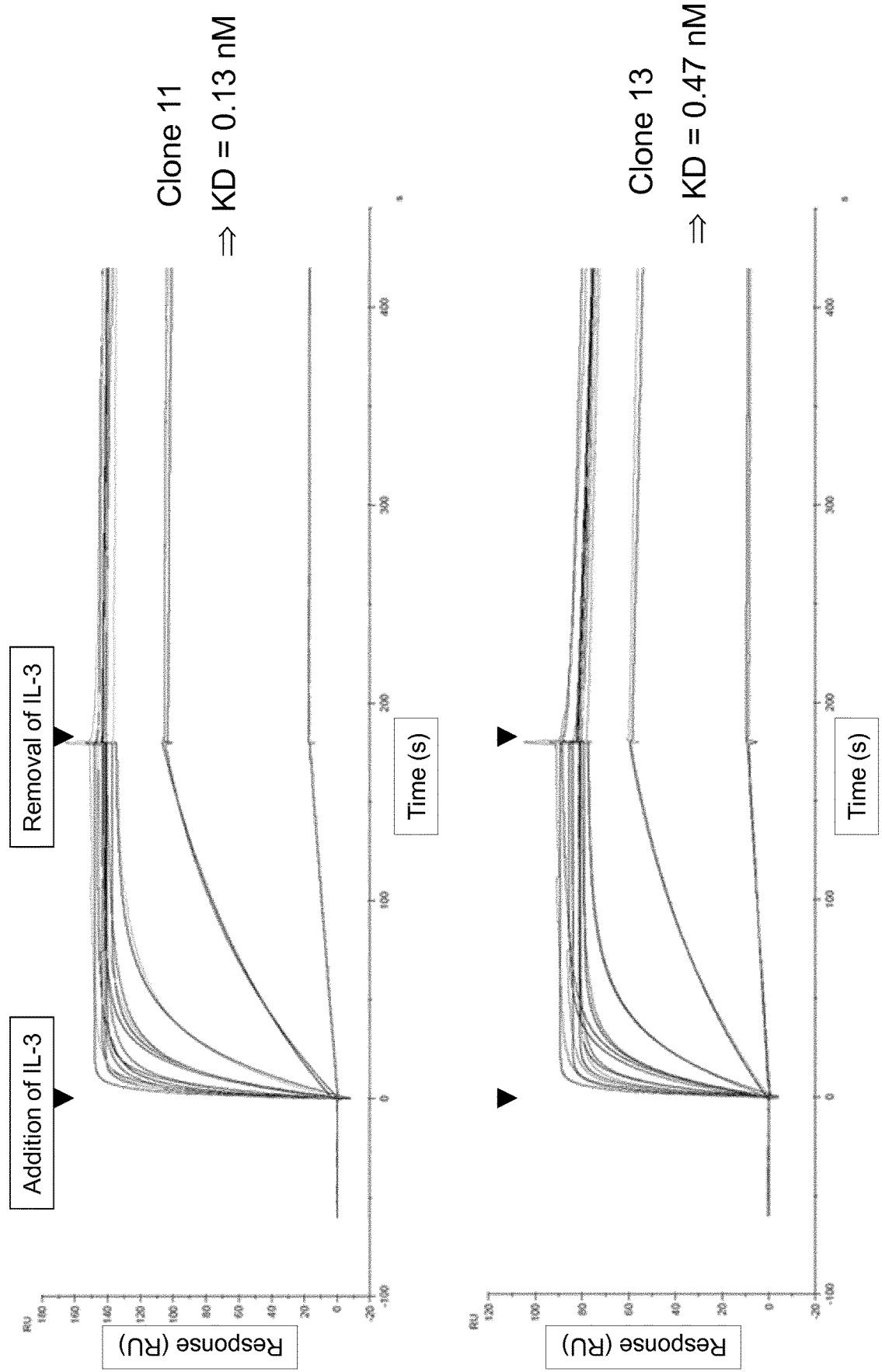
FIG. 16 shows a Biacore-Analysis of anti-IL-3 clone 11 and clone 13.

The results of the tests in view of the blocking of this influence and amounts of GM-CSF and antibodies, respectively, used in this example are shown in FIG. 15 indicating that none of the tested antibodies had a blocking effect on GM-CSF and its growth induction toward TF1 cells.

c) Analysis of the Ability of Anti-IL-3 Antibodies to Inhibit the IL-3 Induced Upregulation of CD203c and CD11b on Basophils and HLA-DR on pDCs Human basophilic granulocytes show an IL-3 induced upregulation of CD203c and CD11b. In this example, it was determined whether anti-IL-3 antibodies are also able to inhibit the effect of IL-3 in this regard.

Figure 17:
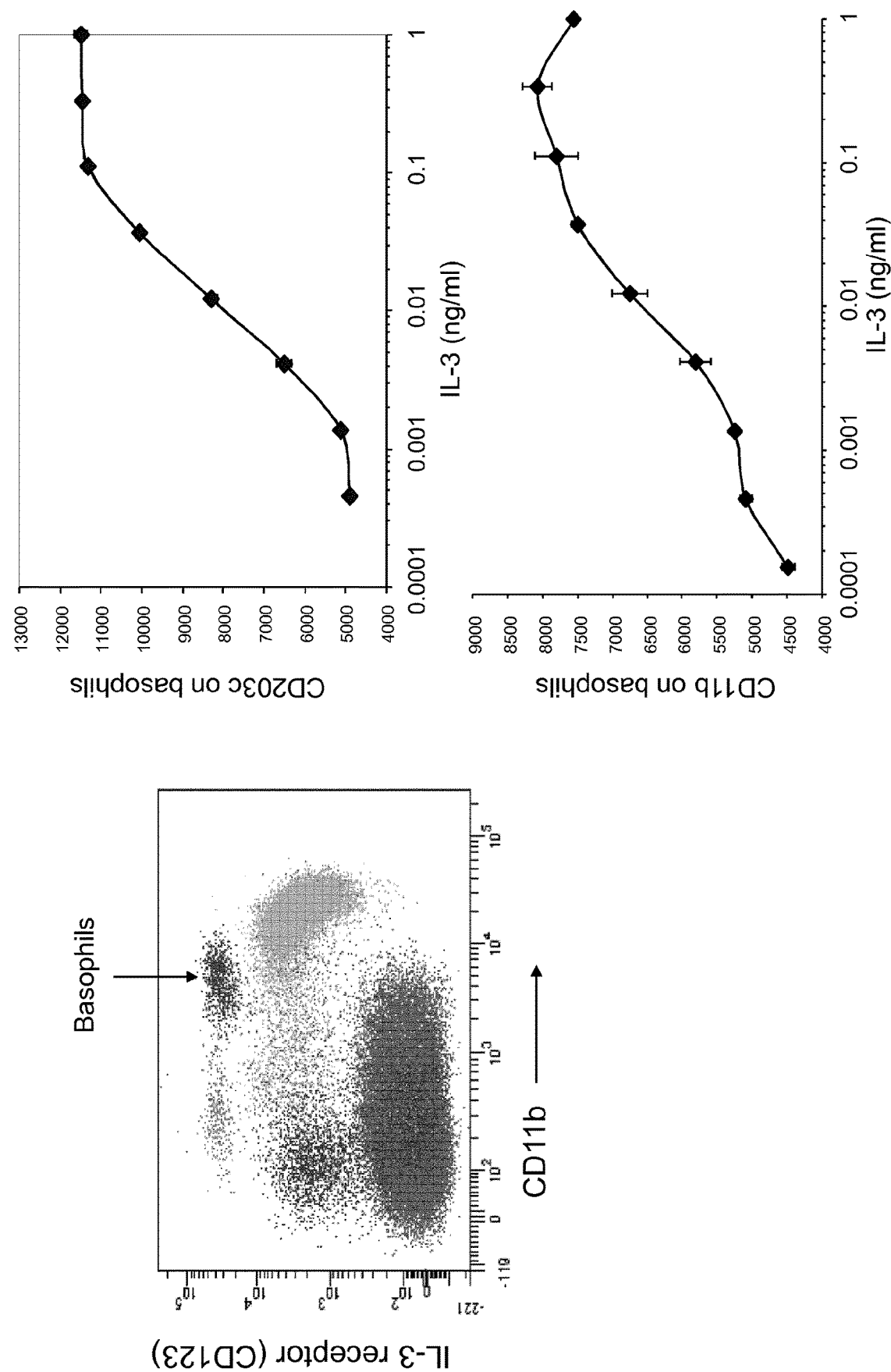
FIG. 17 shows IL-3 induced upregulation of CD203c and CD11b on basophils.
Figure 18:
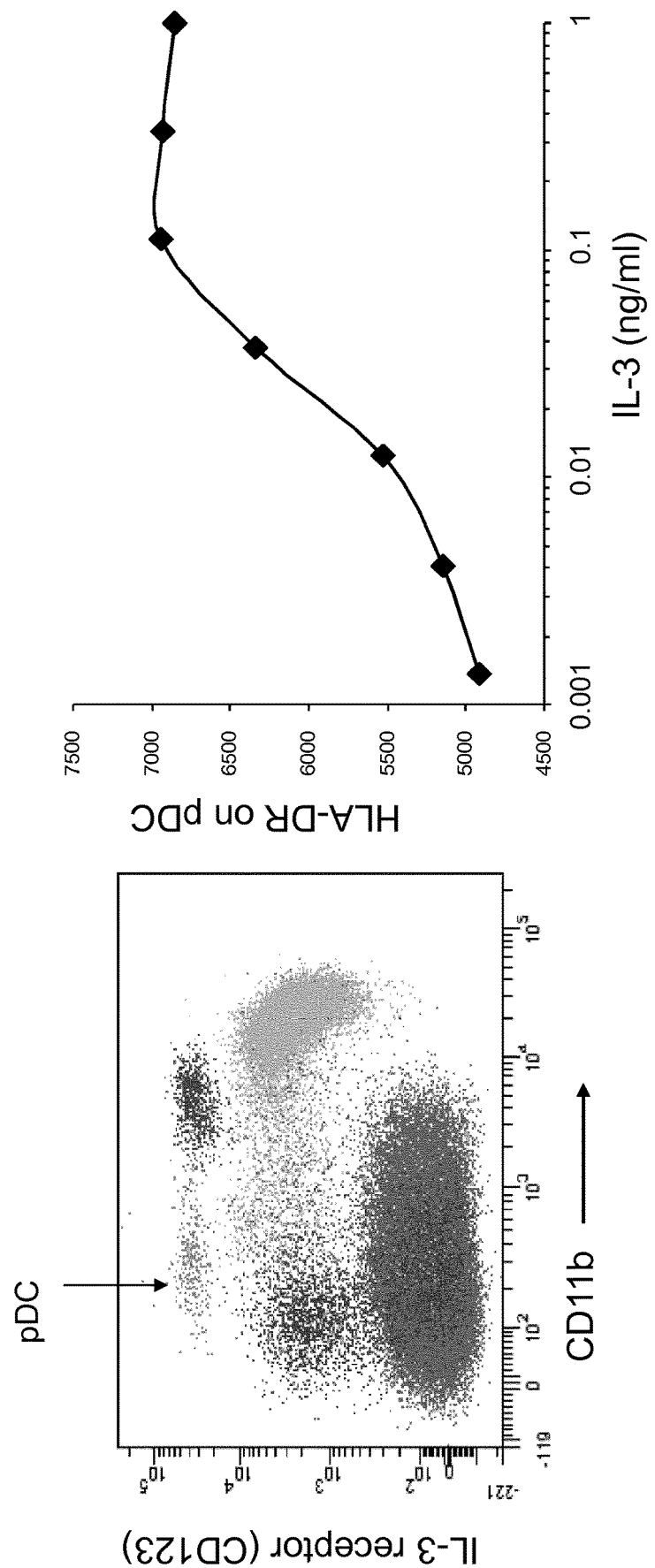
FIG. 18 shows IL-3 induced upregulation of HLA-DR on plasmacytoid dendritic cells (pDC).

Flow cytometric detection of basophils in fresh human EDTA blood stained with antibodies against CD11b, CD203c, CD123 and HLA-DR is shown on the upper left of FIG. 17. Flow cytometric detection of plasmacytoid dendritic cells (pDC) in fresh human EDTA blood stained with antibodies against CD11b, CD203c, CD123 and HLA-DR is shown on the left. Fresh human EDTA blood was incubated for 1 h at 37° C. with various concentrations of IL-3 of FIG. 18.

To analyze the neutralizing capacity of monoclonal antibodies against human IL-3 on primary human cells the IL-3 induced upregulation of CD203c and CD11b or the IL-3 induced downregulation of CD131 on basophils (see FIG. 17 on the right, FIGS. 34 and 35) and the IL-3 induced upregulation of HLA-DR on human pDC (see FIG. 18) were studied. All assays were performed with fresh EDTA blood.

Fresh human EDTA blood was incubated for 1 h at 37° C. with various concentrations of IL-3. Cells were then stained with antibodies against CD11b, CD203c, CD123, CD131, and HLA-DR and analyzed by flow cytometry (shown on the right of FIGS. 17 and 18, and in FIGS. 34 and 35).

Very surprisingly, it was found that the ability of anti-IL-3 antibodies to neutralize IL-3 effects on TF1 cells does not at all correlate with the ability to neutralize the IL-3 effects on primary human cells.

Figure 13:
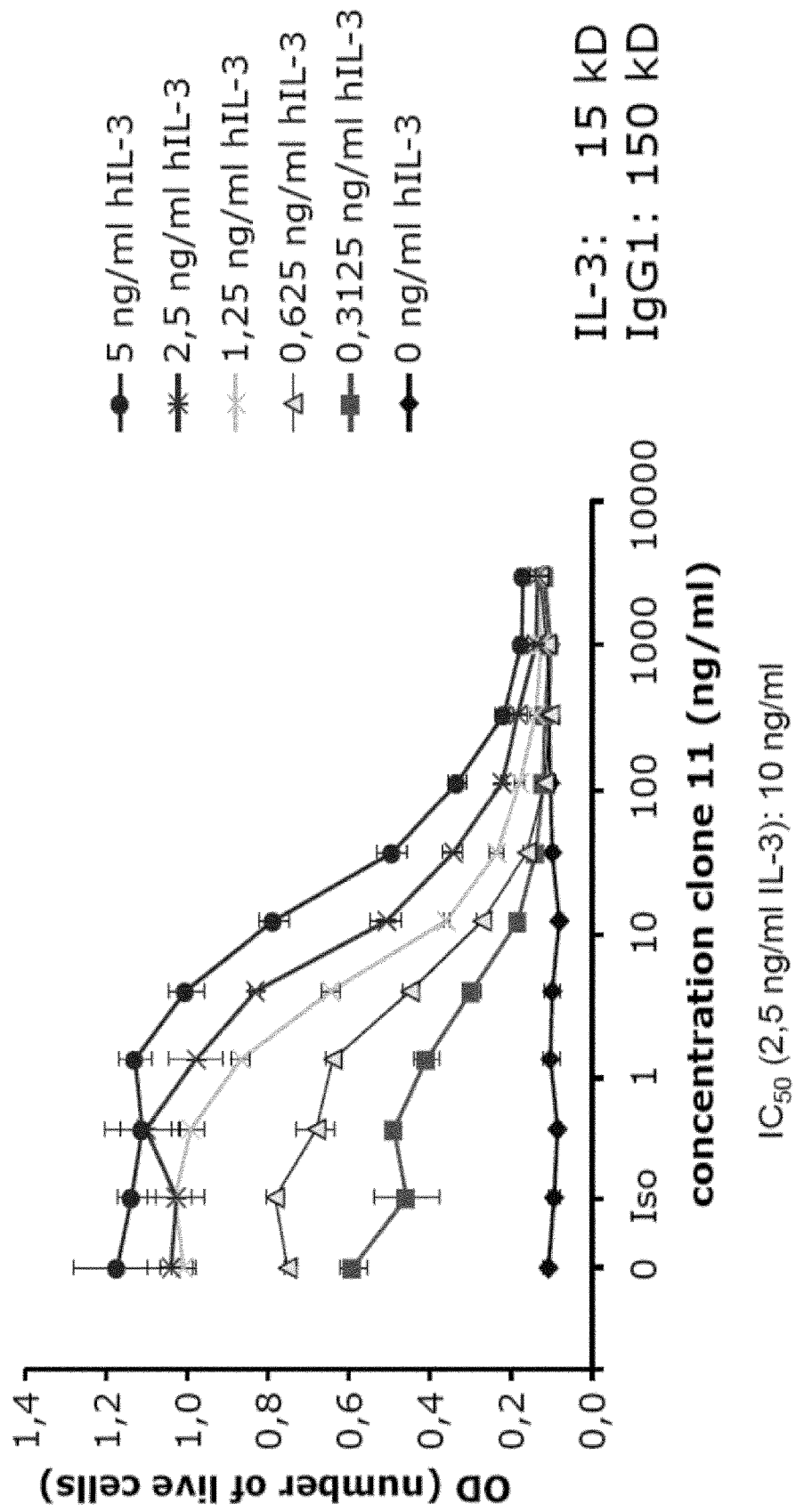
Figure 14:
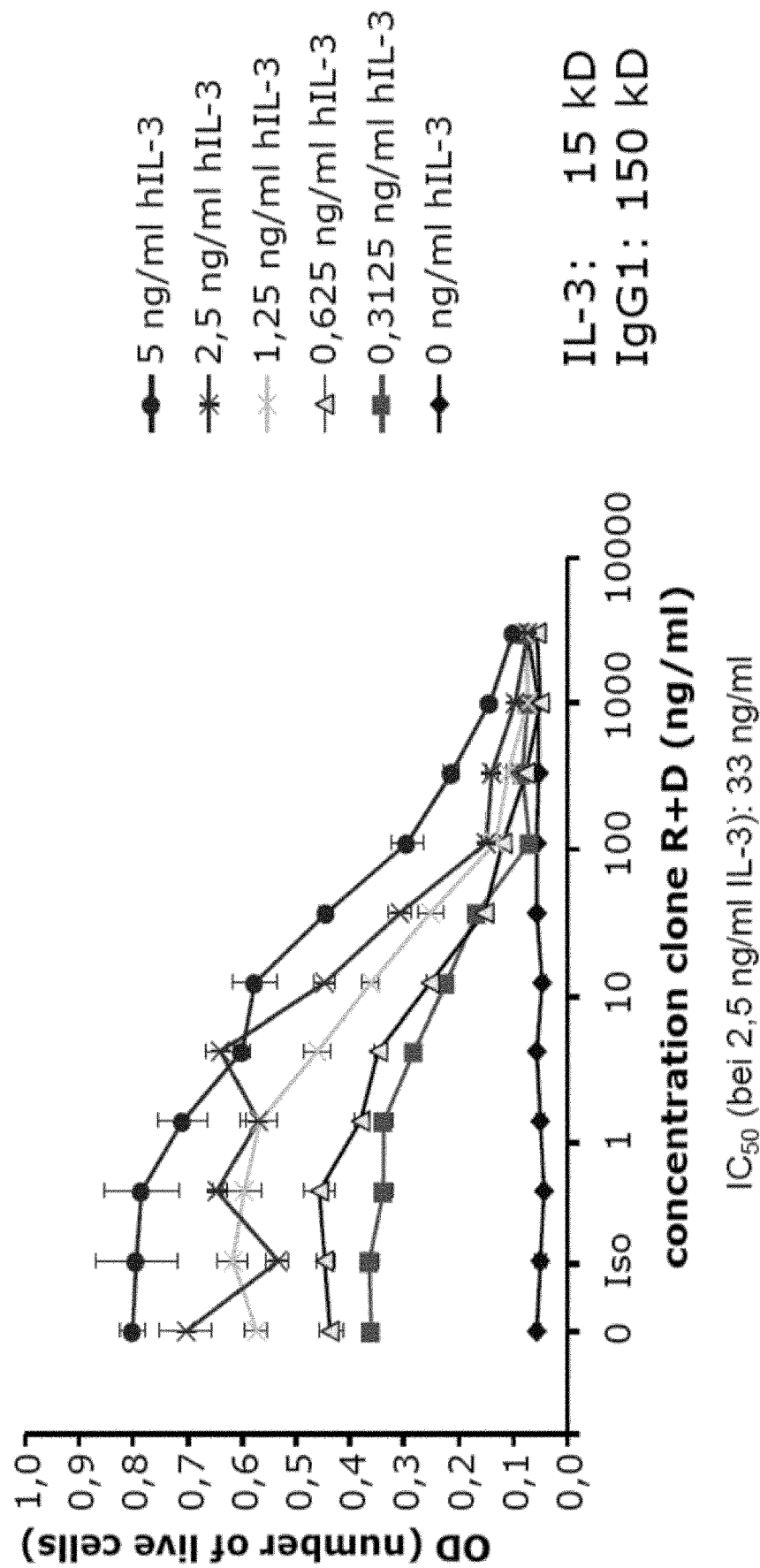
Figure 19:
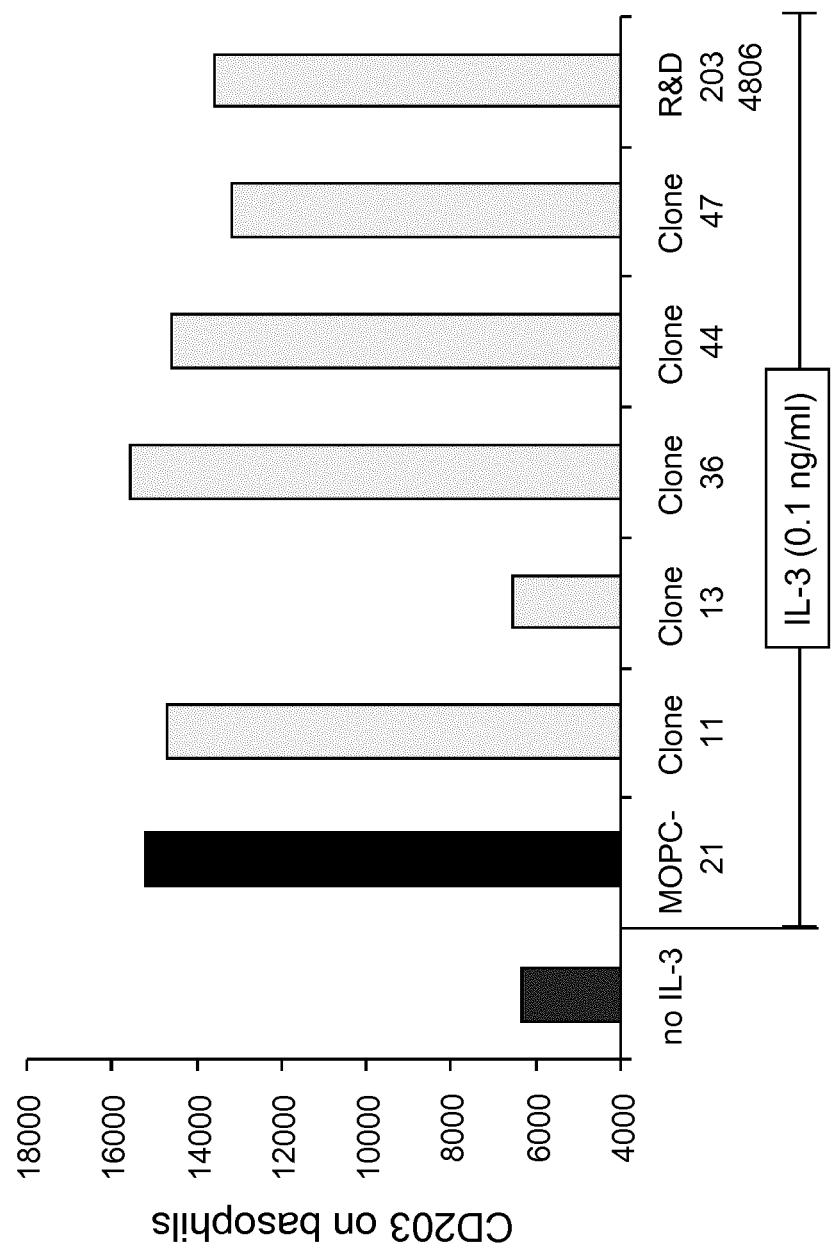
FIG. 19-21 show effects of antibodies on IL-3 induced upregulation of CD203 on basophils.
Figure 20:
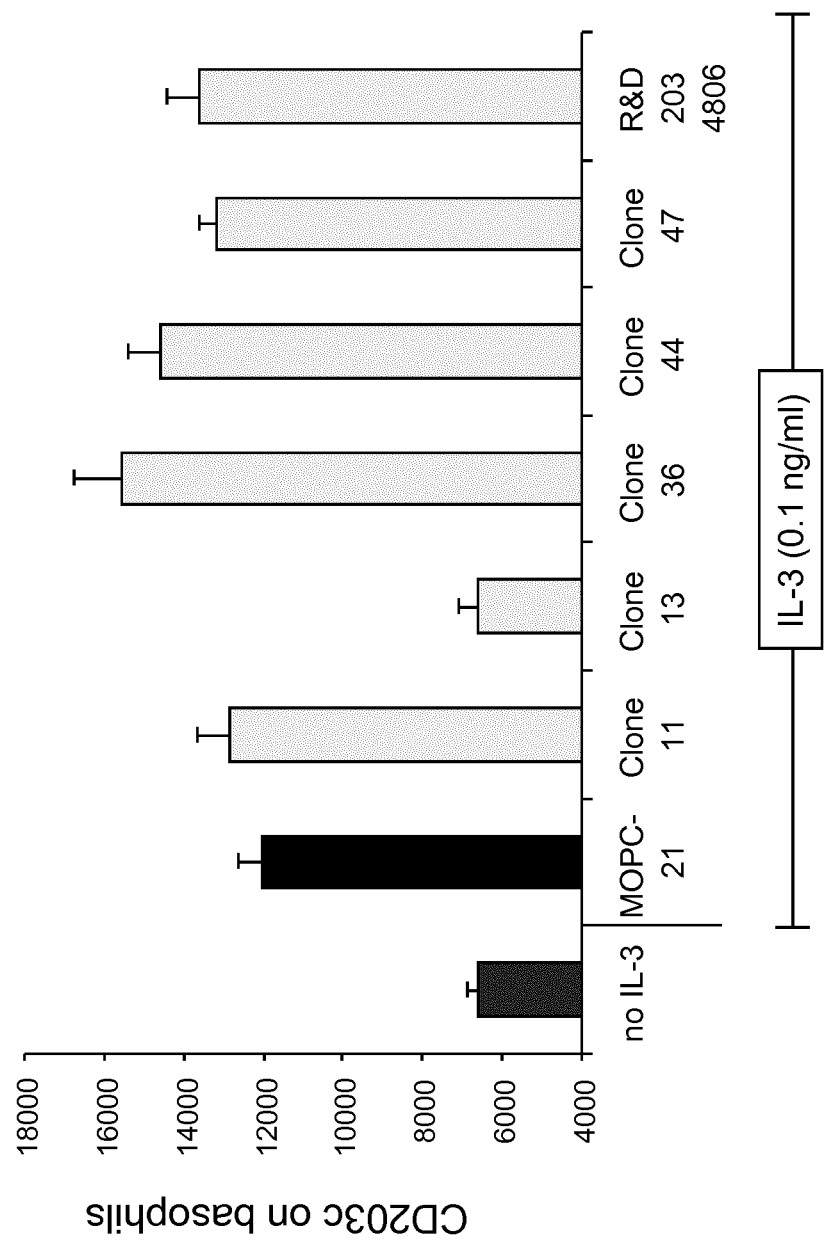
Figure 21:
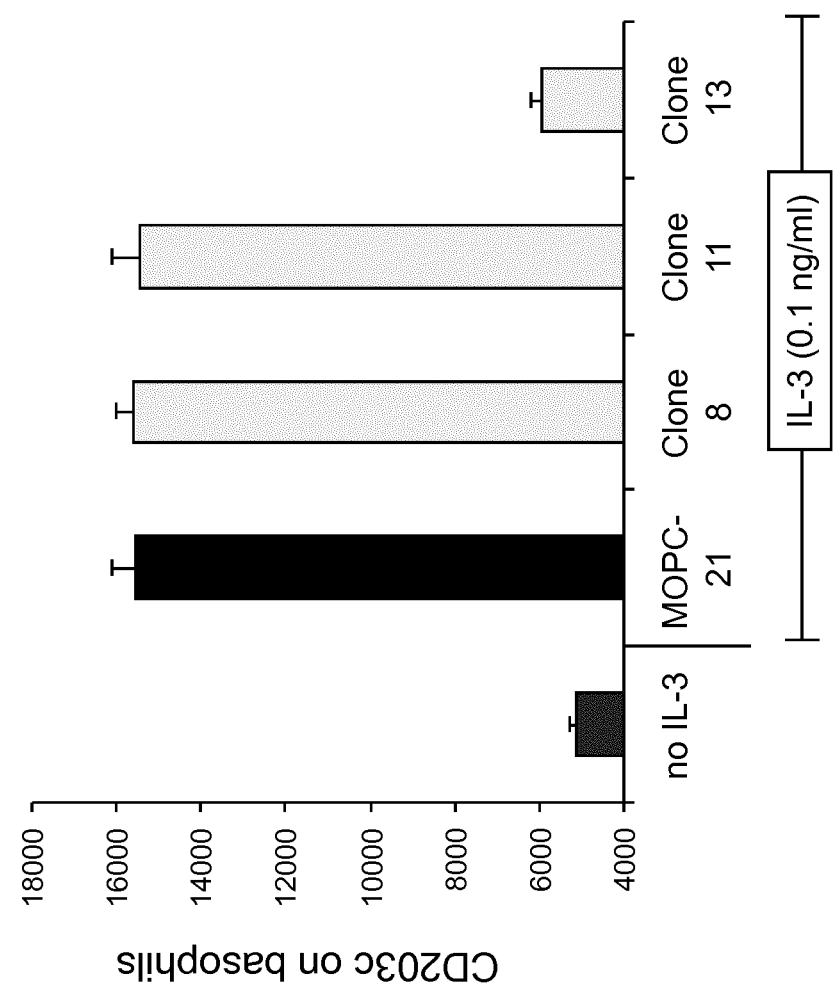

The clone 11 and the R&D clone 4806 efficiently block IL-3 dependent growth of TF1 cells (in the presence of 2.5 ng/ml E. coli expressed IL-3 the $IC_{50}$ is 10 ng/ml and 33 ng/ml, respectively; see FIGS. 13 and 14), but are basically unable to block the IL-3 effects of insect cell expressed IL-3 on primary human cells (see FIG. 19-21). In contrast, the antibody clone 13, that is much less effective in blocking IL-3 effects on TF1 cells ($IC_{50}$ at 200 ng/ml; see FIG. 12), completely and very efficiently blocks the IL-3 effects as measured with primary human peripheral blood leukocytes ($IC_{50}$ at 40 ng/ml; see FIGS. 19-22, and 24-28).

Apart from clone 13, a second monoclonal antibody (clone P8C11C8-6) has been generated that completely blocks IL-3 activity as measured with primary human cells (see FIGS. 22, and 32-36). The blocking capability of the antibodies of the present invention on primary human blood cells obtained from RA patients are shown in FIG. 23.

Example 6—Epitope Mapping for the Anti-IL-3 Antibody P8C11C8-6

An ELISA plate was coated overnight with various peptides derived from human IL-3 at a concentration of 10 µg/ml in PBS. Coating with PBS alone was used as negative control. After washing and blocking with PBS/1% BSA (bovine serum albumin) clone P8C11C8-6 (40 µg/ml) was applied for 1 h at room temperature. After washing the bound P8C11C8-6 antibody was detected with a secondary HRP-labelled rabbit anti-mouse polyclonal antibody and a color substrate reaction (see FIG. 30).

The amino acid residue positions are derived from the position of the human IL-3 without the signal peptide of the first 27 amino acids. The sequence of the human IL-3 is deposited in GenBank under accession number NP_000579.2, version GI:28416915.

IL3-1 (aa 1-27): APMTQTTPLKTSWVNCSNMI-DEIITHL (SEQ ID NO:2) IL3-1A (aa 1-24 with 2 mutations underlined): APMTQTTPLKTSW<u>AK</u>CSNMIDEII (SEQ ID NO:3)

IL3-1B (aa 1-24 with 1 mutation underlined): APMTQTT <u>S</u>LKTSWVNCSNMIDEII (SEQ ID NO:4)

IL3-2 (aa 22-48): EIITHLKQPPLPLL-DFNNLNGEDQDIL (SEQ ID NO:1)

IL3-3 (aa 43-69): EDQDILMENNLRRPNLEAFN-RAVKSLQ (SEQ ID NO:5)

IL3-4 (aa 64-90): AVKSLQNASAIESILKNLLPCL-PLATA (SEQ ID NO:6)

IL3-5 (aa 85-111): LPLATAAPTRHPIHIKDGDWNE-FRRKL (SEQ ID NO:7)

IL3-6 (aa 106-133): EFRRKLTFYLKTLENAQAQQT-TLSLAIF (SEQ ID NO:8)

An ELISA plate was coated overnight with various peptides derived from human IL-3 at a concentration of 5 µg/ml in PBS. Coating with PBS alone was used as negative control. After washing and blocking with PBS/1% BSA (bovine serum albumin) clone P8C11C8-6 was applied at various concentrations for 1 h at room temperature. After washing the bound P8C11C8-6 antibody was detected with a secondary HRP-labelled rabbit anti-mouse polyclonal antibody and a color substrate reaction (ABTS).

The results are shown in FIGS. 30 and 31A.

The experiment was repeated with the following peptides.
IL3-2 (aa 22-48): EIITHLKQPPLPLLDFNNLNGEDQIL (SEQ ID NO:1)
IL3-2a (aa 30-48): PPLPLLDFNNLNGEDQIL (SEQ ID NO:9)
IL3-26 (aa 26-48): HLKQPPLPLLDFNNLNGEDQIL (SEQ ID NO:11)
IL3-28 (aa28-48): KQPPLPLLDFNNLNGEDQIL (SEQ ID NO:12)

The experimental conditions were as detailed above, with the exception that after washing and blocking with PBS/1% BSA (bovine serum albumin) 20 µg/ml of clone P8C11C8-6 was applied for 1 h at room temperature.

The results are shown in FIG. 31B. The epitope recognized by P8C11C8-6 is contained within aa22 (E) to aa 48 (L). Further experiments suggested that the epitope recognized by P8C11C8-6 is located within amino acids 26 (H) to 36 (D) of the amino acid sequence as defined in SEQ ID NO:10 and that the epitope of P8C11C8-6 includes the amino acids 27-29 (LKQ).

Example 7—Analysis of Interaction Between Clone 13 and Clone P8C11C8-6

ELISA wells were coated overnight with human IL-3 (0.5 µg/ml) in PBS. After washing and blocking with PBS/1% BSA (bovine serum albumin) unlabeled antibody clone 13 or clone P8C11C8-6 were applied at various concentrations for 1 h at room temperature. Without washing or removal of the unlabeled antibodies, HRP-labelled antibody clone 13 (0.4 µg/ml) was added for 1 h at room temperature. After washing a color substrate reaction was performed with ABTS and optical density (OD) was measured. As can be seen from the results shown in FIGS. 36-38, clone P8C11C8-6 and clone 13 do not compete with each other. Clone P8C11C8-6 does also not interfere with the binding of Clone 13 or Clone 11 to IL-3 (see FIG. 37).

ELISA wells were coated overnight with antibody Clone 13 (5 µg/ml). IL-3 (1 ng/ml) was preincubated with various concentrations of Clone 13 or Clone P8C11C8-6 for 30 min, then applied to the ELISA plate and incubated at room temperature for 1 h. After washing, bound IL-3 was detected with HRP-labelled antibody clone 11 (0.4 µg/ml 1 h at room temperature). After washing a color substrate reaction was performed with TMB and optical density (OD) was measured.

P8C11C8-6 does also not prevent binding of clone 13 or clone 11 to IL-3 (see FIG. 38).

ELISA wells were coated overnight with human IL-3 (0.5 µg/ml) in PBS. After washing and blocking with PBS/1% BSA (bovine serum albumin) unlabeled antibody clone P8C11C8-6, clone 13 (AK13) or clone 11 (AK11) were applied at various concentrations for 1 h at room temperature. Without washing or removal of the unlabeled antibodies, HRP-labelled antibody clone 11 (0.4 µg/ml) HRP-labelled antibody clone 13 (0.4 µg/ml) or HRP-labelled antibody clone P8C11C8-6 (0.13 µg/ml) was added for 1 h at room temperature. After washing a color substrate reaction was performed with TMB and optical density (OD) was measured.

Example 8—Assessment of the Activity of E. coli or Insect Cell Derived IL-3 on Human Basophils As show in FIG. 39, the activity of E. coli or insect cell derived IL-3 on human basophils is comparable. Various concentrations of IL-3 produced in insect cells (Biolegend) or E. coli (Peprotech) or PBS as negative control were added for 1 h at 37° C. to fresh human EDTA blood. Cells were then stained with directly labelled antibodies against CD11b, CD203c, CD123 and HLA-DR for 20 min on ice and analyzed by flow cytometry to identify basophils and to quantify upregulation of CD203c on basophils.

As shown in FIG. 40, the activity of IL-3 from various sources is similar in a bioassay with human basophils. Human IL-3 produced in HEK cells (Biomol), insect cells (Biolegend) or E. coli (Peprotech) and Rhesus IL-3 expressed in E. coli was incubated at various concentrations with fresh human EDTA blood for 1 h at 37° C. Cells were then stained with directly labelled antibodies against CD203c, CD123 for 20 min on ice and analyzed by flow cytometry to identify basophils and to quantify upregulation of CD203c on basophils.

Example 9—Assessment of the Blocking Activity of Anti-Human IL-3 Antibodies

As shown in FIG. 41, Clone 11 and R&D mab 203 only block the activity of E. coli derived IL-3, but not the activity of insect cell derived IL-3 in an assay with basophils.

IL-3 (0.1 ng/ml) produced in insect cells (Biolegend) or E. coli (Peprotech) was preincubated with various concentrations of anti-IL-3 antibodies or mouse IgG1 isotype control antibody (MOPC-21) for 45 min at room temperature and added to fresh human EDTA blood. Only PBS was added to human EDTA blood as negative control. After 1 h incubation at 37° C. cells were stained with directly labelled antibodies against CD11b, CD203c, CD123 and HLA-DR for 20 min on ice and analysed by flow cytometry to identify basophils and to quantify upregulation of CD203c on basophils. The CD203 expression of the negative control (PBS) was subtracted.

As shown in FIG. 42, clone 11 and R&D mab 203 only block the activity of E. coli derived IL-3, but not the activity of insect cell derived IL-3 in an assay with basophils. IL-3 (0.1 ng/ml or 0.2 ng/ml) produced in HEK cells (Biomol), insect cells (Biolegend) or E. coli (Peprotech) or rhesus IL-3 expressed in E. coli (Biomol) was preincubated with various concentrations of anti-IL-3 antibodies for 1 h at room temperature and added to fresh human EDTA blood. Only PBS was added to human EDTA blood as negative control. After 1 h incubation at 37° C. cells were stained with directly labelled antibodies against CD203c and CD123 for 20 min on ice and analysed by flow cytometry to identify basophils and to quantify upregulation of CD203c on basophils.

As shown in FIG. 43, clone 13 and P8C11C8-6 block bioactivity of IL-3 released by primary T cells from RA-patients and Clone 11 has little inhibitory activity (IL-3 in the cell culture supernatant of anti-CD3 activated PBMC from RA patients; the IL-3 concentration was measured by a sandwich ELISA with clone 13+clone 11-HRP and insect cell derived IL-3 as standard). PBMC (500.000/well) from 6 RA patients were activated for 3 days with anti-CD3 antibodies (clone OKT3, 5 µg/ml) in 200 µl RPMI medium with 10% FCS. The supernatant (SN) was added at various dilutions to fresh human EDTA blood for 1 h at 37° C. In addition, the SN was preincubated with anti-IL-3 antibodies (10 µg/ml, P8C11=P8C11C8-6, K13=Clone 13, K11=Clone 11) for 45 min at room temperature and added to fresh human EDTA blood for 1 h at 37° C. The IL-3 concentration in the supernatant was measured by ELISA and the final concentration of SN 100% in the EDTA blood is provided in the figure legend. Cells were then stained with directly labelled antibodies against CD11b, CD203c, CD123 and HLA-DR for 20 min on ice and analysed by flow cytometry to identify basophils and to quantify upregulation of CD203c on basophils.

As shown in FIG. 44, clone 13 and P8C11C8-6 block bioactivity of IL-3 produced by human PBMC and Clone 11 and R&D mab203 have little inhibitory activity. PBMC (500.000/well) from an RA patient were activated for 3 days with anti-CD3 antibodies (clone OKT3, 5 µg/ml) in 200 µl RPMI medium with 10% FCS. The supernatant (PBMC-SN) was used at a dilution containing 175 µg/ml IL-3 (measured by ELISA with P8C11C8-6+Clone13-HRP). The PBMC-SN was preincubated with various concentrations of various anti-IL-3 antibodies for 1 h at room temperature and added to fresh human EDTA blood for 1 h at 37° C. Cells were then stained with directly labelled antibodies against CD203c and CD123 for 20 min on ice and analysed by flow cytometry to identify basophils and to quantify upregulation of CD203c on basophils.

As shown in FIG. 45, clone 11 and R&D mab 203 only block the activity of *E. coli* derived IL-3, but not the activity of insect cell derived IL-3 in the TF-1 assay. IL-3 (2.5 ng/ml) produced in insect cells (Biolegend) or *E. coli* (Peprotech) was preincubated with various concentrations of anti-IL-3 antibodies or mouse IgG1 isotype control antibody (MOPC-21) for 60 min at room temperature and added to 10,000 TF-1 cells during a 5 day culture. The number of living cells was quantified using MTT assay (LCG Standard-ATCC). The TF-1 cell proliferation in the absence of IL-3 was subtracted and the results are shown as % of the positive control (IL-3 2.5 ng/ml without antibodies).

As shown in FIG. 46, clone 11 and R&D mab 203 only block the activity of *E. coli* derived IL-3, but not the activity of IL-3 from insect cells or HEK293 cells in the TF-1 cell assay; and Rhesus IL-3 is not blocked by the antibodies. Human IL-3 (2.5 ng/ml) produced in human HEK293 cells (Biomol), insect cells (Biolegend) or *E. coli* (Peprotech) or Rhesus IL-3 produced in *E. coli* (Biomol) was preincubated with various concentrations of anti-IL-3 antibodies for 60 min at room temperature and added to 10,000 TF-1 cells during a 5 day culture. Living cells were quantified by MTT assay (LCG Standard-ATCC) and OD values are shown.

Example 10—IL-3 Detection by Sandwich ELISA

As shown in FIG. 47, IL-3 from various sources can be detected by sandwich ELISA and only the pair of clone13+ P8C11C8-6 detects IL-3 expressed in HEK293 cells.

ELISA wells were coated overnight with different IL-3 antibodies (5 µg/ml) in PBS. Wells were washed with PBS/Tween20 and blocked with PBS/1% BSA for 2 h at RT. Then IL-3 produced in HEK293 cells (Biomol), insect cells (Biolegend) or *E. coli* (Peprotech) was applied at various concentrations diluted in PBS/1% BSA. After washing with PBS/Tween20 different HRP-labelled detection-antibodies (0.4 µg/ml) were added in PBS/BSA for 1 h at RT.

After washing with PBS/Tween20 HRP-labelled Clone-13 (0.4 µg/ml) was used as detection-antibody and added in PBS/BSA for 1 h at RT. The results are shown in FIG. 47.

After washing with PBS/Tween20 HRP-labelled P8C11C8-6 (0.1 µg/ml) was used as detection-antibody and added in PBS/BSA for 1 h at RT. The results are shown in FIG. 47.

After washing a color reaction was performed with TMB substrate and optical density was measured. Background values (OD values measured in the absence of IL-3) were subtracted.

As shown in FIG. 48 IL-3 from various sources can be detected by two different sandwich ELISAs.

ELISA wells were coated overnight with different IL-3 antibodies (Clone 13 or P8C11C8-6 at 5 µg/ml) in PBS. Wells were washed with PBS/Tween20 and blocked with PBS/1% BSA for 2 h at RT. Then IL-3 produced in HEK293 cells (Biomol) or insect cells (Biolegend) was applied at various concentrations diluted in PBS/1% BSA. After washing with PBS/Tween20 different HRP-labelled detection-antibodies (Clone11-HRP or Clone13-HRP at 0.4 µg/ml) were added in PBS/BSA for 1 h at RT. After washing a color reaction was performed with TMB substrate and optical density was measured. Background values (OD values measured in the absence of IL-3) were subtracted.

As shown in FIG. 49 IL-3 produced by human PBMC can be detected using two different sandwich ELISAs.

PBMC (500.000/well) from 9 RA patients were activated for 3 days with anti-CD3 antibodies (clone OKT3, 5 µg/ml) in 200 µl RPMI medium with 10% FCS. The supernatant (SN) was recovered. ELISA wells were coated overnight with different IL-3 antibodies (5 µg/ml) in PBS. Wells were washed with PBS/Tween20 and blocked with PBS/1% BSA for 2 h at RT. Then the supernatant (SN) was applied at various concentrations diluted in PBS/1% BSA. After washing with PBS/Tween20 different HRP-labelled detection-antibodies (0.4 µg/ml) were added in PBS/BSA for 1 h at RT. After washing a color reaction was performed with TMB substrate and optical density was measured. Background values (OD values measured in the absence of IL-3) were subtracted.

FIG. 50 shows the result of a bioassay with human basophils for detection of IL-3 from various sources.

Various concentrations of IL-3 produced in insect cells (Biolegend) or HEK cells (Biomol) were added for 1 h at 37° C. to fresh human EDTA blood. Cells were then stained with directly labelled antibodies against CD203c and CD123 for 20 min on ice and analyzed by flow cytometry to identify basophils and to quantify upregulation of CD203c on basophils.

FIG. 51 shows the quantification of human PBMC derived IL-3 with ELISAs and Bioassay and that the Quantification of IL-3 with ELISA (P8C11C8-6+Clone13-HRP) correlates very well with the bioactivity of human PBMC-derived IL-3. The assays were performed as described above using the standard curves shown in the corresponding Figures. Insect cell derived IL-3 was used as standard.

The invention claimed is:

1. An anti-human interleukin-3 (anti-hIL3) antibody produced by hybridoma cell line DSM ACC3281.

2. The anti-hIL3 antibody or fragment thereof according to claim 1 wherein binding of the antibody or fragment thereof to interleukin-5 (IL-5) or granulocyte-macrophage colony-stimulating factor (GM-CSF) is less than 5%, as compared to the binding of the antibody or fragment thereof to hIL-3.

3. A nucleic acid, encoding the anti-hIL3 antibody as defined in claim 1.

4. A pharmaceutical composition comprising a pharmaceutically effective amount of the anti-hIL-3 antibody according to claim 1 and optionally a pharmaceutically acceptable excipient and/or carrier.

5. A method of obtaining an anti-hIL-3 antibody as defined in claim 1, comprising immunizing an animal with a glycosylated hIL-3 peptide or an active part thereof and obtaining the anti-hIL-3 antibody from the animal.

6. The method of claim 5, wherein the glycosylated human hIL-3 peptide is a peptide expressed by a primary human cell.

7. A method for detecting hIL-3 in human cells or in a sample from a patient, comprising contacting the cells or the sample with the anti-hIL3 antibody of claim 1 and detecting hIL-3 using ELISA.

8. A method for inhibiting hIL-3 activity or decreasing hIL-3 expression levels in a patient comprising administering the hIL-3 antibody of claim 1 to the patient.

* * * * *

SEQUENCE LISTING

<160> NUMBER OF SEQ ID NOS: 12

<210> SEQ ID NO 1
<211> LENGTH: 27
<212> TYPE: PRT
<213> ORGANISM: Artificial sequence
<220> FEATURE:
<223> OTHER INFORMATION: aa 22-48 of human IL-3 without signal peptide

<400> SEQUENCE: 1

Glu Ile Ile Thr His Leu Lys Gln Pro Pro Leu Pro Leu Leu Asp Phe
1               5                   10                  15

Asn Asn Leu Asn Gly Glu Asp Gln Asp Ile Leu
            20                  25

<210> SEQ ID NO 2
<211> LENGTH: 27
<212> TYPE: PRT
<213> ORGANISM: Artificial sequence
<220> FEATURE:
<223> OTHER INFORMATION: aa 1-27 of human IL-3 without signal peptide

<400> SEQUENCE: 2

Ala Pro Met Thr Gln Thr Thr Pro Leu Lys Thr Ser Trp Val Asn Cys
1               5                   10                  15

Ser Asn Met Ile Asp Glu Ile Ile Thr His Leu
            20                  25

<210> SEQ ID NO 3
<211> LENGTH: 24
<212> TYPE: PRT
<213> ORGANISM: Artificial sequence
<220> FEATURE:
<223> OTHER INFORMATION: aa 1-24 of human IL-3 without signal peptide
<220> FEATURE:
<221> NAME/KEY: VARIANT
<222> LOCATION: (14)..(14)
<223> OTHER INFORMATION: mutation V to A
<220> FEATURE:
<221> NAME/KEY: VARIANT
<222> LOCATION: (15)..(15)
<223> OTHER INFORMATION: mutation N to K

<400> SEQUENCE: 3

Ala Pro Met Thr Gln Thr Thr Pro Leu Lys Thr Ser Trp Ala Lys Cys
1               5                   10                  15

Ser Asn Met Ile Asp Glu Ile Ile
            20

<210> SEQ ID NO 4
<211> LENGTH: 24
<212> TYPE: PRT
<213> ORGANISM: Artificial sequence
<220> FEATURE:
<223> OTHER INFORMATION: aa 1-24 of human IL-3 without signal peptide
<220> FEATURE:
<221> NAME/KEY: VARIANT
<222> LOCATION: (8)..(8)
<223> OTHER INFORMATION: mutation P to S

<400> SEQUENCE: 4

Ala Pro Met Thr Gln Thr Thr Ser Leu Lys Thr Ser Trp Val Asn Cys
1               5                   10                  15

Ser Asn Met Ile Asp Glu Ile Ile
            20

```
<210> SEQ ID NO 5
<211> LENGTH: 27
<212> TYPE: PRT
<213> ORGANISM: Artificial sequence
<220> FEATURE:
<223> OTHER INFORMATION: aa 43-69 of human IL-3 without signal peptide

<400> SEQUENCE: 5

Glu Asp Gln Asp Ile Leu Met Glu Asn Asn Leu Arg Arg Pro Asn Leu
1               5                   10                  15

Glu Ala Phe Asn Arg Ala Val Lys Ser Leu Gln
            20                  25

<210> SEQ ID NO 6
<211> LENGTH: 27
<212> TYPE: PRT
<213> ORGANISM: Artificial sequence
<220> FEATURE:
<223> OTHER INFORMATION: aa 64-90 of human IL-3 without signal peptide

<400> SEQUENCE: 6

Ala Val Lys Ser Leu Gln Asn Ala Ser Ala Ile Glu Ser Ile Leu Lys
1               5                   10                  15

Asn Leu Leu Pro Cys Leu Pro Leu Ala Thr Ala
            20                  25

<210> SEQ ID NO 7
<211> LENGTH: 27
<212> TYPE: PRT
<213> ORGANISM: Artificial Sequence
<220> FEATURE:
<223> OTHER INFORMATION: aa 85-111 of human IL-3 without signal peptide

<400> SEQUENCE: 7

Leu Pro Leu Ala Thr Ala Ala Pro Thr Arg His Pro Ile His Ile Lys
1               5                   10                  15

Asp Gly Asp Trp Asn Glu Phe Arg Arg Lys Leu
            20                  25

<210> SEQ ID NO 8
<211> LENGTH: 28
<212> TYPE: PRT
<213> ORGANISM: Artificial Sequence
<220> FEATURE:
<223> OTHER INFORMATION: aa 106-133 of human IL-3 without signal peptide

<400> SEQUENCE: 8

Glu Phe Arg Arg Lys Leu Thr Phe Tyr Leu Lys Thr Leu Glu Asn Ala
1               5                   10                  15

Gln Ala Gln Gln Thr Thr Leu Ser Leu Ala Ile Phe
            20                  25

<210> SEQ ID NO 9
<211> LENGTH: 19
<212> TYPE: PRT
<213> ORGANISM: Artificial Sequence
<220> FEATURE:
<223> OTHER INFORMATION: aa 30-48 of human IL-3 without signal peptide

<400> SEQUENCE: 9

Pro Pro Leu Pro Leu Leu Asp Phe Asn Asn Leu Asn Gly Glu Asp Gln
1               5                   10                  15

Asp Ile Leu
```

```
<210> SEQ ID NO 10
<211> LENGTH: 133
<212> TYPE: PRT
<213> ORGANISM: Artificial Sequence
<220> FEATURE:
<223> OTHER INFORMATION: human IL-3 without signal peptide

<400> SEQUENCE: 10

Ala Pro Met Thr Gln Thr Thr Ser Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130

<210> SEQ ID NO 11
<211> LENGTH: 23
<212> TYPE: PRT
<213> ORGANISM: Artificial Sequence
<220> FEATURE:
<223> OTHER INFORMATION: aa 26-48 of human IL-3 without signal peptide

<400> SEQUENCE: 11

His Leu Lys Gln Pro Pro Leu Pro Leu Leu Asp Phe Asn Asn Leu Asn
1               5                   10                  15

Gly Glu Asp Gln Asp Ile Leu
            20

<210> SEQ ID NO 12
<211> LENGTH: 21
<212> TYPE: PRT
<213> ORGANISM: Artificial Sequence
<220> FEATURE:
<223> OTHER INFORMATION: aa 28-48 of human IL-3 without signal peptide

<400> SEQUENCE: 12

Lys Gln Pro Pro Leu Pro Leu Leu Asp Phe Asn Asn Leu Asn Gly Glu
1               5                   10                  15

Asp Gln Asp Ile Leu
            20
```